US011065258B2

(12) United States Patent
Zon et al.

(10) Patent No.: US 11,065,258 B2
(45) Date of Patent: *Jul. 20, 2021

(54) CALMODULIN INHIBITORS FOR THE TREATMENT OF RIBOSOMAL DISORDERS AND RIBOSOMAPATHIES

(71) Applicant: CHILDREN'S MEDICAL CENTER CORPORATION, Boston, MA (US)

(72) Inventors: Leonard I. Zon, Wellesley, MA (US); Alison M. Taylor, Cambridge, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 12 days.

This patent is subject to a terminal disclaimer.

(21) Appl. No.: 16/538,293

(22) Filed: Aug. 12, 2019

(65) Prior Publication Data

US 2020/0101083 A1 Apr. 2, 2020

Related U.S. Application Data

(63) Continuation of application No. 15/806,765, filed on Nov. 8, 2017, now Pat. No. 10,420,778, which is a
(Continued)

(51) Int. Cl.
*A61K 31/553* (2006.01)
*A61K 31/495* (2006.01)
(Continued)

(52) U.S. Cl.
CPC .......... *A61K 31/553* (2013.01); *A61K 31/145* (2013.01); *A61K 31/4184* (2013.01); *A61K 31/4375* (2013.01); *A61K 31/4418* (2013.01); *A61K 31/495* (2013.01); *A61K 31/4965* (2013.01); *A61K 31/54* (2013.01); *A61K 31/5415* (2013.01)

(58) Field of Classification Search
CPC ................ A61K 31/553; A61K 31/145; A61K 31/4184; A61K 31/4375; A61K 31/4418; A61K 31/495; A61K 31/4965; A61K 31/54; A61K 31/5415; A61K 31/10
USPC ....................................................... 514/603
See application file for complete search history.

(56) References Cited

U.S. PATENT DOCUMENTS 5,583,199 A 12/1996 Queensberry et al.
10,420,778 B2 * 9/2019 Zon .................... A61K 31/4375

FOREIGN PATENT DOCUMENTS

WO 1998/020905 A2 5/1998

OTHER PUBLICATIONS

Amsterdam et al., "Many Ribosomal Protein Genes are Cancer Genes in Zebrafish", PLoS Biol. 2(5):0690 (2004).
(Continued)

*Primary Examiner* — Taylor V Oh
(74) *Attorney, Agent, or Firm* — Nixon Peabody LLP; David S. Resnick; Susanna C. Benn

(57) ABSTRACT

The present invention relates generally to methods, compositions and kits for treatment of ribosomal disorders and ribosomopathy, e.g. Diamond Blackfan anemia (DBA). In some embodiments, the invention relates to methods for the use of calmodulin inhibitors and calcium channel blockers for treatment of ribosomal disorders and ribosomopathy, e.g. Diamond Blackfan anemia (DBA).

17 Claims, 13 Drawing Sheets

Specification includes a Sequence Listing.

Related U.S. Application Data continuation of application No. 14/385,524, filed as application No. PCT/US2013/028969 on Mar. 5, 2013, now Pat. No. 9,827,252.

(60) Provisional application No. 61/611,751, filed on Mar. 16, 2012, provisional application No. 61/611,845, filed on Mar. 16, 2012.

(51) Int. Cl.

| | |
|---|---|
| A61K 31/4965 | (2006.01) |
| A61K 31/54 | (2006.01) |
| A61K 31/5415 | (2006.01) |
| A61K 31/145 | (2006.01) |
| A61K 31/4184 | (2006.01) |
| A61K 31/4375 | (2006.01) |
| A61K 31/4418 | (2006.01) |

(56) References Cited

OTHER PUBLICATIONS

Burns et al., "A genetic screen in zebrafish defines a hierarchical network of pathways required for hematopoietic stem cell emergence", Blood 113(23):5776-5782 (2012).
Ceccaldi et al., "Bone marrow failure in Fanconi anemia is triggered by an exacerbated p53/p21 DNA damage response that impairs hematopoietic stem and progenitor cells", Cell Stem Cell 11(1):36-49 (2012).
Chakraborty et al., "Loss of Ribosomal Protein L11 Affects Zebrafish Embryonic Development through a p53-Dependent Apoptotic Response", PLoS One 4(1):e4152 (2009).
Chin et al., "Calmodulin: a prototypical calcium sensor", Trends in Cell Biology 10(8):322-328 (2000).
Craig et al., "The MDM2 Ubiquitination Signal in the DNA-Binding Domain of p53 Forms a Docking Site for Calcium Calmodulin Kinase Superfamily Members", Molecular and Cellular Biology 27(9):3542-3555 (2007).
Danilova et al., "Ribosomal protein S19 deficiency in zebrafish leads to developmental abnormalities and defective erythropoiesis through activation of p53 protein family", Blood 112(13):5228-5237 (2008).
Daniolva et al., "Ribosomal protein L11 mutation in zebrafish leads to haematopoietic and metabolic defects", Br J Haematol 152(2):217-228 (2011).
Draptchinskaia et al., "The gene encoding ribosomal protein S19 is mutated in Diamond-Blackfan anaemia", Nature Genetics 21(2):169-175 (1999).
Dutt et al., "Haploinsufficiency for ribosomal protein genes causes selective activation of p53 in human erythroid progenitor cells", Blood 117(9):2567-2576 (2011).
Ebert et al., "An RNA interference model of RPS19 deficiency in Diamond-Blackfan anemia recapitulates defective hematopoiesis and rescue by dexamethasone: identification of dexamethasone-responsive genes by microarray", Blood 105(12):4620-4626 (2005).
Ebert et al., "Identification of RPS14 as a 5q-syndrome gene by RNA interference screen", Nature 451 (7176):335-339 (2008).
Flygare et al., "Deficiency of ribosomal protein S19 in CD34+ cells generated by siRNA blocks erythroid development and mimics defects seen in Diamond-Blackfan anemia", Blood 105(12):4627-4634 (2005).
Fumagalli et al., "Absence of nucleolar disruption after impairment of 40S ribosome biogenesis reveals an rpL11-translation-dependent mechanism of p53 induction", Nat Cell Biol 11(4):501-508 (2009).
Gujja et al., "Iron overload cardiomyopathy: better understanding of an increasing disorder", J Am Coll Cardiol 56(13) 1001-1012 (2010).

Hidaka et al., "A Novel Vascular Relaxing Agent, N-(6-Aminohexyl)-5-Chloro-1-Naphthalensulfonamide Which Affects Vascular Smooth Muscle Actomyosin", J Pharmacol Exp Ther. 207(1):8-15 (1978).
Hidaka et al., "N-(6-aminohexyl)-5-chloro-1-naphthalenesulfonamide, a calmodulin antagonist, inhibits cell proliferation", PNAS 78(7):4354-4357 (1981).
Inagaki et al., "Naphthalenesulfonamides as calmodulin antagonists and protein kinase inhibitors", Mol Pharmacol 29 (6):577-581 (1986).
Isenberg et al., "Thrombospondin-1 inhibits endothelial cell responses to nitric oxide in a cGMP-dependent manner", PNAS 102(37):13141-13146 (2005).
Jaako et al., "Mice with ribosomal protein S19 deficiency develop bone marrow failure and symptoms like patients with Diamond-Blackfan anemia", Blood 118(23):6087-6096 (2011).
Jones et al., "Prevention of the neurocristopathy Treacher Collins syndrome through inhibition of p53 function", Nat Med. 14(2):125-133 (2008).
Katayama et al., "A Role for Calmdulin in the Growth of Human Hematopoietic Progenitor Cells", Blood 75:1446-54 (1990).
Lu et al., "Biologic properties and enucleation of red blood cells from human embryonic stem cells", Blood 112 (12):4475-4484 (2008).
McGowan et al., "Ribosomal mutations cause p53-mediated dark skin and pleiotropic effects", Nat Genet 40 (8):963-970 (2008).
Miyake et al., "Development of Cellular Models for Ribosomal Protein S19 (RPS19)-Deficient Diamond-Blackfan Anemia Using Inducible Expression of siRNA Against RPS19", Mol Ther. 11(4):627-637 (2005).
North et al., "Hematopoietic stem cell development is dependent on blood flow", Cell 137(4):736-748 (2009).
North et al., "Prostaglandin E2 regulates vertebrate haematopoietic stem cell homeostasis", Nature 447 (7147):1007-1011 (2007).
Paffett-Lugassy et al., "Analysis of Hematopoietic Development in the Zebrafish", Methods Mol Med. 105:171-198 (2005).
Rodriguez-Vilarrupla et al., "Binding of Calmodulin to the Carboxy-Terminal Region of p21 Induces Nuclear Accumulation via Inhibition of Protein Kinase C-Mediated Phosphorylation of Ser153", Mol Cell Biol 25(16):7364-7374 (2005).
Sweitzer et al., "Calmodulin activates nuclear protein import: A link between signal transduction and nuclear transport", Proc. Natl. Acad. Sci. USA 93(25):14574-14759 (1996).
Takagi et al., "Regulation of p53 Translation and Induction After DNA Damage by Ribosomal Protein L26 and Nucleolin", Cell 123(3):49-63 (2005).
Taules et al., "Calmodulin Binds to p21(Cip1) and Is Involved in the Regulation of Its Nuclear Localization", The Journal of Biological Chemistry 274(35):24445-24448 (1999).
Taylor et al., "Hematopoietic defects in rps29 mutant zebrafish depend upon p53 activation", Exp Hematol 40 (3):228-237 (2012).
Taylor et al., "Modeling Diamond Blackfan anemia in the zebrafish", Seminars in Hematology 48(2):81-88 (2011).
Teng et al., "Growth control and ribosomopathies", Current Opinions in Genetics & Development 23(1):63-71 (2013).
Thisse et al., "High-resolution in situ hybridization to whole-mount zebrafish embryos", Nature Protocols 3(1):59-69 (2008).
Torihara et al., "Erythropoiesis failure due to RPS19 deficiency is independent of an activated Tp53 response in a zebrafish model of Diamond-Blackfan anaemia", 152(5):648-654 (2011).
Vlachos et al., "Diagnosing and treating Diamond Blackfan anaemia: results of an international clinical consensus conference", British Journal of Haematology 142(6):859-876 (2008).
Vlachos et al., "How I treat Diamond-Blackfan anemia", Blood 116(19):3715-3723 (2010).
Wagstaff et al., "Importins and Beyond: Non-Conventional Nuclear Transport Mechanisms", Traffic 10 (9):1188-1198 (2009).
Wikipedia, Hematologic Disesae, Oct. 2010, p. 1-4.

\* cited by examiner

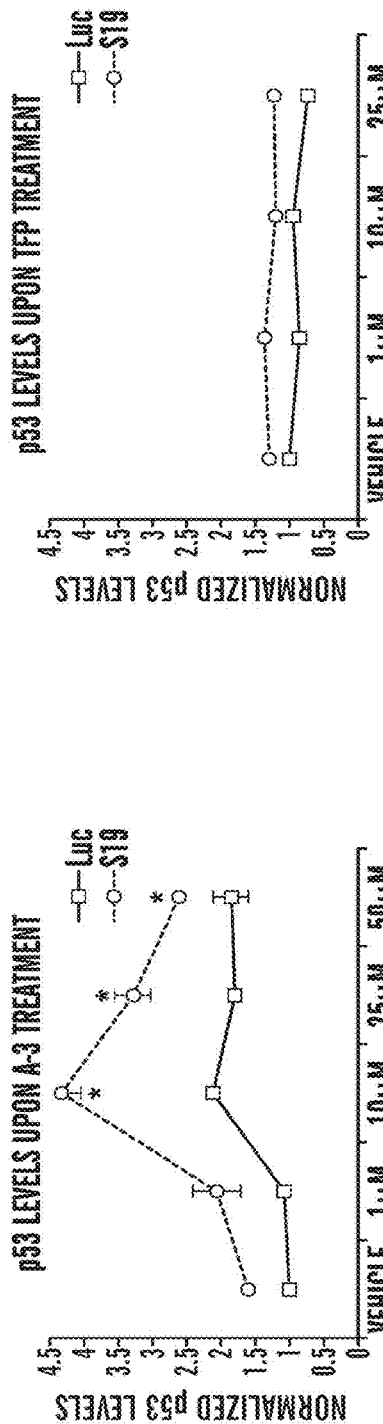
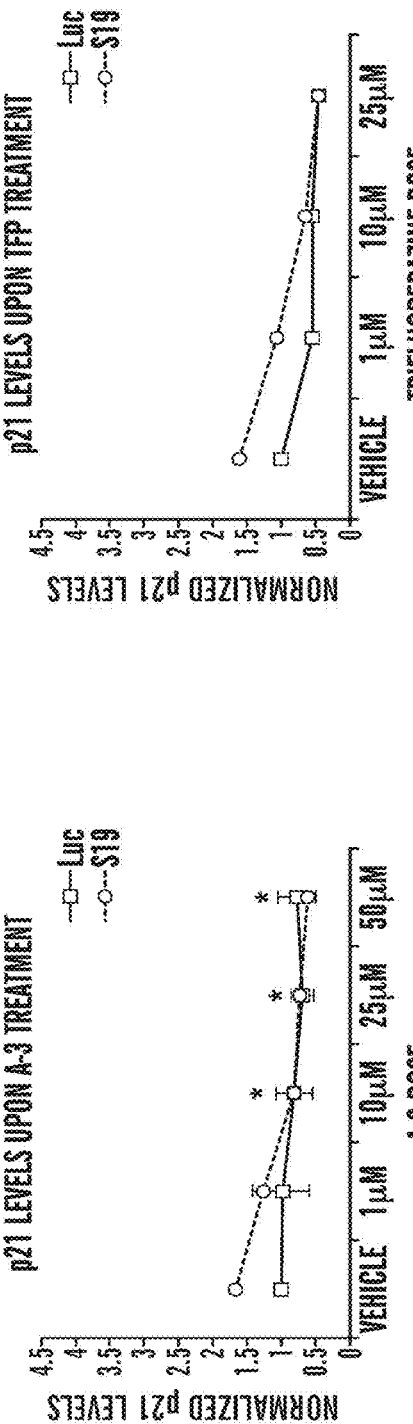
FIG. 3A
FIG. 3C
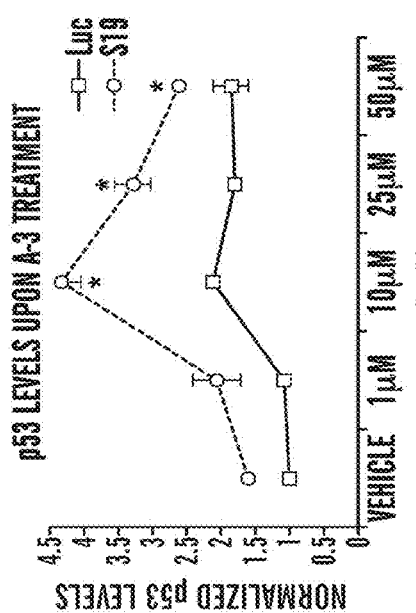
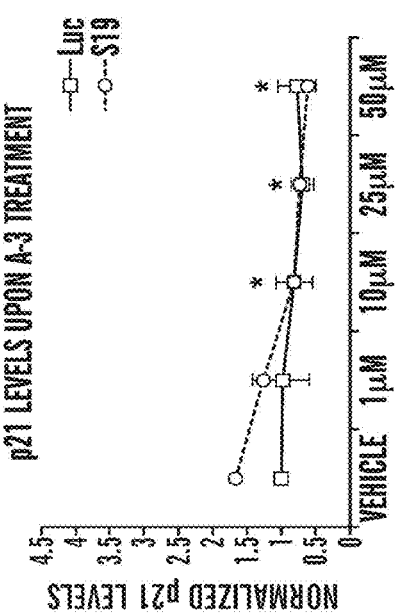
FIG. 3B
FIG. 3D

SEQUENCE LISTING

```
<160> NUMBER OF SEQ ID NOS: 4

<210> SEQ ID NO 1
<211> LENGTH: 1991
<212> TYPE: DNA
<213> ORGANISM: Homo sapiens

<400> SEQUENCE: 1
gcaggtttag cgccactctg ctggctgagg ctgcggagag tgtgcggctc caggtgggct      60
cacgcggtcg tgatgtctcg ggagtcggat gttgaggctc agcagtctca tggcagcagt     120
```

| | |
|---|---|
| gcctgttcac agccccatgg cagcgttacc cagtcccaag gctcctcctc acagtcccag | 180 |
| ggcatatcca gctcctctac cagcacgatg ccaaactcca gccagtcctc tcactccagc | 240 |
| tctgggacac tgagctcctt agagacagtg tccactcagg aactctattc tattcctgag | 300 |
| gaccaagaac ctgaggacca agaacctgag gagcctaccc ctgcccctg gctcgatta | 360 |
| tgggcccttc aggatggatt tgccaatctt gagacagagt ctggccatgt acccaatct | 420 |
| gatcttgaac tcctgctgtc atctgatcct cctgcctcag cctcccaaag tgctgggata | 480 |
| agaggtgtga ggcaccatcc ccggccagtt tgcagtctaa aatgtgtgaa tgacaactac | 540 |
| tggtttggga gggacaaaag ctgtgaatat tgctttgatg aaccactgct gaaaagaaca | 600 |
| gataaatacc gaacatacag caagaaacac tttcggattt tcagggaagt gggtcctaaa | 660 |
| aactcttaca ttgcatacat agaagatcac agtggcaatg aacctttgt aaatacagag | 720 |
| cttgtaggga aggaaaacg ccgtcctttg aataacaatt ctgaaattgc actgtcacta | 780 |
| agcagaaata agttttttgt cttttttgat ctgactgtag atgatcagtc agtttatcct | 840 |
| aaggcattaa gagatgaata catcatgtca aaaactcttg gaagtggtgc ctgtggagag | 900 |
| gtaaagctgg ctttcgagag gaaaacatgt aagaaagtag ccataaagat catcagcaaa | 960 |
| aggaagtttg ctattggttc agcaagagag gcagacccag ctctcaatgt tgaaacagaa | 1020 |
| atagaaattt tgaaaagct aaatcatcct tgcatcatca agattaaaaa cttttttgat | 1080 |
| gcagaagatt attatattgt tttggaattg atggaagggg agagctgtt tgacaaagtg | 1140 |
| gtggggaata aacgcctgaa agaagctacc tgcaagctct attttaccag atgctcttg | 1200 |
| gctgtgcagt accttcatga aaacggtatt ataccgtg acttaaagcc agagaatgtt | 1260 |
| ttactgtcat ctcaagaaga ggactgtctt ataaagatta ctgattttgg gcactccaag | 1320 |
| attttgggag agacctctct catgagaacc ttatgtggaa ccccaccta cttggcgcct | 1380 |
| gaagttcttg tttctgttgg gactgctggg tataaccgtg ctgtggactg ctggagttta | 1440 |
| ggagttattc tttttatctg ccttagtggg tatccaccct tctctgagca taggactcaa | 1500 |
| gtgtcactga aggatcagat caccagtgga aaatacaact tcattcctga agtctgggca | 1560 |
| gaagtctcag agaaagctct ggaccttgtc aagaagttgt tggtagtgga tccaaaggca | 1620 |
| cgttttacga cagaagaagc cttaagacac ccgtggcttc aggatgaaga catgaagaga | 1680 |
| aagtttcaag atcttctgtc tgaggaaaat gaatccacag ctctacccca ggttctagcc | 1740 |
| cagccttcta ctagtcgaaa gcggccccgt gaaggggaag ccgagggtgc cgagaccaca | 1800 |
| aagcgcccag ctgtgtgtgc tgctgtgttg tgaactccgt ggtttgaaca cgaaagaaat | 1860 |
| gtaccttctt tcactctgtc atctttcttt tctttgagtc tgtttttta tagtttgtat | 1920 |
| tttaattatg ggataattg cttttcaca gtcactgatg tacaattaaa aacctgatgg | 1980 |
| aacctggaaa a | 1991 |

<210> SEQ ID NO 2
<211> LENGTH: 586
<212> TYPE: PRT
<213> ORGANISM: Homo sapiens

<400> SEQUENCE: 2

Met Ser Arg Glu Ser Asp Val Glu Ala Gln Gln Ser His Gly Ser Ser
1               5                   10                  15

Ala Cys Ser Gln Pro His Gly Ser Val Thr Gln Ser Gln Gly Ser Ser
            20                  25                  30

Ser Gln Ser Gln Gly Ile Ser Ser Ser Ser Thr Ser Thr Met Pro Asn

```
                35                  40                  45
Ser Ser Gln Ser Ser His Ser Ser Gly Thr Leu Ser Ser Leu Glu
 50                  55                  60

Thr Val Ser Thr Gln Glu Leu Tyr Ser Ile Pro Glu Asp Gln Pro
 65                  70                  75                  80

Glu Asp Gln Glu Pro Glu Pro Thr Pro Ala Pro Trp Ala Arg Leu
                 85                  90                  95

Trp Ala Leu Gln Asp Gly Phe Ala Asn Leu Glu Thr Glu Ser Gly His
                100                 105                 110

Val Thr Gln Ser Asp Leu Glu Leu Leu Ser Ser Asp Pro Pro Ala
                115                 120                 125

Ser Ala Ser Gln Ser Ala Gly Ile Arg Gly Val Arg His His Pro Arg
130                 135                 140

Pro Val Cys Ser Leu Lys Cys Val Asn Asp Asn Tyr Trp Phe Gly Arg
145                 150                 155                 160

Asp Lys Ser Cys Glu Tyr Cys Phe Asp Glu Pro Leu Leu Lys Arg Thr
                165                 170                 175

Asp Lys Tyr Arg Thr Tyr Ser Lys Lys His Phe Arg Ile Phe Arg Glu
                180                 185                 190

Val Gly Pro Lys Asn Ser Tyr Ile Ala Tyr Ile Glu Asp His Ser Gly
                195                 200                 205

Asn Gly Thr Phe Val Asn Thr Glu Leu Val Gly Lys Gly Lys Arg Arg
210                 215                 220

Pro Leu Asn Asn Asn Ser Glu Ile Ala Leu Ser Leu Ser Arg Asn Lys
225                 230                 235                 240

Val Phe Val Phe Phe Asp Leu Thr Val Asp Asp Gln Ser Val Tyr Pro
                245                 250                 255

Lys Ala Leu Arg Asp Glu Tyr Ile Met Ser Lys Thr Leu Gly Ser Gly
                260                 265                 270

Ala Cys Gly Glu Val Lys Leu Ala Phe Glu Arg Lys Thr Cys Lys Lys
                275                 280                 285

Val Ala Ile Lys Ile Ile Ser Lys Arg Lys Phe Ala Ile Gly Ser Ala
290                 295                 300

Arg Glu Ala Asp Pro Ala Leu Asn Val Glu Thr Glu Ile Glu Ile Leu
305                 310                 315                 320

Lys Lys Leu Asn His Pro Cys Ile Ile Lys Ile Lys Asn Phe Phe Asp
                325                 330                 335

Ala Glu Asp Tyr Tyr Ile Val Leu Glu Leu Met Glu Gly Gly Glu Leu
                340                 345                 350

Phe Asp Lys Val Val Gly Asn Lys Arg Leu Lys Glu Ala Thr Cys Lys
                355                 360                 365

Leu Tyr Phe Tyr Gln Met Leu Leu Ala Val Gln Tyr Leu His Glu Asn
                370                 375                 380

Gly Ile Ile His Arg Asp Leu Lys Pro Glu Asn Val Leu Leu Ser Ser
385                 390                 395                 400

Gln Glu Glu Asp Cys Leu Ile Lys Ile Thr Asp Phe Gly His Ser Lys
                405                 410                 415

Ile Leu Gly Glu Thr Ser Leu Met Arg Thr Leu Cys Gly Thr Pro Thr
                420                 425                 430

Tyr Leu Ala Pro Glu Val Leu Val Ser Val Gly Thr Ala Gly Tyr Asn
                435                 440                 445

Arg Ala Val Asp Cys Trp Ser Leu Gly Val Ile Leu Phe Ile Cys Leu
450                 455                 460
```

```
Ser Gly Tyr Pro Pro Phe Ser Glu His Arg Thr Gln Val Ser Leu Lys
465                 470                 475                 480

Asp Gln Ile Thr Ser Gly Lys Tyr Asn Phe Ile Pro Glu Val Trp Ala
            485                 490                 495

Glu Val Ser Glu Lys Ala Leu Asp Leu Val Lys Lys Leu Leu Val Val
        500                 505                 510

Asp Pro Lys Ala Arg Phe Thr Thr Glu Glu Ala Leu Arg His Pro Trp
    515                 520                 525

Leu Gln Asp Glu Asp Met Lys Arg Lys Phe Gln Asp Leu Leu Ser Glu
530                 535                 540

Glu Asn Glu Ser Thr Ala Leu Pro Gln Val Leu Ala Gln Pro Ser Thr
545                 550                 555                 560

Ser Arg Lys Arg Pro Arg Glu Gly Glu Ala Glu Gly Ala Glu Thr Thr
                565                 570                 575

Lys Arg Pro Ala Val Cys Ala Ala Val Leu
                580                 585

<210> SEQ ID NO 3
<211> LENGTH: 2159
<212> TYPE: DNA
<213> ORGANISM: Homo sapiens

<400> SEQUENCE: 3
ttattacatc ctgcccttgt tctgttggta gagaggaatt cagcttcttc tggagcgcga      60
aagtcattca cgtttctctt gtgcataata gagctcgtaa actgtaggaa ttctgatgtg     120
cttcagtgca cagaacagta acagatgagc tgcttttggg gagagcttga gtactcagtc     180
ggagcatcat catggggtct agtgccacag agattgaaga attggaaaac accactttta     240
agtatcttac aggagaacag actgaaaaaa tgtggcagcg cctgaaagga atactaagat     300
gcttggtgaa gcagctggaa agaggtgatg ttaacgtcgt cgacttaaag aagaatattg     360
aatatgcggc atctgtgctg aagcagtttt atatcgatga acaagaaga cttctggata     420 ctgaagatga gctcagtgac attcagactg actcagtccc atctgaagtc cgggactggt     480
tggcttctac ctttacacgg aaaatgggga tgacaaaaaa gaaacctgag gaaaaaccaa     540
aatttcggag cattgtgcat gctgttcaag ctggaatttt tgtggaaaga atgtaccgaa     600
aaacatatca tatggttggt ttggcatatc agcagctgt catcgtaaca ttaaaggatg     660
ttgataaatg gtcttttcgat gtatttgccc taaatgaagc aagtggagag catagtctga     720
agtttatgat ttatgaactg tttaccagat atgatcttat caaccgtttc aagattcctg     780
tttcttgcct aatcacctt gcagaagctt tagaagttgg ttacagcaag tacaaaaatc     840
catatcacaa tttgattcat gcagctgatg tcactcaaac tgtgcattac ataatgcttc     900
atacaggtat catgcactgg ctcactgaac tggaattttt agcaatggtc tttgctgctg     960
ccattcatga ttatgagcat acagggacaa caaacaactt tcacattcag acaaggtcag    1020
atgttgccat tttgtataat gatcgctctg tccttgagaa tcaccacgtg agtgcagctt    1080
atcgacttat gcaagaagaa gaaatgaata tcttgataaa tttatccaaa gatgactgga    1140
gggatcttcg gaacctagtg attgaaatgg ttttatctac agacatgtca ggtcacttcc    1200
agcaaattaa aaatataaga aacagtttgc agcagcctga agggattgac agagccaaaa    1260
ccatgtccct gattctccac gcagcagaca tcagccaccc agccaaatcc tggaagctgc    1320
attatcggtg gaccatggcc ctaatggagg agttttttcct gcagggagat aaagaagctg    1380
```

```
aattagggct tccattttcc ccactttgtg atcggaagtc aaccatggtg gcccagtcac   1440
aaataggttt catcgatttc atagtagagc caacattttc tcttctgaca gactcaacag   1500
agaaaattgt tattcctctt atagaggaag cctcaaaagc cgaaacttct tcctatgtgg   1560
caagcagctc aaccaccatt gtggggttac acattgctga tgcactaaga cgatcaaata   1620
caaaaggctc catgagtgat gggtcctatt ccccagacta ctcccttgca gcagtggacc   1680
tgaagagttt caagaacaac ctggtggaca tcattcagca gaacaaagag aggtggaaag   1740
agttagctgc acaagaagca agaaccagtt cacagaagtg tgagtttatt catcagtaaa   1800
cacctttaag taaaacctcg tgcatggtgg cagctctaat ttgaccaaaa gacttggaga   1860
ttttgattat gcttgctgga aatctaccct gtcctgtgtg agacaggaaa tctattttg    1920 cagattgctc aataagcatc atgagccaca taaataacag ctgtaaactc cttaattcac   1980
cgggctcaac tgctaccgaa cagattcatc tagtggctac atcagcacct tgtgctttca   2040
gatatctgtt tcaatggcat tttgtggcat ttgtctttac cgagtgccaa taaattttct   2100
ttgagcagct aattgctaat tttgtcattt ctacaataaa gcttggtcca cctgttttc    2159
```

<210> SEQ ID NO 4
<211> LENGTH: 535
<212> TYPE: PRT
<213> ORGANISM: Homo sapiens

<400> SEQUENCE: 4

```
Met Gly Ser Ser Ala Thr Glu Ile Glu Glu Leu Glu Asn Thr Thr Phe
1               5                   10                  15

Lys Tyr Leu Thr Gly Glu Gln Thr Glu Lys Met Trp Gln Arg Leu Lys
            20                  25                  30

Gly Ile Leu Arg Cys Leu Val Lys Gln Leu Glu Arg Gly Asp Val Asn
        35                  40                  45

Val Val Asp Leu Lys Lys Asn Ile Glu Tyr Ala Ala Ser Val Leu Glu
    50                  55                  60

Ala Val Tyr Ile Asp Glu Thr Arg Arg Leu Leu Asp Thr Glu Asp Glu
65                  70                  75                  80

Leu Ser Asp Ile Gln Thr Asp Ser Val Pro Ser Glu Val Arg Asp Trp
                85                  90                  95

Leu Ala Ser Thr Phe Thr Arg Lys Met Gly Met Thr Lys Lys Lys Pro
            100                 105                 110

Glu Glu Lys Pro Lys Phe Arg Ser Ile Val His Ala Val Gln Ala Gly
        115                 120                 125

Ile Phe Val Glu Arg Met Tyr Arg Lys Thr Tyr His Met Val Gly Leu
    130                 135                 140

Ala Tyr Pro Ala Ala Val Ile Val Thr Leu Lys Asp Val Asp Lys Trp
145                 150                 155                 160

Ser Phe Asp Val Phe Ala Leu Asn Glu Ala Ser Gly Glu His Ser Leu
                165                 170                 175

Lys Phe Met Ile Tyr Glu Leu Phe Thr Arg Tyr Asp Leu Ile Asn Arg
            180                 185                 190

Phe Lys Ile Pro Val Ser Cys Leu Ile Thr Phe Ala Glu Ala Leu Glu
        195                 200                 205

Val Gly Tyr Ser Lys Tyr Lys Asn Pro Tyr His Asn Leu Ile His Ala
    210                 215                 220

Ala Asp Val Thr Gln Thr Val His Tyr Ile Met Leu His Thr Gly Ile
225                 230                 235                 240
```

```
Met His Trp Leu Thr Glu Leu Glu Ile Leu Ala Met Val Phe Ala Ala
            245                 250                 255

Ala Ile His Asp Tyr Glu His Thr Gly Thr Thr Asn Asn Phe His Ile
            260                 265                 270

Gln Thr Arg Ser Asp Val Ala Ile Leu Tyr Asn Asp Arg Ser Val Leu
            275                 280                 285

Glu Asn His His Val Ser Ala Ala Tyr Arg Leu Met Gln Glu Glu Glu
            290                 295                 300

Met Asn Ile Leu Ile Asn Leu Ser Lys Asp Asp Trp Arg Asp Leu Arg
305                 310                 315                 320

Asn Leu Val Ile Glu Met Val Leu Ser Thr Asp Met Ser Gly His Phe
                325                 330                 335

Gln Gln Ile Lys Asn Ile Arg Asn Ser Leu Gln Gln Pro Glu Gly Ile
            340                 345                 350

Asp Arg Ala Lys Thr Met Ser Leu Ile Leu His Ala Ala Asp Ile Ser
            355                 360                 365

His Pro Ala Lys Ser Trp Lys Leu His Tyr Arg Trp Thr Met Ala Leu
            370                 375                 380

Met Glu Glu Phe Phe Leu Gln Gly Asp Lys Glu Ala Glu Leu Gly Leu
385                 390                 395                 400

Pro Phe Ser Pro Leu Cys Asp Arg Lys Ser Thr Met Val Ala Gln Ser
                405                 410                 415

Gln Ile Gly Phe Ile Asp Phe Ile Val Glu Pro Thr Phe Ser Leu Leu
            420                 425                 430

Thr Asp Ser Thr Glu Lys Ile Val Ile Pro Leu Ile Glu Glu Ala Ser
            435                 440                 445

Lys Ala Glu Thr Ser Ser Tyr Val Ala Ser Ser Thr Thr Ile Val
            450                 455                 460

Gly Leu His Ile Ala Asp Ala Leu Arg Arg Ser Asn Thr Lys Gly Ser
465                 470                 475                 480

Met Ser Asp Gly Ser Tyr Ser Pro Asp Tyr Ser Leu Ala Ala Val Asp
                485                 490                 495

Leu Lys Ser Phe Lys Asn Asn Leu Val Asp Ile Ile Gln Gln Asn Lys
            500                 505                 510

Glu Arg Trp Lys Glu Leu Ala Ala Gln Glu Ala Arg Thr Ser Ser Gln
            515                 520                 525

Lys Cys Glu Phe Ile His Gln
            530                 535
```

CALMODULIN INHIBITORS FOR THE TREATMENT OF RIBOSOMAL DISORDERS AND RIBOSOMAPATHIES

CROSS REFERENCE TO RELATED APPLICATIONS

This application is a continuation application under 35 U.S.C. § 120 of U.S. Ser. No. 15/806,765, filed on Nov. 8, 2017, which is a continuation application under 35 U.S.C. § 120 of U.S. application Ser. No. 14/385,524 filed Sep. 16, 2014, which is a 35 U.S.C. § 371 National Phase Entry Application of International Application No. PCT/US2013/028969 filed Mar. 5, 2013, which designates the U.S., and which claims benefit, under 35 U.S.C. 119(e), of U.S. Provisional Patent Application Ser. No. 61/611,845 filed on Mar. 16, 2012, and 61/611,751, filed on Mar. 16, 2012, the contents of all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 2, 2017, is named 701039-073663-US_SL.txt and is 15,683 bytes in size.

GOVERNMENT SUPPORT

This invention was made with government support under Grant Number HL01001 awarded by the National Institutes of Health. The Government has certain rights in the invention.

FIELD OF THE INVENTION

The present invention relates generally to methods, compositions and kits for treatment of ribosomal disorders and ribosomopathies, e.g. Diamond Blackfan aanemia (DBA). In some embodiments, the invention relates to the use of calmodulin inhibitors and calcium channel blockers for treatment of ribosomal disorders and ribosomopathies, e.g. Diamond Blackfan anemia(DBA).

BACKGROUND OF THE INVENTION

Diamond Blackfan anemia (DBA) is a congenital anemia that presents in children, often before one year of age (Vlachos et al., 2008). The primary symptom for these patients is a block in erythroid differentiation and possible defect in hematapoietic stem cells (HSCs), and some patients also have craniofacial anomalies. Ribosomal protein S19 (RPS19) was the first gene found mutated in DBA patients (Draptchinskaia et al., 1999). Sequencing of patient samples has identified mutations of either large (60s) or small (40s) subunit ribosomal proteins in over 50% of patients (Vlachos et al., 2010), most recently rps29. Patients are heterozygous for these mutations, always maintaining a wildtype copy of the affected ribosomal protein gene.

Ribosomal protein knockdown leads to an increase of free ribosomal proteins. Some ribosomal proteins, including RPL11 and RPLS, can prevent p53 degradation, as they are able to bind MDM2 and sequester it from p53 (Fumagalli et al, 2009). RPL26 has been shown to increase p53 protein by an alternative mechanism, as it can bind p53 mRNA, increasing its translation (Tagaki et al., 2005). p53 activation plays an important role in DBA pathogenesis, as well as in other diseases where ribosomal and related genes are mutated, now termed ribosomopathies. These include 5q-myelodysplastic syndrome, where one copy of RPS14 is lost. p53 activation is also a common feature in bone marrow failure disorders, such as Fanconi Anemia (Ceccaldi et al., 2012). In human CD34+ cells, RPS19 knockdown leads to p53 activation (Ebert et al., 2005; Flygare et al., 2005), with increased accumulation in erythroid cells. Differentiation defects can be rescued by p53 inhibition (Dutt et al., 2011). Mouse models of RPS19 mutation or knockdown have hematopoietic defects that can be rescued by p53 mutation (McGowan et al., 2008; Jaako et al., 2011). Rps19 has been targeted by morpholino in zebrafish embryos, and the hematopoietic defects in rpl11 mutant zebrafish are rescued by p53 knockdown (Danilova et al., 2008; Torihara et al., 2011; Danilova et al., 2011).

Ribosomal protein mutations are common in patients with Diamond Blackfan anemia (DBA), who have red cell aplasia and craniofacial abnormalities. The inventors have previously characterized zebrafish mutant rps29, a ribosomal protein in the small subunit, that have hematopoietic and endothelial defects (Taylor et al., 2012). Rps29−/−embryos have morphological defects in the head, as well as decreased hematopoietic stem cells, hemoglobin, and staining of endothelial markers. Consistent with other models of DBA, knockdown of p53 near completely rescues the rps29 mutant phenotype.

The inventors demonstrated that Rps29−/−embryos have a defect in arterial specification, leading to decreased HSCs and decreased flk1 expression in the intersegmental vessels at 24 hours post fertilization (hpf). Primitive erythropoiesis is also affected, as rps29−/−embryos have less hemoglobin. These embryos also have increased apoptosis, particularly in the head, and die by five days post fertilization (dpf). p53 pathways are activated in the embryo, and p53 mutation rescues all hematopoietic and apoptotic phenotypes.

The current treatment options for diseases associated with a ribosomal disorder or ribosomopathy, e.g., a mutation in a ribosomal protein are far from optimal, especially for Diamond Blackfan anemia (DBA). As such, it is imperative to discover novel, effective, and targeted therapies for these diseases associated with a ribosomal disorder or ribosomopathy, e.g., a mutation in a ribosomal protein. In particular, there is a strong need in the art for improved methods for treatment of DBA with small-molecule drugs.

SUMMARY OF THE INVENTION

The present invention is generally directed to methods, compositions and kits for treatment of ribosomal disorders and ribosomapathies, e.g. Diamond Blackfan anemia (DBA). In some embodiments, the invention relates to the use of calmodulin inhibitors and calcium channel blockers for treatment of ribosomal disorders and ribosomapathies, e.g. Diamond Blackfan anemia (DBA).

In particular, the present invention is based upon the discovery that calmodulin inhibitors and calcium channel blockers can be used to treat ribosomal disorders and ribosomapathies in subjects, for example, e.g. human subjects with Diamond Blackfan anemia (DBA). The inventors have discovered that the calmodulin (CaM) inhibitors and calcium channel blockers rescued morphological defects and hematopoietic and endothelial defects in rps29−/−zebrafish embryos, an in vivo model of ribosomal protein defect, and also rescued rps19 knockdown in CD34+ differentiated, as well as decreased p21+ and p53 levels back to normal. Therefore, the calmodulin inhibitors and calcium channel blockers as disclosed herein can be used in a method for treatment of subjects with ribosomal protein disorders or ribosomopathies, e.g. Diamond Blackfan anemia (DBA) and other ribosomopathies, such as myelodysplasia, including 5q-myelodysplasia, Shwachman-Diamond syndrome and Treacher Collins Syndrome in human subjects.

In an effort to identify pathways that could rescue ribosomal protein mutant defects, the inventors performed a chemical screen on zebrafish with mutations in the rps29 ribosomal protein (rps29$^{-/-}$ embryos). After screening 600 compounds, the inventors discovered that calmodulin inhibitors rescued mutant phenotypes, such as morphological, endothelial, and hemoglobin phenotypes, including flk1 expression and returning to normal hemoglobin levels. The inventors demonstrated that the calmodulin inhibitors had an effect on the DBA phenotype in in vitro models where shRNA knockdown of RPS19 has been shown to stabilize p53 and induce p21. Importantly, the inventors demonstrated that inhibition of calmodulin leads to a decrease in p21 protein levels and inhibits nuclear localization of both p53 and p21. The inventors also demonstrated that calmodulin inhibitors could decrease p21 and inhibit nuclear localization of p53 and p21 in primary cord blood-derived CD34$^+$ hematopoietic stem and progenitor cells, demonstrating that calmodulin inhibitors function well in the blood. Accordingly, the inventors demonstrate herein that the calmodulin pathway is important in p53 regulation, and small molecules that inhibit calmodulin may be effective therapies for patients with ribosomal deficiency, and for the treatment of patients with DBA.

In particular, in an in vivo chemical screen to screen to rescue rps29-/-embryos with morphological defects, the inventors identified calmodulin inhibitors that rescued morphological, endothelial and hemoglobin phenotypes. The calmodulin inhibitors were demonstrated to increase flk expression and hemoglobin levels, and 15 compounds were validated to rescue flk expression, 1 compound validated to rescue head morphological defects. In particular, the inventors discovered that the following napthalenesulfonamide compounds are useful in the treatment of ribosomal disorders; W-7 rescued flk expression; A-7 rescued vascular defects; W-5 rescued vascular defects; A-3 rescued head morphology (A-3 is a structural derivative of A-7). The inventors also assessed other calmodulin inhibitors, such as CGS-9343B and members of phenothiazine family; such as trifluoperazine (TFP), as well as Ca$^{2+}$ channel blockers nimodipine and YS-035, which were demonstrated to rescue vascular defects. Vinpocetine (inhibitor of calmodulin-dependent phosphodiesterase I (pde 1)) was also discovered to be useful in the treatment of ribosomal disorders. W-7 and A-3 both rescue hemoglobin levels in the zebrafish embryo.

In an in vitro model of primary blood derived CD34+ hematopoietic stem and progenitor cells, which had rps19 knockdown by siRNA, calmodulin inhibitors A-3 rescued rps19 knockdown and decreased p53 and p21 levels or nuclear localization. Accordingly, the inventors have demonstrated herein that calmodulin inhibitors, as well as calcium channel blockers,inhibitors of calmodulin-dependent PDE1, or inhibitors of calmodulin-dependent checkpoint kinases, and can be used to mediate p53 activation upon ribosomal protein knockdown, thereby rescuing effects of ribosomal deficiency and treating ribosomal deficiency disorders, such as DBA.

Accordingly, one aspect of the present invention relates to method of treating a subject with a ribosomal disorder or ribosomopathy, comprising administering an effective amount of a calmodulin inhibitor to the subject to decrease p53 or p21 in at least one of CD34+ cells, erythroid cells or erythroid differentiated cells in the subject.

In some embodiments of all aspects of the present invention, a calmodulin inhibitor is a phenothiazine compound, for example, trifluoperazine (TFP), or flurphenazine, or perphenazine or a derivative or analogue thereof In some embodiments of all aspects of the present invention, a calmodulin inhibitor is a naphthalenesulfonamide compound, for example but not limited to, A-3, W-7 (N-(6-Aminohexyl) -5-chloro-1-naphthalenesulfonamide hydrochloride), A-7, W-5, or a derivative or an thereof.

In some embodiments of all aspects of the present invention, a calmodulin inhibitor is CGS-9343 (zaldaride maleate), or a derivative or an analogue thereof.

In some embodiments, the method encompasses treating a subject with a ribosomal disorder or ribosomopathy, comprising administering an effective amount of a calcium channel blocker or a calmodulin inhibitor to the subject to decrease p53 or p21 in at least one of CD34+ cells, erythroid cells or erythroid differentiated cells in the subject, where the calmodulin inhibitor or calcium channel blocker or selected from the group consisting of: nimodipine, YS-035, bepridil, bepridil-hydrochloride, phenoxybenzamine, cetiedil, chlorpromazine, promazine, desipramine, flunarizine, or promethazine In some embodiments, a calmodulin inhibitor is an inhibitor of Chk2, for example, but not limited to BML-22.

In some embodiments of all aspects of the present invention, a calmodulin inhibitor is a calmodulin dependent phosphodiesterase 1 (pde 1) inhibitor, for example, but not limited to vinpocetine.

In some embodiments of all aspects of the present invention, the method comprises treating a subject with a ribosomal disorder has Diamond Blackfan Anemia (DBA) or inherited erythroblastopenia, for example, where the subject has DBA1, DBA2, DBA3, DBA4, DBA5, DBA6, DBA7, or DBA8. In some embodiments, a subject with a ribosomal disorder has a mutation in ribosomal protein 19 (RPS19). In alternative embodiments, a subject with a ribosomal disorder has a mutation in ribosomal protein from at least one of, but not limited to RPS7, RPS10, RPS19, RPS24, PRS26, RPS17, PRS27L RPS29. RPL35A, PRLS and PPL11.

In some embodiments, a subject with a ribosomal disorder has a mutation in a ribosomal protein selected from the group consisting of: rPL2A, rPL2B, rPL3, rpL4A, rPL4B, rPL7A, rPL7B, rPL10, rPL11, rPL16A, rPL17A, rPL17B, rPL18A, rPL18B, Rp119A, rPL19, rPL25, rPL29, rpL31A, rpL31B, rPL36A, rPL40A, rPS1A, rPS6A, rPS6B, rPS14A, rPS15, rPS19, rPS23B, rPS25A, rPS26B, rPS29, rPS29B and rPS31.

In some embodiments of all aspects of the present invention, the method further comprises administering another therapeutic agent to treat the ribosomal protein defect, selected from the group consisting of: corticosteroids, blood transfusions and other treatments known to persons of ordinary skill in the art.

In some embodiments of all aspects of the present invention, a calmodulin inhibitor or calcium channel blocker administered to the subject increases the number of CD71+ erythroid cells in the subject and/or increases hemoglobin levels in the subject.

In some embodiments of all aspects of the present invention, the methods and calmodulin inhibitors and calcium channel blockers as disclosed herein can be used to treat a subject with a ribosomal disorder, such as DBA has a symptom of macrocytic anemia and/or craniofacial abnormalities.

In some embodiments of all aspects of the present invention, the methods and calmodulin inhibitors and calcium channel blockers as disclosed herein can be used to treat a subject with a ribosomopathy such as 5q-myelodysplasia, for example, where the subject has a mutation in Rps14 or decrease in Rps14 expression. In some embodiments, a subject with 5q-myelodysplasia has dysplastic bone marrow.

In some embodiments of all aspects of the present invention, the methods and calmodulin inhibitors and calcium channel blockers as disclosed herein can be used to treat a subject with a ribosomopathy such as Shwachman-Diamond syndrome, for example, where the subject has a mutation in Sbds. In some embodiments, a subject with Shwachman-Diamond syndrome has one or more symptoms selected from pancreatic insufficiency, bone marrow dysfunction, skeletal deformities.

In some embodiments of all aspects of the present invention, the methods and calmodulin inhibitors and calcium channel blockers as disclosed herein can be used to treat a subject with a ribosomopathy such as Treacher Collins Syndrome, for example, where the subject has a mutation in TCOF1 (nucleolar). In some embodiments, a subject with Treacher Collins Syndrome has one or more craniofacial deformities.

In some embodiments the present invention also provides kits comprising compositions comprising the calmodulin inhibitors and/or calcium channel blockers as disclosed herein for the use in the methods to treat a subject with a ribosomal protein disorder or disease or ribosomopathy as disclosed herein.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A is a schematic diagram of chemical screen. FIGS. 1B and 1C show whole mount in situ hybridization (ISH) for flk1 at 24 hours post fertilization 24 hpf).

FIG. 2A shows brightfield image of chemically treated embryo at 24 hpf showing head morphology at 24 hpf. FIG. 2B shows the chemical structures of W-7 and A-3. FIG. 2C shows benzidine staining for hemaglobin levels at 40 hpf.

FIGS. 3A-3F show calmodulin inhibition decreases p21 upon rps19 knockdown in A549 cells. FIGS. 3A-3D show p53 and p21 levels, as determined by FACS, in A549 cells with shRNA targeting luciferase or rps19 and treated with A-3 or trifluoperazine (TFP). FIGS. 3E and 3F show p53 and p21 levels, as determined by FACS, in a timecourse of A-3 treatment.

FIG. 4A shows immunofluorescence staining for p53 and p21 was performed in A549 cells. FIG. 4B shows imageJ quantification of the ratio of the nuclear:cytoplasmic intensity of p53 (top panel) and p21 (lower panel) in A549 cells nuclear extracts. FIG. 4C shows flow cytometry for annexin and propidium iodide in A549 cells. Data displayed as percent of total. FIG. 4D shows cell cycle status was ascertained by flow cytometry in fixed A549 cells incubated in propidium iodide.

FIG. 5A shows A-3 decreases p21 in $CD34^+$ cells in erythroid proliferation media, as measured by FACS. FIG. 5B shows A-3 decreases p21 in $CD34^+$ cells in erythroid proliferation media, as measured by FACS.

FIG. 6A is a schematic of the in vitro erythroid differentiation assay. FIG. 6B shows p21 RNA expression as measured by quantitative PCR, showing TFP reduces p21 mRNA levels in rps19 knocked down cells (erythroid cells which have been treated with rps19 shRNA). FIG. 6C shows the percentage of CD71 positive (CD71+) cells as measured by flow cytometry, demonstrating that with increasing TFP concentration, the percent of CD71+ cells in a population of erythroid cells with rsp19 knockdown return to normal levels (e.g., the percent of CD71+ cells in a population of erythroid cells that have normal levels of rsp19, e.g., Luc control).

DETAILED DESCRIPTION OF THE INVENTION

Figure 1A:
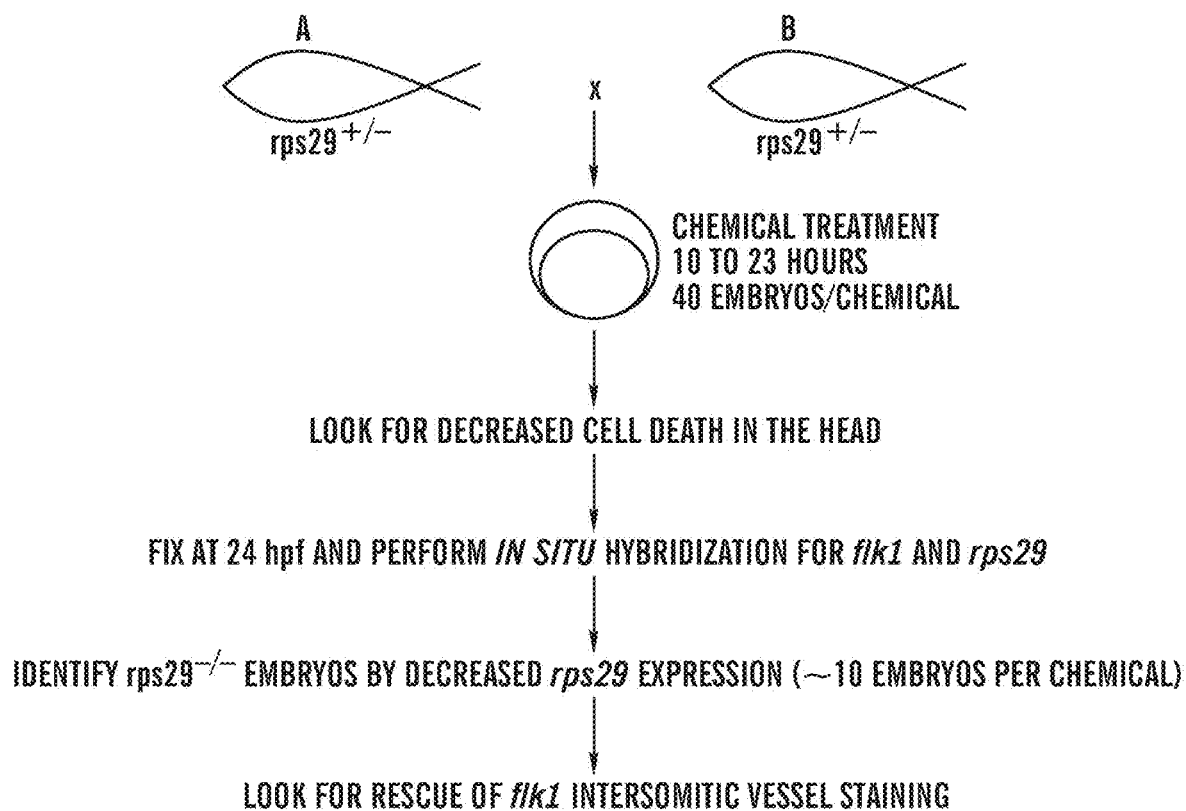
FIGS. 1A-1C show treatment with calmodulin inhibitors rescues phenotypes and vascular defect in in zebrafish rps29−/− embryos.

In some embodiments, the present invention is based upon the discovery that calmodulin inhibitors and calcium channel blockers can be used to treat ribosomal disorders and ribosomapathies in subjects, for example, e.g. human subjects with Diamond Blackfan anemia (DBA). The inventors have discovered that the calmodulin (CaM) inhibitors and calcium channel blockers rescued morphological defects and hematopoietic and endothelial defects in rps29−/− zebrafish embryos, an in vivo model of ribosomal protein defect, and also rescued rps19 knockdown in CD34+ differentiated cells, as well as decreased p21 levels back to normal. Therefore, the calmodulin inhibitors and calcium channel blockers as disclosed herein can be used in a method for treatment of subjects with ribosomal protein disorders or ribosomopathies, e.g. Diamond Blackfan anemia (DBA) and other ribosomopathies, such as myelodysplasia, including 5q-myelodysplasia, Shwachman-Diamond syndrome and Treacher Collins Syndrome in human subjects.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Definitions

The term "regulate" used herein in reference to expression of a gene, refers to producing an effect on, for example, gene expression. In some embodiments, the effect can be stimulatory, such as increasing expression of a gene. In some embodiments, the effect can be inhibitory, such as decreasing expression of a gene. The terms "regulate" and "modulate" are interchangeably used herein.

The terms "calmodulin inhibitor" used interchangeably herein, generally refers to an agent or molecule that inhibits the activity or expression of calmodulin. Calmodulin inhibitors can be of synthetic or biological origins. They can be organic, or inorganic molecules, or peptides, antibodies or antisense RNA that inhibit calmodulin. Inhibitors of calmodulin of the invention are chemical entities or molecules that can inhibit expression of calmodulin and/or biological activity of calmodulin, as disclosed herein, for example, compounds of trifluroperazine (TFP), flurophenazine, perphenazine, and naphthalenesulfonamides, and enantiomers, prodrugs, derivatives and pharmaceutically acceptable salts thereof, which are discussed further in the section The term "ribosomal protein", are also referred to herein as "r-proteins" refers to any of the intracellular ribonucleoprotein particles concerned with protein synthesis; they consist of reversibly dissociable units and are found either bound to cell membranes or free in the cytoplasm. They may occur singly or occur in clusters (polyribosomes). They may occur singly or in clusters, called polyribosomes or polysomes, which are ribosomes linked by mRNA and are actively engaged in protein synthesis. Ribonucleoproteins (often referred to as "RNPs") are important in protein synthesis; they consist of two, one large (L) and one small (S), reversibly dissociable units (called also 60S and 40S subunits in eukaryotes (50S and 30S in bacteria)). The term includes any of the proteins that, in conjunction with rRNA, make up the ribosomal subunits involved in the cellular process of translation. The term encompasses proteins of the small (S) subunit and the large (L) subunit of the ribosomes. Due to the high conservation of both the RNA and proteins moieties of ribosomes and of the ribosome biogenesis machinery from yeast and bacteria, a large part of the knowledge about these organic molecules has come from the study of $E.$ $coli$ ribosomes, and also applies to humans. In the small (30S) subunit of $E.$ $coli$ ribosomes, the proteins denoted S4, S7, S8, S15, S17, S20 bind independently to 16S rRNA. After assembly of these primary binding proteins, S5, S6, S9, S12, S13, S16, S18, and S19 bind to the growing ribosome. These proteins also potentiate the addition of S2, S3, S10, S11, S14, and S21. Protein binding to helical junctions is important for initiating the correct tertiary fold of RNA and to organize the overall structure. Nearly all the proteins contain one or more globular domains. Moreover, nearly all contain long extensions that can contact the RNA in far-reaching regions. Additional stabilization results from the proteins' basic residues, as these neutralize the charge repulsion of the RNA backbone. Protein-protein interactions also exist to hold structure together by electrostatic and hydrogen bonding interactions. Theoretical investigations pointed to correlated effects of protein-binding onto binding affinities during the assembly process [2]

The term "ribosomal disorder" or "ribosomal protein disorder" refers to a disease or disorder linked to a mutated and/or abnormal function of a ribosome protein. It can include a disease due to mutation in a ribosomal protein, or a disease due to a decreased level, or partial loss of function, of a ribosomal protein, or alternatively, a disease due to an increased level of a ribosomal protein, as compared to a normal healthy control subject. The term ribosomal disorder includes genetic diseases of ribosomal proteins, including but not limited to, Diamond Blackfan anemia (DBA), myelodysplasia, Shwachman-Diamond Syndrome (SDS) and Treachers Collins Syndrome (TCS).

The term "ribosomopathy" or "ribosomopathies" refers to any disease or malfunction of ribosomes. Ribosomes are small organelles found in all cells which are involved in the production of proteins by translating messenger RNA. A disease or malfunction of ribosomes include (i) disease of ribosomal biogenesis proteins, (ii) disease of small nucleolar ribonuceloproteins, and (iii) diseases of ribosomal proteins (as discussed above in the definition of "ribosomal protein disorder"), and are all reviewed in Freed et al., Mol. Biosyst. 2010; 6(3); 481-493 entitled "When ribosomes go bad: diseases of ribosome biogenesis", which is incorporated herein in its entirety by reference. Diseases of ribosomal biogenesis proteins include, but are not limited to Treachers Collins syndrome (TCS), male infertility due to a mutation inUTP14c, native American indian childhood cirrhosis (NAIC), Bowen-Conradi syndrome (BCS), alopecia neurological defect and endrocrinopathy syndrome (ANE syndrome), shwachman-dimaond syndrome (SDS), candidate gene for primary open angle glaucoma (POAG), and modifier of neurofibromatosis type I (NF1). Diseases of small nucleolar ribonuceloproteins include, but are not limited to, Anauxetic dysplasia (AD), cartilage-hair dysplasia (also called metaphyseal chondrodysplaia, McKusick type; CCH), metaphyseal dysplasia without hypotrichosis (MDWH), Dyskeratosis congenita (also called Zinzzer-Engman-Cole syndrome), Hoyeraal-Hreidarsson syndrome (where some cases are severe variants of Dyskeratosis congenita), and Prader-Willi syndrome (PWS)

The term "derivative" as used herein refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

The term "functional derivative" and "mimetic" are used interchangeably herein, and refers to compounds which possess a biological activity (in particular functional biological activity) that is substantially similar to the biological activity of the entity or molecule for which it's a functional derivative of The term functional derivative is intended to include the fragments, variants, analogues or chemical derivatives of a molecule. In certain embodiments, functional derivatives and functional analogues of calmodulin inhibitors (e.g., functional analogues of TFP, A-3, W-7, A-7, W-5 and CGS-9343) can be assessed for their biological activity using the assay as disclosed herein, where derivatives and analogues which inhibit calmodulin would be considered as functional derivatives or functional analogues of such calmodulin inhibitors.

The term "analog" as used herein refers to an agent that retains the same, or a substantially similar biological function (i.e., inhibition of calmodulin) and/or structure as the molecule or chemical or polypeptide it is an analogue of Examples of analogs include peptidomimetics (a peptide analog), peptide nucleic acids (a nucleic acid analog), small and large organic or inorganic compounds, as well as derivatives and variants of a polypeptide or nucleic acid herein.

The term "substantially similar", when used to define the biological activity of a derivative or analogue of a calmodulin inhibitor as compared to the biological activity of the calmodulin inhibitor to which it is a derivative or analogue of, means that a particular derivative or analogue differs from the initial calmodulin inhibitor in chemical structure, by one or more groups or elements, including substitutions, deletions, or additions of groups of elements, the net effect of which is to retain at least some of the biological activity found in the initial calmodulin inhibitor with respect to inhibition of calmodulin activity and/or expression. Such biological activity of inhibition of calmodulin by a functional derivative or analogue of can be assessed by one of ordinary skill in the art using assays well known in the art, for example, inhibition of calmodulin may, inter alia, be determined in the following in vitro assay, which measured the calmodulin-dependent activation of myosin light chain kinase (MLCK). Activated MLCK phosphorylates chicken gizzard myosin light chain. If calmodulin is inhibited the rate of myosin light chain phosphorylation is reduced. To test this, the following experiment is carried out (according to Itoh et al. Biochem. Pharm. 1986,35:217-220). The reaction mixture (0.2 ml) contains 20 mM Tris-HCl (pH 7.5), 0.05 mM [γ-32P] ATP (1 μCi/assay tube), 5 mM MgCl2,10 μM myosin light chain, 24 nM calmodulin and 0.1 mM $CaCl_2$. MLCK (specific activity: 4.5 moles/min/mg) concentration from chicken gizzard is 0.1 μg/ml. The incubation is carried out at 30° C. for 4 min. The reaction is terminated by addition of 1 ml of 20% trichloroacetic acid. Then 0.1 ml of bovine serum albumin (1 mg/ml) is added to the reaction mixture. The sample is then centrifuged at 200 Og for 10 min, the pellet is resuspended in 5% trichloroacetic acid. The final pellet is dissolved in 2 ml of 1 N NaOH and the radioactivity measured in a liquid scintillation counter. Trypsin-treated MLCK can be prerared as described in Itoh et al. J Pharmacol. Exp. Ther. 1984,230, p 737. The reaction is initiated by the addition of the ATP and is carried out in the presence of the potential inhibitors or—as a control—in the presence of their solvent. Different concentrations of the compounds will be tested in the above assay. The concentration of the compound which results in 50% decrease of kinase activity will be the IC50 concentration.

An alternative method to assay a compound, e.g., an analogue or derivative of a calmodulin inhibitor as disclosed herein for inhibition of calmodulin is a standard assay assessing cAMP levels as described in Inagaki et al., 1986 "Napthalenesulfonamides as Calmodulin Antagonists and Protein Kinase Inhibitors", which is incorporated herein by reference in its entirety. Alternatively, commercially available kits to measure cAMP levels can be used, for example, available from Sigma. Cell Signaling, eenzyme.com, biovision and the like.

In some embodiments, a method to measure the inhibition of calmodulin is a modified method from Kahn et al. Cell 1998, 92:809-818: As a read-out the inhibition of Gonadotropin-releasing hormone (GnRH) induced ERK Phosphorylation in αT3-1 cells as measured. αT3-1 cells are serum-starved for 2 h, pretreated with control solvent or increasing concentrations of the compounds to be tested for 30 min. Then GnRH is administered for 60 min. Cell lysates are prepared and resolved by SDS-PAGE. Western blot analysis is used to determine the phosphorylation status of ERKs using a phospho-specific antibody (cell signaling technologies). As a control, total ERK2 will also be determined using an ERK specific antibody (Santa Cruz Biotech). Western-Blot fluorescence of phospho-ERK and total ERK2 will be quantified. The ratio of phospho-ERK/total ERK2 will be plotted against the concentration of the compound to be tested. The estimated concentration, at which a 50% reduction of ERK phosphorylation (rel. to total ERK2) occurs, can be used as the IC50 value for this compound.

The term "tissue" is intended to include intact cells, blood, blood preparations such as plasma and serum, bones, joints, muscles, smooth muscles, and organs.

The term "subject" includes human and other mammalian subjects that receive either prophylactic or therapeutic treatment. The term "subject" and "individual" are used interchangeably herein, and refer to an animal, for example a human, to whom treatment, including prophylactic treatment, with the cells according to the present invention, is provided. The "non-human animals" of the invention include mammals such as rats, mice, rabbits, sheep, cats, dogs, cows, pigs, and non-human primates.

The terms "a reference sample" or "a reference level" as used interchangeably herein refer to a negative control of the condition. For example, in the context of treatment, a reference level is the level if a subject is not treated. In some embodiments, a reference level in the context of diagnosis is the level present in a normal healthy subject. The term "normal healthy subject" refers to a subject who has no symptoms of any diseases or disorders, or who is not identified with any diseases or disorders, or who is not on any medication treatment, or a subject who is identified as healthy by physicians based on medical examinations. In some embodiments, a reference level or sample used herein refers to the level measured at a previous time point from a subject being treated.

The terms "treat", "treatment" and "treating" used interchangeably, with respect to treatment of a disease or disorder, mean preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis in a subject who is at risk of the disease, as well as slowing or reducing progression of existing disease. The term treating encompasses reducing or alleviating at least one adverse effect or symptom of a condition, disease or disorder associated with inappropriate ribosomal protein function. As used herein with respect to a ribosomal protein disorder, the term treating is used to refer to the reduction of a symptom and/or a biochemical marker of a ribosomal protein disorder by at least 10%, for example a reduction of p21 and/or p53 levels in CD34+ cells in the subject, or a return of hemoglobin back to normal levels, or a restoration or prevention of craniofacial deformities. For example but are not limited to, a reduction of p21 and/or p53 levels in CD34+ cells in the subject, as an illustrative example only, by 10%, would be considered effective treatments by the methods as disclosed herein.

As used herein, the term "treating" includes preventing the progression and/or reducing or reversing at least one adverse effect or symptom of a condition, disease or disorder associated with a ribosomal protein disorder or ribosomopathy, for example, DBA. Accordingly, in some embodiments, treatment can be prophylactic in terms of completely or partially preventing a disease or sign or symptom of a ribosomal protein disorder or ribosomopathy. For example, subjects known to have a mutation in ribosomal protein or alternatively, low expression levels of a specific ribosomal protein, can be subjected to prophylactic treatment to prevent the onset of one or more symptoms associated with such a mutation in the ribosomal protein, and/or decreased levels in the ribosomal protein. In some embodiments, prophylactic treatment can be administered to subjects who had prior treatment of a disease associated with a ribosomal protein disorder. For example, for subjects who have received corticosteroids or blood transfusions for the treatment of DBA and/or other previous treatment to stabilize their DBA can be prophylactically treated (e.g. with a calmodulin inhibitor and/or calcium channel blocker as disclosed herein).

As used herein, the terms "prevent," "preventing" and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the complete avoidance or prevention of symptoms or markers, but also a reduced severity or degree of any one of those symptoms or markers, relative to those symptoms or markers arising in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

The term "prophylactic" or "therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

As used herein, "gene silencing" or "gene silenced" in reference to an activity of an RNAi molecule, for example a siRNA or miRNA refers to a decrease in the mRNA level in a cell for a target gene (e.g. Chk2 and/or PDE1 and/or CAM1 gene) by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene. By way of an example only, in some embodiments RNAi agents which serve to inhibit or gene silence are useful in the methods, kits and compositions disclosed herein to inhibit a IGPR-1 gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "gene product(s)" as used herein refers to include RNA transcribed from a gene, or a polypeptide encoded by a gene or translated from RNA.

The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease" or "inhibition" is used in the context of the level of expression or activity of a gene or a protein, e.g. calmodulin, it refers to a reduction in protein or nucleic acid level or activity in a cell, a cell extract, or a cell supernatant. For example, such a decrease may be due to reduced RNA stability, transcription, or translation, increased protein degradation, or RNA interference. In some embodiments, a calmodulin inhibitor which is a small-molecule as disclosed herein can decrease the activity or expression of calmodulin. Preferably, this decrease is at least about 5%, at least about 10%, at least about 25%, at least about 50%, at least about 75%, at least about 80%, or even at least about 90% of the level of expression or activity under control conditions. The term "level" as used herein in reference to calmodulin refers to expression or activity of camodulin.

The terms "up-regulate", "increase" or "activate" are all used herein to generally mean an increase by a staticaly significant amount; for the avoidance of any doubt, the terms "up-regulate", "increase" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or a 100% increase or more, or any increase between 10-100% as compared to a reference level, or an increase greater than 100%, for example, an increase at least about a 2-fold, or at least about a 3-fold, or at least about a 4-fold, or at least about a 5-fold or at least about a 10-fold increase, or any increase between 2-fold and 10-fold or greater as compared to a reference level. When "increase" is used in the context of the expression or activity of a gene or protein, it refers to a positive change in protein or nucleic acid level or activity in a cell, a cell extract, or a cell supernatant. For example, such an increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

The terms "significantly different than,", "statistically significant," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

A "pharmaceutical composition" refers to a chemical or biological composition suitable for administration to a mammalian subject. Such compositions may be specifically formulated for administration via one or more of a number of routes, including but not limited to, oral, parenteral, intravenous, intraarterial, subcutaneous, intranasal, sublingual, intraspinal, intracerebroventricular, and the like.

The term "effective amount" is used interchangeably with the term "therapeutically effective amount" and refers to the amount of at least one agent, e.g., calmodulin inhibitor and/or calcium channel blocker of a pharmaceutical composition, at dosages and for periods of time necessary to achieve the desired therapeutic result, for example, to reduce or stop at least one symptom of the ribosomal disorder or ribosomopathy, for example a symptom of high levels of p53 and/or p21 in CD34+ cells in the subject. For example, an effective amount using the methods as disclosed herein would be considered as the amount sufficient to reduce a symptom of the ribosomal disorder or ribosomopathy by at least 10%. An effective amount as used herein would also include an amount sufficient to prevent or delay the development of a symptom of the disease, alter the course of a symptom disease (for example but not limited to, slow the progression of a symptom of the disease), or reverse a symptom of the disease. Accordingly, the term "effective amount" or "therapeutically effective amount" as used herein refers to the amount of therapeutic agent (e.g. at least one calmodulin inhibitor as disclosed herein) of pharmaceutical composition to alleviate at least one symptom of a ribosomal disorder or ribosomopathy, e.g. DBA. Stated another way, "therapeutically effective amount" of a calmodulin inhibitor and/or a calcium channel blocker as disclosed herein is the amount of a calmodulin inhibitor or calcium channel blocker which exerts a beneficial effect on, for example, the symptoms of the ribosomal disorder or ribosomopathy. The dosage administered, as single or multiple doses, to an individual will vary depending upon a variety of factors, including pharmacokinetic properties of the calmodulin inhibitor, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify the a calmodulin inhibitor as disclosed herein which will achieve the goal of reduction in the severity of at least one symptom of a ribosomal protein disease or disorder or ribosomopathy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

The terms "administered" and "subjected" are used interchangeably in the context of treatment of a disease or disorder. Both terms refer to a subject being treated with an effective dose of pharmaceutical composition comprising a calmodulin inhibitor of the invention by methods of administration such as parenteral or systemic administration.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of a pharmaceutical composition comprising at least a calmodulin inhibitor as disclosed herein such that it enters the animal's system and, thus, is subject to metabolism and other like processes, for example, subcutaneous administration.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "optional" or "optionally" means that the subsequent described event, circumstance or substituent may or may not occur, and that the description includes instances where the event or circumstance occurs and instances where it does not.

The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a pharmaceutical composition comprising "an agent" includes reference to two or more agents.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of elements that do not materially affect the basic and novel or functional characteristic(s) of that embodiment of the invention.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean ±1%. The present invention is further explained in detail by the following, including the Examples, but the scope of the invention should not be limited thereto.

This invention is further illustrated by the examples which should not be construed as limiting. The contents of all references cited throughout this application, as well as the figures and tables are incorporated herein by reference. All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Calmodulin Inhibitors

The present invention relates in part to methods and compositions to inhibit calmodulin. In some embodiments, calmodulin inhibitors as disclosed herein can be used to inhibit the cellular calmodulin activity. In some embodiments, calmodulin inhibitors as disclosed herein can decrease expression (level) of calmodulin. In some embodiments, the calmodulin inhibitors inhibit an enzyme which is dependent on calmodulin for its activity. For example, the term calmodulin inhibitor encompasses an inhibitor of calmodulin-dependent phosphodiesterase 1 (PDE 1), or an inhibitor of the calmodulin-dependent kinase chk2. In some embodiments, the term calmodulin inhibitor encompasses an inhibitor of a calmodulin dependent calcium channel The ability of a compound to inhibit calmodulin can be assessed by measuring a decrease in activity of calmodulin as compared to the activity of calmodulin in the absence of a calmodulin inhibitor. In some embodiments, the ability of a compound to inhibit calmodulin can be assessed by measuring a decrease in the biological activity, e.g., calmodulin-dependent enzyme activity as compared to the level of calmodulin-dependent enzyme activity in the absence of calmodulin inhibitors.

Calcium is one of the "second messengers" which relays chemical and electrical signals within a cell. This signal transduction and, hence the regulation of biological processes, involves interaction of calcium ion with high-affinity calcium-binding proteins. One such protein is the ubiquitous intracellular receptor protein calmodulin.

Upon calcium binding, calmodulin interacts with a number of protein targets in a calcium dependent manner, thereby altering a number of complex biochemical pathways that can affect the overall behavior of cells. The calcium-calmodulin complex controls the biological activity of more than thirty different proteins including several enzymes, ion transporters, receptors, motor proteins, transcription factors, and cytoskeletal components in eukaryotic cells.

Known calmodulin binding drugs are also encompassed as calmodulin inhibitors as disclosed herein, and include the following two classes of compounds. The first class includes, and is exemplified by the following compounds: (a) 8-anilino-1-naphthalenesulfonate, (b) 9-anthroylcholine, (c) N-phenyl -1-naphthylamine The second class of compounds includes, and is exemplified by the following compounds: (a) N-(6 aminohexyl)-5-chloro-1-naphthalenesulfonamide, (b) N-(6 aminohexyl)-5-chloro -2-naphthalenesulfonamide, (c) N-(6 aminohexyl)-5-bromo-2-naphthalenesulfonamide Phenothiazine Compounds In some embodiments of all aspects of the present invention, a calmodulin inhibitor is a phenothiazine compound, for example, trifluoperazine (TFP), or flurphenazine, or perphenazine or a derivative or analogue thereof.

In some embodiments, a phenothiazine compound is trifluoperazine (TFP) or a derivative or analogue of a compound with the following structure:

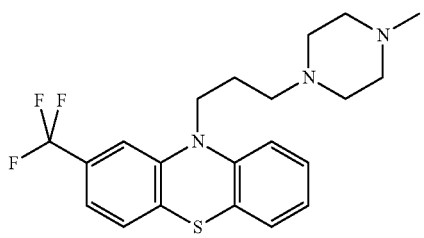 [SMILES: CN1CCN(CCCN2c3ccccc3Sc3ccc(C(F)(F)F)cc32)CC1]

Trifluoperazine has the chemical name of 10-[3-(4-methylpiperazin-1-yl)propyl]-2-(trifluoromethyl)-10H-phenothiazine (also known as brand names ESKAZINYL™, ESKAZINE™, FLUROPERAZINE™, JATRONEURAL™, MODALINA™, NOVO-TRIFLUZINE™, STELAZINE™, SYNKLOR™, TERFLUZINE™, TRIFLUOPERAZ™, TRIFTAZIN™) is a typical antipsychotic of the phenothiazine chemical class. Trifluoperazine is also known as synonyms Trifluoperazin, Trifluoperazina, Trifluoperazine Dihydrochloride, Trifluoperazine HCl, Trifluoperazine Hydrochloride, Trifluoromethylperazine, Trifluoroperazine, Trifluoroperazine Dihydrochloride, Trifluoroperazine Hydrochloride, Trifluperazine, Trifluroperizine, Triphthazine Dihydrochloride, Tryptazine Dihydrochloride, Trifluoperazine has central antiadrenergic, antidopaminergic, and minimal anticholinergic effects. It is believed to work by blockading dopamine D1 and D2 receptors in the mesocortical and mesolimbic pathways, relieving or minimizing such symptoms of schizophrenia as hallucinations, delusions, and disorganized thought and speech. In some embodiments, TPE is typically administered in 1 mg-20 mg unit doses, for example, administration of at least about 1 mg, or at least about 2 mg, or at least about 5 mg, or at least about 10 mg, or at least about 15 mg, or at least about 20 mg, or more than 20 mg. In some embodiments, TFP is administered orally, e.g., by way of a tablet.

In some embodiments, a derivative of analogue of TFP is a derivative or analogue of TFP which cannot cross the blood brain barrier.

Production of TFP is disclosed in U.S. Pat. No. 2,921,069, which is incorporated herein in its entirety by reference.

In some embodiments, a phenothiazine compound is flurphenazine or a derivative or analogue of a compound with the following structure:

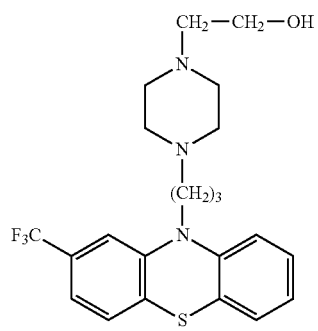

Fluphenazine (4-[3-[2-(trifluoromethyl)phenothiazin-10-yl]propyl]-1-piperazineethanol), is synthesized by any of the methods described already for the preparation of trifluoperazine and related antipsychotics, and is disclosed in U.S. Pat. No. 3,058,979 (1962), U.S. Pat. No. 3,394,131 (1963), U.S. Pat. No. 2,766,235 (1956) and U.S. Pat. No. 3,194,733 (1965) and GB Patents 833474 and 829246 (1960), which are incorporated herein in their entirety by reference.

Fluphenazine is typically used as an antipsychotic drug used for the treatment of psychoses such as schizophrenia, manic phases of bipolar disorder, agitation, and dementia. It belongs to the piperazine class of phenothiazines In some embodiments, fluphenazine can be administered as an oral liquid or tablets (e.g., unit does of about 1 mg, 2.5 mg, 5 mg, 10 mg), or as an injectable form (including a short-acting and long-acting form).

Derivatives and salts of fluphenazine include, but are not limited to: Fluphenazine decanoate (Brand names: Modecate, Prolixin Decanoate, Dapotum D, Anatensol, Fludecate, Sinqualone Deconoate); Fluphenazine enanthate (Brand Names: Dapotum Injektion, Flunanthate, Moditen Enanthate Injection, Sinqualone Enanthate), Fluphenazine hydrochloride (Brand names: Prolixin, Permitil, Dapotum, Lyogen, Moditen, Omca, Sediten, Selecten, Sevinol, Sinqualone, Trancin), and flucate.

Fluphenazine has an incomplete oral bioavailability of 40% to 50% (due to extensive first pass metabolization in the liver). Its half life is 15 to 30 hours. In children over age 16 and in adults, fluphenazine is usually given in oral dosages ranging from about 0.5-10 mg daily. The total dosage is usually divided and taken two to four times throughout the day. The dosage is typically reduced at a gradual pace over time to a range between 1 mg and 5 mg. Older adults usually receive lower doses that begin in the range of 1 mg-2.5 mg per day. In children under age 16, the usual range is 0.25-3.5 mg per day divided into several doses. Maximum dosage is normally 10 mg per day for this age group.

Fluphenazine drug is also available by injection. In adults, slow-acting injections into the muscle range from 1.25-10 mg per day divided into several doses. A long-acting injectable form can also be administered to patients who have been stabilized on the drug every month. The dose for the long-acting preparation ranges from 12.5-25 mg given every one to four weeks in adults. The dosage for children is typically lower in all cases.

In some embodiments, a phenothiazine compound is perphenazine or a derivative or analogue of a compound with the following structure:

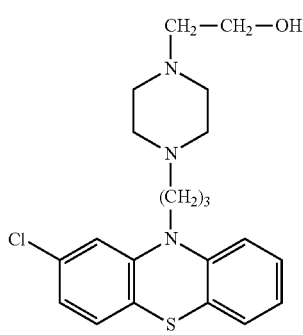

Preparation of perphenazine (4-[3-(2-Chloro-10H-phenothiazin-10-yl)propyl]-1-piperazineethanol) is also described in U.S. Pat. Nos. 2,766,235 and 2,860,138, which are incorporated herein in their entity by reference. Perphenazine is sold under the brand names TRILAFON™ (single drug) and ETRAFON™/TRIAVAIL™ (contains fixed dosages of amitriptyline). A brand name in Europe is DECENTAN™ pointing to the fact that perphenazine is approximately 5-times more potent than chlorpromazine. Perphenazine has an oral bioavailability of approximately 40% and a half-life of 8 to 12 hours (up to 20 hours), and is usually given in 2 or 3 divided doses each day. It is possible to give two-thirds of the daily dose at bedtime and one-third during breakfast to maximize hypnotic activity during the night and to minimize daytime sedation and hypotension without loss of therapeutic activity.

In some embodiments, perphenazine can be administered orally, e.g., via are tablets (e.g., with 2, 4, 8, 16 mg unit doses) and liquid concentrate (e.g., 4 mg/ml unit dose).

A Perphenazine injectable USP solution can be administered by intramuscular (i.m.) injection, for patients who are not willing to take oral medication or if the patient is unable to swallow. Due to a better bioavailability of the injection, two-thirds of the original oral dose is sufficient. The incidence of hypotension, sedation and extrapyramidal side-effects may be higher compared to oral treatment. The i.m.-injections are appropriate for a few days, but oral treatment should start as soon as possible.

In many countries, depot forms of perphenazine exist (as perphenazine enanthate). One injection works for 1 to 4 weeks depending on the dose of the depot-injection.

Naphthalenesulfonamide Compounds

In some embodiments of all aspects of the present invention, a calmodulin inhibitor is a naphthalenesulfonamide compound, for example but not limited to, A-3, W-7 (N-(6-Aminohexyl) -5-chloro-1-naphthalenesulfonamide hydrochloride), A-7, W-5, or a derivative or an thereof.

In some embodiments, a naphthalenesulfonamide compound is A-3, or a derivative or an analogue of a compound with the following structure:

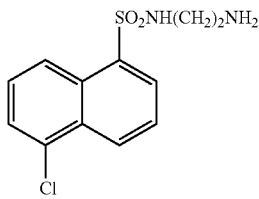

In some embodiments, a naphthalenesulfonamide compound is W-7 (N-(6-Aminohexyl) -5-chloro-1-naphthalenesulfonamide hydrochloride), or a derivative or an analogue of a compound with the following structure:

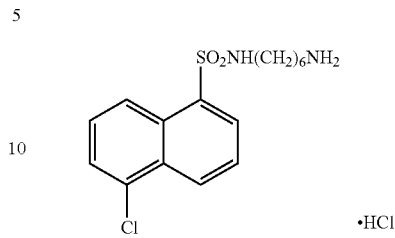

In some embodiments, a derivative of W-7 is N-(6-aminohexyl)-1-naphthalenesulfonamide hydrochloride or N-(6-aminohexyl)-5-chloro-2-naphthalenesulfonamide.

W-7 inhibits Ca2+-calmodulin-dependent phosphodiesterase (IC50=28 µM) and myosin light chain kinase (IC50=51 µM) and is commercially available from Tocris Bioscience.

In some embodiments, a naphthalenesulfonamide compound is A-7, or a derivative or an analogue of a compound with the following structure:

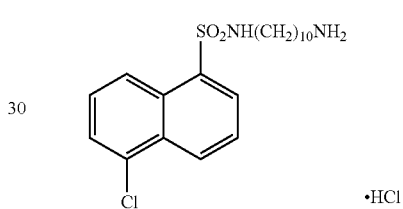

In some embodiments, a naphthalenesulfonamide compound is W-5, or a derivative or an analogue of a compound with the following structure:

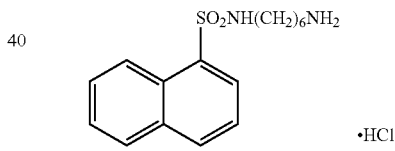

In some embodiments of all aspects of the present invention, a calmodulin inhibitor is CGS-9343 (zaldaride maleate), or a derivative or an analogue thereof. In some embodiments, the calmodulin inhibitor is CGS-9343 (zaldaride maleate), or a derivative or an analogue of a compound with the following structure:

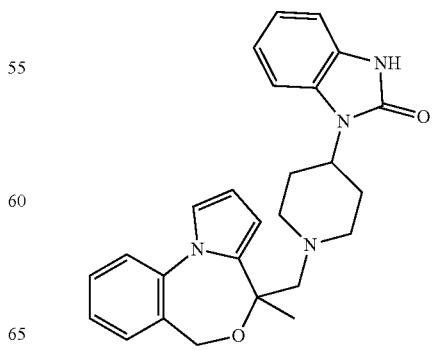

In some embodiments, the method encompasses treating a subject with a ribosomal disorder or ribosomopathy, comprising administering an effective amount of a calcium channel blocker or a calmodulin inhibitor to the subject to decrease p53 or p21 in at least one of CD34+ cells, erythroid cells or erythroid differentiated cells in the subject, where the calmodulin inhibitor or calcium channel blocker or selected from the group consisting of: nimodipine, YS-035, bepridil, bepridil-hydrochloride, phenoxybenzamine, cetiedil, chlorpromazine, promazine, desipramine, flunarizine, or promethazine In some embodiments, a calmodulin inhibitor is an inhibitor of the checkpoint kinase 2 enzyme (Chk2), for example, but not limited to BML-227. Accordingly, in some embodiments, the calmodulin inhibitor is BML-227, or a derivative or an analogue of a compound with the following structure:

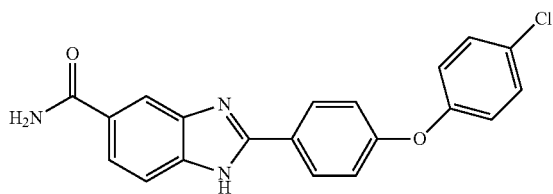 [SMILES: NC(=O)c1ccc2[nH]c(-c3ccc(Oc4ccc(Cl)cc4)cc3)nc2c1]

BML-277 is a highly selective inhibitor of Chk2 (IC50=15 nM) displaying <25% inhibition of 35 other kinases at 10 μM). It displays potent radioprotective activity and prevents apoptosis of human T cells subjected to ionizing radiation (EC50=3-7.6 μM). Useful tool for dissecting the role of Chk2 in cellular signaling. BML-277 is commercially available from Enzo Life Sciences.

In some embodiments of all aspects of the present invention, a calmodulin inhibitor is a calmodulin dependent phosphodiesterase 1 (pde 1) inhibitor, for example, but not limited to vinpocetine. Vinpocetine (also known as: CAVINTON™, INTELECTOL™; chemical name: ethyl apovincaminate) is a semisynthetic derivative alkaloid of vincamine (sometimes described as "a synthetic ethyl ester of apovincamine"). Vinpocetine is reported to have cerebral blood-flow enhancing and neuroprotective effects, and is used as a drug in Eastern Europe for the treatment of cerebrovascular disorders and age-related memory impairment. A citrate salt of vinpocetine is disclosed in U.S. Pat. No. 4,749,707 which is incorporated herein in its entirety by reference.

Additional Calmodulin Inhibitors

A number of calmodulin targeted compounds are known and used for a variety of therapeutic applications. Among suitable inhibitors of calmodulin are anthralin and cyclosporin A. Typically, anthralin is administered topically at concentrations of about 0.1% to about 2%. Another inhibitor of calmodulin activity is zinc (M. K. Heng et al., "Reciprocity Between Tissue Calmodulin and cAMP Levels: Modulation by Excess Zinc," Br. J. Dermatol. 129:280-285 (1993)). zinc can be administered orally or as a topical preparation, i.e., as an ointment.

Chlorpromazine (THORAZINE™) and related phenothiazine derivatives, disclosed, for example, in U.S. Pat. No. 2,645,640 which is incorporated herein by reference, are calmodulin antagonists useful as tranquilizers and sedatives. Naphthalene-sulfonamides, also calmodulin antagonists, are known to inhibit cell proliferation, as disclosed, for example, in Hidaka et al., PNAS, 78:4354-4357 (1981) and are useful as antitumor agents. In addition, the cyclic peptide cyclosporin A (SANDIMMUNE™), disclosed in U.S. Pat. No. 4,117,118, which is incorporated herein in its entirety by reference is as an immunosuppressive agent which is thought to work by inhibiting calmodulin mediated responses in lymphoid cells. U.S. Pat. No. 5,340,565, which is incorporated herein by reference, additionally describes the use of calmodulin antagonists or inhibitors.

Peptide inhibitors of calmodulin are also encompassed for use in the methods, kits and compositions as disclosed herein, for example, peptide calmodulin inhibitors disclosed in U.S. Pat. No. 5,840,697, which is incorporated herein in its entirety by reference.

In particular, the use of the calmodulin inhibitors bepridil (also known as bepridil-hydrochloride, VASCOR®, UNICORDIUM®, CORDIUM®, BEPRICOR® and CERM-1978 (mainly used in publications from the late 1970s)), phenoxybenzamine (i.a. marketed as BENZPYRAN®) cetiedil (also known as STRATENE® and VASOCET®) and/or W7 (also known as N-(6-Aminohexyl)-5-chloro-1-naphthalenesulfonamide hydrochloride (Hidaka et al, J Pharmacol Exp Ther 1978 207(1):8-15 and Hidaka (1981) PNAS, 78, 4354-4357 is envisaged. Moreover, the use of the calmodulin inhibitors zaldaride maleate (also known in the art as CGS 9343B) and chlorpromazine (also known as PROPAPHENIN®, LARGACTIL®, EPOKUHL® and THORAZINE®) are envisaged in context of the present invention. These calmodulin inhibitors are, for example, described in Norman, 1987 and Khan, 2000, respectively.

Further compounds to be used as calmodulin inhibitors in context of the present invention may be compounds like promazine, desipramine, flunarizine, or promethazine. For example, these compounds are described in US 2006/0009506 and have structural similarity to compounds known to act as calmodulin inhibitors.

Also derivatives of said compounds are useful in context of the present invention, for example W7-derivatives, like N-(6-aminohexyl)-1-naphthalenesulfonamide hydrochloride or N-(6-aminohexyl) -5-chloro-2-naphthalenesulfonamide.

In in vitro experiments and in animals bepridil has been shown to influence a large number of processes, including many ion channel currents (calcium, potassium and sodium channels) such as delayed rectifier K+ current (Yumoto et al., 2004), HERG (Chouabe et al., 1998), Na+/Ca2+ exchanger (Calabresi et al., 1999). Bepridil can even bind actin (Cramb and Dow, 1983). The IC50 for these processes is typically in the low micromolar range and thus, similar to what was observed in context of this invention for β-cleavage inhibition. The molecular mechanism (direct or indirect inhibition) is mostly unknown. Bepridil is currently used for the treatment of angina and other forms of heart disease. Chlorpromazine or trifluoperazine are old drugs against psychotic disorders. Bepridil has anti-anginal properties and (less well characterized) anti-arrhythmic and anti-hypertensive properties. Bepridil has also been reported to ameliorate experimental autoimmune encephalomyelitis in mice (Brand-Schieber and Werner, 2004). Chemically, it is not related to other calcium channel blockers, such as nifedipine, verapamil or diltiazem. Furthermore, bepridil is known as a calcium antagonist (Hollingshead et al., 1992), but the molecular mechanism of bepridil's cellular actions is not well understood.

In terms of the present inventions, the use of the calmodulin inhibitors bepridil, phenoxybenzamine, cetiedil and/or W7 can be used in the compositions and methods provided herein.

The calmodulin inhibitors to be used in terms of the present invention may have an overall high degree of hydrophobicity and/or may comprise an amino group linked through a spacer to an aromatic system. Thereby, the amino group may be a heterocyclic amine. The spacer may be an aliphatic hydrocarbon chain, but may also include ester linkages or side chains. The aromatic system maximally comprise 1, 2 or 3 aromatic rings, even heterocycles may also be employed. The aromatic rings may be directly fused to each other or may also or be separate (e. g. such as in bepridil). The aromatic rings may also carry substituents, such as chlorine.

RNAi Inhibitors of Chk2 and PDE1

As discussed herein, the inventors have discovered that inhibition of Chk2 and PDE1 can be used as calmodulin inhibitors in the methods and compositions as disclosed for the treatment of ribosome protein disorders and ribosomopathy as disclosed herein. In some embodiments, an inhibitor of Chk2 or PDE1 is a protein inhibitor, and in some embodiments, the inhibitor is any agent which inhibits the function of Chk2 or PDE1 or the expression of Chk2 or PDE1 from its gene. In some embodiments, an inhibitor of Chk2 or PDE1 is a gene silencing agent.

Without wishing to be bound by theory, Chk2 is also known by aliases; CHEK2, bA444G7, CDS1, CHK2, HuCds1, PP1425, CHK2 (checkpoint, S.pombe) homolog, and RAD53, and is encoded by nucleic acid sequence NM_001005735.1 (SEQ ID NO: 1), and has an amino acid of NP_001005735.1 (SEQ ID NO: 2). Inhibition of the Chk2 gene can be by gene silencing RNAi molecules according to methods commonly known by a skilled artisan. For example, a gene silencing siRNA oligonucleotide duplexes targeted specifically to human Chk2 (GenBank No: NM_001005735.1) can readily be used to knockdown Chk2 expression. Chk2 mRNA can be successfully targeted using siRNAs; and other siRNA molecules may be readily prepared by those of skill in the art based on the known sequence of the target mRNA. To avoid doubt, the sequence of a human Chk2 is provided at, for example, GenBank Accession Nos. NM_001005735.1 (SEQ ID NO: 1). Accordingly, in avoidance of any doubt, one of ordinary skill in the art can design nucleic acid inhibitors, such as RNAi (RNA silencing) agents to the nucleic acid sequence of NM_001005735.1 which is as follows:

```
                                                              (SEQ ID NO: 1)
   1 gcaggtttag cgccactctg ctggctgagg ctgcggagag tgtgcggctc caggtgggct 61 cacgcggtcg tgatgtctcg ggagtcggat gttgaggctc agcagtctca tggcagcagt 121 gcctgttcac agcccatgg cagcgttacc cagtcccaag gctcctcctc acagtcccag 181 ggcatatcca gctcctctac cagcacgatg ccaaactcca gccagtcctc tcactccagc 241 tctgggacac tgagctcctt agagacagtg tccactcagg aactctattc tattcctgag 301 gaccaagaac ctgaggacca agaacctgag gagcctaccc ctgcccctg ggctcgatta 361 tgggcccttc aggatggatt tgccaatctt gagacagagt ctggccatgt tacccaatct 421 gatcttgaac tcctgctgtc atctgatcct cctgcctcag cctcccaaag tgctgggata 481 agaggtgtga ggcaccatcc ccggccagtt tgcagtctaa aatgtgtgaa tgacaactac 541 tggtttggga gggacaaaag ctgtgaatat tgctttgatg aaccactgct gaaaagaaca 601 gataaatacc gaacatacag caagaaacac tttcggattt tcagggaagt gggtcctaaa 661 aactcttaca ttgcatacat agaagatcac agtggcaatg gaacctttgt aaatacagag 721 cttgtaggga aggaaaacg ccgtcctttg aataacaatt ctgaaattgc actgtcacta 781 agcagaaata agttttttgt ctttttgat ctgactgtag atgatcagtc agtttatcct 841 aaggcattaa gagatgaata catcatgtca aaaactcttg gaagtggtgc ctgtggagag 901 gtaaagctgg ctttcgagag gaaaacatgt aagaaagtag ccataaagat catcagcaaa 961 aggaagtttg ctattggttc agcaagagag gcagacccag ctctcaatgt tgaaacagaa 1021 atagaaattt tgaaaaagct aaatcatcct tgcatcatca agattaaaaa ctttttgat 1081 gcagaagatt attatattgt tttggaattg atggaagggg gagagctgtt tgacaaagtg 1141 gtggggaata acgcctgaa agaagctacc tgcaagctct atttttacca gatgctcttg 1201 gctgtgcagt accttcatga aaacggtatt atacaccgtg acttaaagcc agagaatgtt 1261 ttactgtcat ctcaagaaga ggactgtctt ataaagatta ctgattttgg gcactccaag 1321 attttgggag agacctctct catgagaacc ttatgtggaa cccccaccta cttggcgcct 1381 gaagttcttg tttctgttgg gactgctggg tataaccgtg ctgtggactg ctggagttta 1441 ggagttattc tttttatctg ccttagtggg tatccaccct tctctgagca taggactcaa
```

```
-continued
1501 gtgtcactga aggatcagat caccagtgga aaatacaact tcattcctga agtctgggca 1561 gaagtctcag agaaagctct ggaccttgtc aagaagttgt tggtagtgga tccaaaggca 1621 cgttttacga cagaagaagc cttaagacac ccgtggcttc aggatgaaga catgaagaga 1681 aagtttcaag atcttctgtc tgaggaaaat gaatccacag ctctaccccca ggttctagcc 1741 cagccttcta ctagtcgaaa gcggccccgt gaaggggaag ccgagggtgc cgagaccaca 1801 aagcgcccag ctgtgtgtgc tgctgtgttg tgaactccgt ggtttgaaca cgaaagaaat 1861 gtaccttctt tcactctgtc atctttcttt tctttgagtc tgtttttta tagtttgtat 1921 tttaattatg ggataattg cttttcaca gtcactgatg tacaattaaa aacctgatgg 1981 aacctggaaa a
```

Without wishing to be bound by theory, pde1 is also known by aliases; PDE1A and is encoded by nucleic acid sequence NM_001003683.2 (SEQ ID NO: 3), and has an amino acid of NP_001003683.1 (SEQ ID NO: 4). Inhibition of the PDE1 gene can be by gene silencing RNAi molecules according to methods commonly known by a skilled artisan. For example, a gene silencing siRNA oligonucleotide duplexes targeted specifically to human PDE1 (GenBank No: NM_001003683.2) can readily be used to knockdown Pde1 expression. Pde1 mRNA can be successfully targeted using siRNAs; and other siRNA molecules may be readily prepared by those of skill in the art based on the known sequence of the target mRNA. To avoid doubt, the sequence of a human Pde1 is provided at, for example, GenBank Accession Nos. NM_001003683.2 (SEQ ID NO: 3). Accordingly, in avoidance of any doubt, one of ordinary skill in the art can design nucleic acid inhibitors, such as RNAi (RNA silencing) agents to the nucleic acid sequence of NM_001003683.2 which is as follows:

```
                                                                    (SEQ ID NO: 3)
   1 ttattacatc ctgcccttgt tctgttggta gagaggaatt cagcttcttc tggagcgcga 61 aagtcattca cgtttctctt gtgcataata gagctcgtaa actgtaggaa ttctgatgtg 121 cttcagtgca cagaacagta acagatgagc tgcttttggg gagagcttga gtactcagtc 181 ggagcatcat catgggtct agtgccacag agattgaaga attggaaaac accacttta 241 agtatcttac aggagaacag actgaaaaaa tgtggcagcg cctgaaagga atactaagat 301 gcttggtgaa gcagctggaa agaggtgatg ttaacgtcgt cgacttaaag aagaatattg 361 aatatgcggc atctgtgctg gaagcagttt atatcgatga acaagaaga cttctggata 421 ctgaagatga gctcagtgac attcagactg actcagtccc atctgaagtc cgggactggt 481 tggcttctac ctttacacgg aaaatgggga tgacaaaaaa gaaacctgag gaaaaaccaa 541 aatttcggag cattgtgcat gctgttcaag ctggaatttt tgtggaaaga atgtaccgaa 601 aaacatatca tatggttggt ttggcatatc cagcagctgt catcgtaaca ttaaaggatg 661 ttgataaatg gtctttcgat gtatttgccc taaatgaagc aagtggagag catagtctga 721 agtttatgat ttatgaactg tttaccagat atgatcttat caaccgtttc aagattcctg 781 tttcttgcct aatcaccttt gcagaagctt tagaagttgg ttacagcaag tacaaaaatc 841 catatcacaa tttgattcat gcagctgatg tcactcaaac tgtgcattac ataatgcttc 901 atacaggtat catgcactgg ctcactgaac tggaaatttt agcaatggtc tttgctgctg 961 ccattcatga ttatgagcat acagggacaa caaacaactt tcacattcag acaaggtcag 1021 atgttgccat tttgtataat gatcgctctg tccttgagaa tcaccacgtg agtgcagctt 1081 atcgacttat gcaagaagaa gaaatgaata tcttgataaa tttatccaaa gatgactgga 1141 gggatcttcg gaacctagtg attgaaatgg ttttatctac agacatgtca ggtcacttcc 1201 agcaaattaa aaatataaga aacagtttgc agcagcctga agggattgac agagccaaaa 1261 ccatgtccct gattctccac gcagcagaca tcagccaccc agccaaatcc tggaagctgc 1321 attatcggtg gaccatggcc ctaatggagg agttttttcct gcagggagat aaagaagctg
```

```
-continued
1381 aattagggct tccattttcc ccactttgtg atcggaagtc aaccatggtg gcccagtcac 1441 aaataggttt catcgatttc atagtagagc caacattttc tcttctgaca gactcaacag 1501 agaaaattgt tattcctctt atagaggaag cctcaaaagc cgaaacttct tcctatgtgg 1561 caagcagctc aaccaccatt gtggggttac acattgctga tgcactaaga cgatcaaata 1621 caaaaggctc catgagtgat gggtcctatt ccccagacta ctcccttgca gcagtggacc 1681 tgaagagttt caagaacaac ctggtggaca tcattcagca gaacaaagag aggtggaaag 1741 agttagctgc acaagaagca agaaccagtt cacagaagtg tgagtttatt catcagtaaa 1801 cacctttaag taaaacctcg tgcatggtgg cagctctaat ttgaccaaaa gacttggaga 1861 ttttgattat gcttgctgga aatctaccct gtcctgtgtg agacaggaaa tctatttttg 1921 cagattgctc aataagcatc atgagccaca taaataacag ctgtaaactc cttaattcac 1981 cgggctcaac tgctaccgaa cagattcatc tagtggctac atcagcacct tgtgctttca 2041 gatatctgtt tcaatggcat tttgtggcat ttgtctttac cgagtgccaa taaattttct 2101 ttgagcagct aattgctaat tttgtcattt ctacaataaa gcttggtcca cctgttttc
```

An inhibitor of Pde1 and/or Chk2 can be any agent which inhibits the function of Pde1 and/or Chk2, such as antibodies, gene silencing RNAi molecules and the like. Commercial neutralizing antibodies of Pde1 and/or Chk2, and or calmodulin are encompassed for use in the methods and compositions as disclosed herein. Additionally, small molecules agonists of calmodulin and Pde 1 and/or Chk2 are known by one of ordinary skill in the art and are encompassed for use in the methods and compositions as disclosed herein as an inhibitor of calmodulin function.

A person skilled in the art is able to test whether a certain compound acts as a calmodulin inhibitor. Test systems for calmodulin activity of certain compounds are known in the art. For instance, such test systems are described in Agre (1984; Binding of 1251-Calmodulin to erythrocyte membranes,), Itoh (1986; Competition experiment, which measures, whether novel compounds competes with 3H bepridil for calmodulin binding, Myosin light chain kinase activity), Roberson (2005; Inhibition of Gonadotropin-releasing hormone induction of the kinase ERK) and Kahn (1998; Calmodulin inhibitors should induce the proteolytic cleavage of L-selectin (as measured by Western Blot or by FACS)). In terms of the present invention inhibition of myosin light chain kinase (MLCK) is preferred, as discussed in more detail below. More details on useful test systems are given herein below and in the Examples, for example, the ability to rescue at least one of the morphological, hematopoietic or endothelial defects in the Rps29−/− zebrafish embryo and/or prevent p53 function and nuclear accumulation in A549 lung cancer cell line that have had RPS19 knocked down by siRNA, or reduce p21 levels or increase erythroid markers in CD34+ cells that have had RPS19 knocked down by siRNA.

In some embodiments, the inhibition of calmodulin by a calmodulin inhibitor as disclosed herein, or analogue or derivative thereof can be assessed by one of ordinary skill in the art using assays well known in the art, for example, inhibition of calmodulin may, inter alia, be determined in the following in vitro assay, which measured the calmodulin-dependent activation of myosin light chain kinase (MLCK). Activated MLCK phosphorylates chicken gizzard myosin light chain. If calmodulin is inhibited the rate of myosin light chain phosphorylation is reduced. To test this, the following experiment is carried out (according to Itoh et al. Biochem. Pharm. 1986,35:217-220). The reaction mixture (0.2 ml) contains 20 mM Tris-HCl (pH 7.5), 0.05 mM [γ-32P] ATP (1 µCi/assay tube), 5 mM MgCl2, 10 µM myosin light chain, 24 nM calmodulin and 0.1 mM CaCl2. MLCK (specific activity: 4.5 moles/min/mg) concentration from chicken gizzard is 0.1 µg/ml. The incubation is carried out at 30° C. for 4 min. The reaction is terminated by addition of 1 ml of 20% trichloroacetic acid. Then 0.1 ml of bovine serum albumin (1 mg/ml) is added to the reaction mixture. The sample is then centrifuged for 10 min, the pellet is resuspended in 5% trichloroacetic acid. The final pellet is dissolved in 2 ml of 1 N NaOH and the radioactivity measured in a liquid scintillation counter. Trypsin-treated MLCK can be prerared as described in ltoh et al. J Pharmacol. Exp. Ther. 1984,230, p737. The reaction is initiated by the addition of the ATP and is carried out in the presence of the potential inhibitors or—as a control—in the presence of their solvent. Different concentrations of the compounds will be tested in the above assay. The concentration of the compound which results in 50% decrease of kinase activity will be the IC50 concentration.

In some embodiments, a method to assay a compound, e.g., an analogue or derivative of a calmodulin inhibitor as disclosed herein for inhibition of calmodulin is a standard assay assessing cAMP levels as described in Inagaki et al., 1986 "Napthalenesulfonamides as Calmodulin Antagonists and Protein Kinase Inhibitors", which is incorporated herein by reference in its entirety. Alternatively, commercially available kits to measure cAMP levels can be used, for example, available from Sigma. Cell Signaling, eenzyme-.com, biovision and the like.

An alternative method to assay a compound, e.g., an analogue or derivative of a calmodulin inhibitor as disclosed herein for inhibition of calmodulin is the method as modified from Kahn et al. Cell 1998,92:809-818: As a read-out the inhibition of Gonadotropin-releasing hormone (GnRH) induced ERK Phosphorylation in αT3-1 cells as measured. αT3-1 cells are serum-starved for 2 h, pretreated with control solvent or increasing concentrations of the compounds to be tested for 30 min. Then GnRH is administered for 60 min. Cell lysates are prepared and resolved by SDS-PAGE. Western blot analysis is used to determine the phosphorylation status of ERKs using a phospho-specific antibody (cell signaling technologies). As a control, total ERK2 will also be determined using an ERK specific antibody (Santa Cruz Biotech). Western-Blot fluorescence of phospho-ERK and total ERK2 will be quantified. The ratio of phospho-ERK/total ERK2 will be plotted against the concentration of the compound to be tested. The estimated concentration, at which a 50% reduction of ERK phosphorylation (rel. to total ERK2) occurs, can be used as the IC50 value for this compound.

Accordingly, the person skilled in the art is readily in a position to elucidate by means and methods known in the art whether a given compound is a calmodulin inhibitor/antagonist.

In context of this is invention, it is of note that the term "calmodulin inhibitor" is employed as a synonym for "calmodulin antagonist".

One aspect of the present invention provides methods of identifying calmodulin inhibitors useful in the methods and compositions of the present invention, for example, by the method comprising measuring the inhibition of calmodulin in a calmodulin inhibitor assay, such as a MLCK activation assay as disclosed herein, and/or the ability to rescue at least one of the morphological, hematopoietic or endothelial defects in the Rps29−/− zebrafish embryo and/or prevent p53 function and nuclear accumulation in A549 lung cancer cell line that have had RPS19 knocked down by siRNA, or reduce p21 levels or increase erythroid markers in CD34+ cells that have had RPS19 knocked down by siRNA as described in the Examples.

In some embodiments, a calmodulin inhibitor as disclosed herein can inhibit or decrease the activity of calmodulin activity by at least about 10%, relative to the activity level in the absence of inhibitors of LSF, e.g., at least about 15%, at least about 20%, at least about 30%, at least about 40%, at least about 50%, at least about 60%, at least about 70%, at least about 80%, at least about 90%, 95%, 99% or even 100%. In certain embodiments, calmodulin inhibitors as disclosed herein can decrease expression of calmodulin by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of a calmodulin inhibitor.

The expression of calmodulin includes the amount of RNA transcribed from a gene, e.g. CALM1 that encodes calmodulin, and/or the amount of calmodulin proteins that is obtained by translation of RNA transcribed from a gene, e.g. CALM1. For example, a calmodulin inhibitor as disclosed herein can inhibit expression of calmodulin by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a calmodulin inhibitor.

Additionally, ability of a compound to inhibit calmodulin can be also assessed by measuring a decrease in or an inhibition of biological activity of calmodulin as compared to a negative control, e.g. the experimental condition in the absence of calmodulin inhibitors. Accordingly, a calmodulin inhibitor as disclosed herein can inhibit biological activity of calmodulin, by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a calmodulin inhibitor. In some embodiments, the ability of a compound to inhibit calmodulin is assessed by rescuing least one of the morphological, hematopoietic or endothelial defects in the Rps29−/− zebrafish embryo and/or prevent p53 function and nuclear accumulation in A549 lung cancer cell line that have had RPS19 knocked down by siRNA, or reduce p21 levels or increase erythroid markers in CD34+ cells that have had RPS19 knocked down by siRNA as demonstrated in the Examples herein, as compared to a reference condition without treatment with such a calmodulin inhibitor.

The dosages to be administered can be determined by one of ordinary skill in the art depending on the clinical severity of the disease, the age and weight of the patient, the exposure of the patient to conditions that may precipitate outbreaks of psoriasis, and other pharmacokinetic factors generally understood in the art, such as liver and kidney metabolism. The interrelationship of dosages for animals of various sizes and species and humans based on $mg/m^3$ of surface area is described by E. J. Freireich et al., "Quantitative Comparison of Toxicity of Anticancer Agents in Mouse, Rat, Hamster, Dog, Monkey and Man," Cancer Chemother. Rep. 50: 219-244 (1966). Adjustments in the dosage regimen can be made to optimize the therapeutic response. Doses can be divided and administered on a daily basis or the dose can be reduced proportionally depending on the therapeutic situation.

Typically, these drugs will be administered orally, and they can be administered in conventional pill or liquid form. If administered in pill form, they can be administered in conventional formulations with excipients, fillers, preservatives, and other typical ingredients used in pharmaceutical formations in pill form. Typically, the drugs are administered in a conventional pharmaceutically acceptable formulation, typically including a carrier. Conventional pharmaceutically acceptable carriers known in the art can include alcohols, e.g., ethyl alcohol, serum proteins, human serum albumin, liposomes, buffers such as phosphates, water, sterile saline or other salts, electrolytes, glycerol, hydroxymethylcellulose, propylene glycol, polyethylene glycol, polyoxyethylenesorbitan, other surface active agents, vegetable oils, and conventional anti-bacterial or anti-fungal agents, such as parabens, chlorobutanol, phenol, sorbic acid, thimerosal, and the like. A pharmaceutically-acceptable carrier within the scope of the present invention meets industry standards for sterility, isotonicity, stability, and non-pyrogenicity.

The pharmaceutically acceptable formulation can also be in pill, tablet, or lozenge form as is known in the art, and can include excipients or other ingredients for greater stability or acceptability. For the tablets, the excipients can be inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc, along with the substance for controlling the activity of calmodulin and other ingredients.

The drugs can also be administered in liquid form in conventional formulations, that can include preservatives, stabilizers, coloring, flavoring, and other generally accepted pharmaceutical ingredients. Typically, when the drugs are administered in liquid form, they will be in aqueous solution. The aqueous solution can contain buffers, and can contain alcohols such as ethyl alcohol or other pharmaceutically tolerated compounds.

Alternatively, the drugs can be administered by injection by one of several routes well known in the art. It is, however, generally preferred to administer the drugs orally.

The drugs can be administered from once per day to up to at least five times per day, depending on the severity of the disease, the total dosage to be administered, and the judgment of the treating physician. In some cases, the drugs need not be administered on a daily basis, but can be administered every other day, every third day, or on other such schedules. However, it is generally preferred to administer the drugs daily.

Calcium Channel Blockers

Calcium blockers and chelators for use in the present invention also include compounds which control calcium channel activity, i.e., channels actuated by the depolarization of cell membranes thereby allowing calcium ions to flow into the cells. Such compounds inhibit the release of calcium ions from intracellular calcium storage thereby blocking signaling through the CaMKII pathway. Exemplary calcium blockers include, e.g., 1,4-dihydropyridine derivatives such as nifedipine, nicardipine, niludipine, nimodipine, nisoldipine, nitrendipine, milbadipine, dazodipine, and ferodipine; N-methyl-N-homoveratrilamine derivatives such as verapamil, gallopamil, and tiapamil; benzothiazepine derivatives such as diltiazem; piperazine derivatives such as cinnarizine, lidoflazine, and flunarizine; diphenylpropiramine derivatives such as prenylamine, terodiline, and phendiline; bepridil; and perhexyline. Exemplary calcium chelators include, e.g., BAPTA tetrasodium salt, 5,5'-Dibromo-BAPTA tetrasodium salt, BAPTA/AM, 5,5'-Difluoro-BAPTA/AM, EDTA tetrasodium salt (Ethylenediamine tetraacetic acid), EGTA (Ethylenebis (oxyethylenenitrilo)tetraacetic acid), EGTA/AM, MAPTAM, and TPEN.

Among calcium channel blockers are diltiazem, isradipine, nifedipine, and verapamil.

All calmodulin inhibitors and calcium channel blockers as disclosed herein are provided herein for illustrative purpose and disclose a particular isomer. However, one of ordinary skill in the art will recognize all possible isomers of the structures of any of the formulas of the calmodulin inhibitors, e.g, A-3, W-7, A-7, W-5 and CGS-9343. Therefore, other isomers and derivatives such as enantiomers of any of formulas of A-3, W-7, A-7, W-5 are considered to fall within the scope of the invention. As used herein, the term "isomer" refers to a compound having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. The designations may appear as a prefix or as a suffix; they may or may not be separated from the isomer by a hyphen; they may or may not be hyphenated; and they may or may not be surrounded by parentheses. The designations "(+)" and "(−)" are employed to designate the sign of rotation of plane-polarized light by the compound, with (−) meaning that the compound is levorotatory (rotates to the left). A compound prefixed with (+) is dextrorotatory (rotates to the right). Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

In various embodiments, calmodulin inhibitors as disclosed herein include enantiomers, derivatives, prodrugs, and pharmaceutically acceptable salts thereof.

In some embodiments, prodrugs of calmodulin inhibitors or calcium channel blockers are disclosed herein also fall within the scope of the invention. As used herein, a "prodrug" refers to a compound that can be converted via some chemical or physiological process (e.g., enzymatic processes and metabolic hydrolysis) to a functionally active calmodulin inhibitor.

Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs,* APHA Acad. Pharm. Sci. 40 (1977); *Bioreversible Carriers in Drug in Drug Design, Theory and Application,* E. B. Roche, ed., APHA Acad. Pharm. Sci. (1987); *Design of Prodrugs,* H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11,:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems,* G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.,* 15(2): 143-53 (1990); Balimane and Sinko, "Involvement of multiple transporters in the oral absorption of nucleoside analogues", *Adv. Drug Delivery Rev.,* 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs,* [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

Calmodulin inhibitors and calcium channel blockers as disclosed herein also include pharmaceutically acceptable salts thereof. As used herein, the term "pharmaceutically-acceptable salts" refers to the conventional nontoxic salts or quaternary ammonium salts of calmodulin inhibitors as disclosed herein, e.g., from non-toxic organic or inorganic acids. These salts can be prepared in situ in the administration vehicle or the dosage form manufacturing process, or by separately reacting a calmodulin inhibitor in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Use of the Calmodulin Inhibitors to Treat Ribosomal Disorders and Ribosomopathies In some embodiments, a calmodulin inhibitor as disclosed herein can be used to treat various disease and disorders associated with ribosomal proteins or ribosomopathies. For instance, the calmodulin inhibitors can be used to treat a subject who has a mutation in one or more ribosomal proteins, or have a decreased level of the ribosomal protein.

In some embodiments, the calmodulin inhibitors as disclosed herein can be used in a method of treating a subject with a ribosomal disorder such as Diamond Blackfan Anemia (DBA). There are a variety of types of Diamond Blackfan anemeia, for example, where the subject has DBA1, DBA2, DBA3, DBA4, DBA5, DBA6, DBA7, or DBA8. Diamond Blackfan anemia (DBA), also known as Blackfan-Diamond anemia and Inherited erythroblastopenia, is a congenital erythroid aplasia that usually presents in infancy DBA patients have low red blood cell counts (anemia). The rest of their blood cells (the platelets and the white blood cells) are normal. This is in contrast to Shwachman-Bodian-Diamond syndrome, in which the bone marrow defect results primarily in neutropenia, and Fanconi anemia, where all cell lines are affected resulting in pancytopenia. A variety of other congenital abnormalities may also occur. Diamond Blackfan anemia is characterized by anemia (low red blood cell counts) with decreased erythroid progenitors in the bone marrow. This usually develops during the neonatal period. About 47% of affected individuals also have a variety of congenital abnormalities, including craniofacial malformations, thumb or upper limb abnormalities, cardiac defects, urogenital malformations, and cleft palate. Low birth weight and generalized growth delay are sometimes observed. DBA patients have a modest risk of developing leukemia and other malignancies.

Typically, a diagnosis of DBA is made through a blood count and a bone marrow biopsy. A diagnosis of DBA is made on the basis of anemia, low reticulocyte (immature red blood cells) counts, and diminished erythroid precursors in bone marrow. Features that support a diagnosis of DBA include the presence of congenital abnormalities, macrocytosis, elevated fetal hemoglobin, and elevated adenosine deaminase levels in red blood cells. Most patients are diagnosed in the first two years of life. However, some mildly affected individuals only receive attention after a more severely affected family member is identified. About 20-25% of DBA patients may be identified with a genetic test for mutations in the RPS19 gene. Approximately 10-25% of DBA cases have a family history of disease, and most pedigrees suggest an autosomal dominant mode of inheritance.

Accordingly, in some embodiments, the calmodulin inhibitors as disclosed herein can be used in a method of treating a subject that has a mutation in ribosomal protein 19 (RPS19). The phenotype of DBA patients indicates a hematological stem cell defect specifically affecting the erythroid progenitor population. The RPS19 protein is involved in the production of ribosomes. Disease features may be related to the nature of RPS19 mutations. The disease is characterized by dominant inheritance, and therefore arises due to a partial loss of RPS19 protein function. I In alternative embodiments, the calmodulin inhibitors as disclosed herein can be used in a method of treating a subject with a mutation in ribosomal protein from at least one of, but not limited to RPS7, RPS10, RPS19, RPS24, PRS26, RPS17, PRS27L RPS29. RPL35A, PRLS and PPL11. For example, a mutation or variant in RPS19 causes DBA1, and a mutation or variant in RPS24 causes DBA3, a mutation or variant in RPS17 causes DBA4, a mutation or variant in RPS34A causes DBA5, a mutation or variant in RPLS causes DBA6, a mutation or variant in RPL11 causes DBA7, and a mutation or variant in RPS7 causes DBA8.

In some embodiments, a subject with a ribosomal disorder has a mutation in a ribosomal protein selected from the group consisting of: rPL2A, rPL2B, rPL3, rpL4A, rPL4B, rPL7A, rPL7B, rPL10, rPL11, rPL16A, rPL17A, rPL17B, rPL18A, rPL18B, Rp119A, rPL19, rPL25, rPL29, rpL31A, rpL31B, rPL36A, rPL40A, rPS1A, rPS6A, rPS6B, rPS14A, rPS15, rPS19, rPS23B, rPS25A, rPS26B, rPS29, rPS29B and rPS31.

In some embodiments of all aspects of the present invention, the method further comprises administering another therapeutic agent to treat the ribosomal protein defect, selected from the group consisting of: corticosteroids, blood transfusions and bone marrow transplants and other treatments known to persons of ordinary skill in the art. Corticosteroids can be used to treat anemia in DBA. Blood transfusions can also be used to treat severe anemia in DBA. Periods of remission may occur, during which transfusions and steroid treatments are not required. Bone marrow transplantation (BMT) can cure hematological aspects of DBA, adverse events in transfusion patients can occur (Diamond Blackfan Anemia Foundation; Pospisilova D et al., (2007). "Successful treatment of a Diamond-Blackfan anemia patient with amino acid leucine.". Haematologica 92 (5): e66.)

In some embodiments of all aspects of the present invention, a calmodulin inhibitor or calcium channel blocker administered to the subject increases the number of CD71+ erythroid cells in the subject and/or increases hemoglobin levels in the subject.

In some embodiments of all aspects of the present invention, the methods and calmodulin inhibitors and calcium channel blockers as disclosed herein can be used to treat a subject with a ribosomal disorder, such as DBA has a symptom of macrocytic anemia and/or craniofacial abnormalities.

In another embodiment, a calmodulin inhibitor as disclosed herein can be used in a method of treating a subject with a ribosomal disorder such as myelodysplasia, for example, but not limited to 5q-myelodysplasia. Myelodysplasia or myelodysplastic syndromes (MDS, formerly known as preleukemia) are a diverse collection of hematological (blood-related) medical conditions that involve ineffective production (or dysplasia) of the myeloid class of blood cells, and where the bone marrow does not function normally and produces insufficient number of normal blood cells.

Patients with MDS often develop severe anemia and require frequent blood transfusions. In most cases, the disease worsens and the patient develops cytopenias (low blood counts) caused by progressive bone marrow failure. In about one third of patients with MDS, the disease transforms into acute myelogenous leukemia (AML), usually within months to a few years.

The myelodysplastic syndromes are all disorders of the stem cell in the bone marrow. In MDS, hematopoiesis (blood production) is disorderly and ineffective. The number and quality of blood-forming cells decline irreversibly, further impairing blood production.

MDS affects the production of any, and occasionally all, types of blood cells including red blood cells, platelets, and white blood cells (cytopenias). About 50 percent of pediatric myelodysplasia can be classified in five types of MDS: refractory anemia, refractory anemia with ring sideroblasts, refractory anemia with excess blasts, refractory anemia with excess blasts in transformation, and chronic myelomonocytic leukemia. The remaining 50 percent typically present with isolated or combined cytopenias such as anemia, leucopenia and/or thrombocytopenia (low platelet count). Although chronic, MDS progresses to become acute myeloid leukemia (AML) in about 30 percent of patients.

The median age at diagnosis of a MDS is between 60 and 75 years; a few patients are younger than 50; MDS diagnoses are rare in children. Males are slightly more commonly affected than females. Signs and symptoms are nonspecific and generally related to the blood cytopenias include, but are not limited to:

(a) Anemia (low RBC count or reduced hemoglobin)—chronic tiredness, shortness of breath, chilled sensation, sometimes chest pain (b) Neutropenia (low neutrophil count)—increased susceptibility to infection (c) Thrombocytopenia (low platelet count)—increased susceptibility to bleeding and ecchymosis (bruising), as well as subcutaneous hemorrhaging resulting in purpura or petechia[5]

Many individuals are asymptomatic, and blood cytopenia or other problems are identified as a part of a routine blood count: neutropenia, anemia and thrombocytopenia (low cell counts of white and red blood cells, and platelets, respectively); splenomegaly or rarely hepatomegaly; abnormal granules in cells, abnormal nuclear shape and size; and/or chromosomal abnormalities, including chromosomal translocations and abnormal chromosome number.

Although there is some risk for developing acute myelogenous leukemia, about 50% of deaths occur as a result of bleeding or infection. Leukemia that occurs as a result of myelodysplasia is notoriously resistant to treatment.

5q-myelodysplasia, (also known as chromosome 5q deletion syndrome, chromosome 5q monosomy, or 5q-syndrome) is a rare disorder caused by loss of part of the long arm (q arm, band 5q31.1) of human chromosome 5.5q-myelodysplasia is characterized by macrocytic anemia often thrombocytosis, erythroblastopenia, megakaryocyte hyperplasia with nuclear hypolobation and an isolated interstitial deletion of chromosome 5. The 5q-syndrome is found predominantly in females of advanced age.

Some subjects with 5q-myelodysplasia have a decrease in Rps14 expression. Deletion of the miR-145 and miR-146 loci has been associated with elevated platelet count and megakaryocytic dysplasia associated with the 5q-syndrome. 5q-myelodysplasia affects bone marrow cells causing treatment-resistant anemia and myelodysplastic syndromes that may lead to acute myelogenous leukemia. Examination of the bone marrow shows characteristic changes in the megakaryocytes. They are more numerous than usual, small and mononuclear. There may be accompanying erythroid hypoplasia in the bone marrow. Accordingly, in some embodiments, a subject with 5q-myelodysplasia can have dysplastic bone marrow. Subjects with 5q-myelodysplasia can be treated with Lenalidomide (Bennett J et al. (2006). "Lenalidomide in the myelodysplastic syndrome with chromosome 5q deletion". N. Engl. J. Med. 355 (14): 1456-65; Raza et al., (2008), "Phase 2 study of lenalidomide in transfusion-dependent, low-risk, and intermediate-1 risk myelodysplastic syndromes with karyotypes other than deletion 5q". Blood 111 (1): 86-93.)

In some embodiments of all aspects of the present invention, the methods and calmodulin inhibitors and calcium channel blockers as disclosed herein can be used to treat a subject with a ribosomopathy such as Shwachman-Diamond syndrome, for example, where the subject has a mutation in Sbds. In some embodiments, a subject with Shwachman-Diamond syndrome has one or more symptoms selected from pancreatic insufficiency, bone marrow dysfunction, skeletal deformities.

In another embodiment, a calmodulin inhibitor as disclosed herein can be used in a method of treating a subject with a ribosomopathy such as Treacher Collins Syndrome, for example, where the subject has a mutation in TCOF1 (nucleolar). Treacher-Collins syndrome is a condition that is passed down through families (hereditary) that leads to problems with the structure of the face. Treacher-Collins syndrome is caused by a defective protein called treacle. The condition is passed down through families (inherited). This condition may vary in severity from generation to generation and from person to person. Symptoms of Treacher-Collins syndrome include at least one of, but are not limited to: abnormal or almost completely missing outer part of the ears, hearing loss, very small jaw (micrognathia), very large mouth, defect in the lower eyelid (coloboma), scalp hair that reaches to the cheeks, cleft palate. Accordingly, a subject with Treacher Collins Syndrome has one or more craniofacial deformities. While a child with Treacher Collins Syndrome usually will show normal intelligence, diagnosis can be made on the bases of an examination of the infant which may reveal a variety of problems, including: (a) Abnormal eye shape, (b) Flat cheekbones, (c) Clefts in the face, (d) Small jaw, (e) Low-set ears, (f) Abnormally formed ears, (g) Abnormal ear canal, (h) Hearing loss, (i) Defects in the eye (coloboma that extends into the lower lid), (j) Decreased eyelashes on the lower eyelid, (k) genetic tests can help identify gene changes linked to this condition. The diagnosis of Treacher Collins Syndrome also relies upon clinical and radiographic findings, and there is a set of typical symptoms within Treacher Collins Syndrome which can be detected by a critical clinical view. The wide spectrum of diseases which have similar characteristics make it sometimes difficult to diagnose TCS. The OMENS classification was developed as a comprehensive and stage-based approach to differentiate the diseases. This acronym describes five distinct dysmorphic manifestations, namely O; orbital asymmetry, M; mandibular hypoplasia, E; auricular deformity, N; nerve development and S; soft-tissue disease.

Selection of Subjects for Administration with a Pharmaceutical Composition Comprising a Calmodulin Inhibitor In some embodiments, a subject amenable or suitable for treatment with a composition comprising a calmodulin inhibitor as disclosed herein can be selected based on decreased levels of hematopoietic cells and decreased flk1 expression in CD34+ cells, as compared to a control reference normal levels of hematapoeitc cells and flk1 expression level from a normal subject. Additionally, a subject amenable or suitable for treatment with a composition comprising a calmodulin inhibitor as disclosed herein can be selected based on increased levels of p21 expression in CD34+ cells as compared to a control reference p21 expression level. In some embodiments, a subject amenable or suitable for treatment with a composition comprising a calmodulin inhibitor as disclosed herein can be selected based on decreased CD71+ expression and decreased glycophorin A (GPA) expression in CD34+ cells as compared to a control reference CD71+ and GPA expression level, e.g., in a sample from a normal subject not having a ribosomal disorder or ribosomopathy. In some embodiments, the normal reference levels are the based on the level of hematopoetic cells, flk1 expression, CD71+ expression, GPA expression, p21 expression levels in a sample from a normal subject not having a ribosomal disorder or ribosomopathy, or a control cell line, or cells from a normal tissue sample, where in the tissue sample is a biological tissue sample from a tissue matched, and species matched and age matched biological sample.

In some embodiments, the levels of flk1 expression, CD71+ expression, GPA expression, and p21 expression levels are measured in a biological sample comprising hematopoietic cells or erythroid cells or erythroid differentiated cells. In some embodiments, a biological sample obtained from the subject comprises cancer cells, and can be a biological sample which is serum plasma, blood or tissue sample. In alternative embodiments, the biological sample includes, for example blood, plasma, serum, urine, spinal fluid, plural fluid, nipple aspirates, lymph fluid, external secretions of the skin, respiratory, internal and genitoururinary tracts, bile, tears, sweat, saliva, organs, milk cells and primary ascite cells, biopsy tissue sample, an in vitro or ex vivo cultivated biopsy tissue sample.

Pharmaceutical Compositions Comprising a Calmodulin Inhibitor

Another aspect of the present invention relates to pharmaceutical compositions for treatment of diseases or disorders associated with ribosomal proteins or dysfunction or where a subject has a ribosomopathy, e.g., DBA, myelodysplasia, for example, but not limited to 5q-myelodysplasia, Shwachman-Diamond syndrome and Treacher Collins Syndrome. In some embodiments, a pharmaceutical composition of the invention comprises a therapeutically effective amount of at least one calmodulin inhibitor as disclosed herein. In one embodiment, a calmodulin inhibitor is, for example, but not limited to, a phenothiazine compound, e.g., trifluroperazine (TFP), or a naphthalene sulfonamide, such as A-3, W-7 or the like.

A calmodulin inhibitor as disclosed herein can be used in an amount of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some embodiments, a calmodulin inhibitor can be used in an amount of about 0.1 to 1000 µg/kg of body weight or about 1 to 100 µg/kg of body weight or about 10 to 50 µg/kg of body weight. In some embodiments, a calmodulin inhibitor as disclosed herein can be used at a concentration of about 0.001 mg/ml or 0.1 mg/ml or a higher concentration of 0.1 mg/ml. In some embodiments, a pharmaceutical composition comprises at least one calmodulin inhibitor at a concentration of about 0.01 µM to 300 µM, or about 0.1 µM to 150 µM, or about 1 µM to 50 µM, or about 1 µM to 25 µM. The dosage may vary within this range depending upon the dosage form employed and the route of administration utilized.

Depending on routes of administration, one of skill in the art can determine and adjust an effective dosage of a calmodulin inhibitor disclosed herein to a subject such as a human subject accordingly, by determining pharmacokinetics and bioavailability of a calmodulin inhibitor and analyzing dose-response relationship specific to a calmodulin inhibitor in animal models such as a mouse.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

The data obtained from the cell culture assays and animal studies can be used in formulating a range of dosage for use in humans. The therapeutically effective dose can be determined by one of ordinary skill in the art, e.g. using cell culture assays. A dose can be formulated in animal models to achieve a circulating plasma concentration range that includes the IC50 (i.e., the concentration of the therapeutic which achieves a half-maximal inhibition of symptoms) as determined in cell culture by methods disclosed in the Examples. An effective dose of a calmodulin inhibitor can be determined in an animal model by measuring the levels of hemoglobin over the course of treatment with a calmodulin inhibitor as compared to no treatment. In some embodiments, a dosage comprising a calmodulin inhibitor is considered to be effective if the dosage increases hemoglobin levels, red cell number, and/or reduces expression of p21 in CD34+ cells by at least about 15%, at least about 20%, at least about 30%, at least about 40%, at least about 50%, at least about 60%, at least about 70%, at least about 80%, at least about 90%, 95%, 99% or even 100%, as compared to a control (e.g. in the absence of a calmodulin inhibitor).In some embodiments, a therapeutically effective amount of a calmodulin inhibitor administered to a subject is dependent upon factors known to a person of ordinary skill, including bioactivity and bioavailability of a calmodulin inhibitor (e.g. half-life and stability of a calmodulin inhibitor in the body), chemical properties of a calmodulin inhibitor (e.g molecular weight, hydrophobicity and solubility); route and frequency of administration, time of administration (e.g. before or after a meal), and the like. Further, it will be understood that the specific dose of the pharmaceutical composition comprising a calmodulin inhibitor as disclosed herein to provide the therapeutic or prophylactic benefits can depend on a variety of factors including physical condition of the subject (e.g. age, gender, weight), medical history of the subject (e.g. medications being taken, other diseases or disorders) and clinical condition of the subject (e.g. health condition, stage of the disease). The precise dose of a pharmaceutical composition comprising a calmodulin inhibitor can be determined by methods known to a skilled artisan such as pharmacologists and physicians.

According to the invention, a calmodulin inhibitor as disclosed herein can be administered prophylactically or therapeutically to a subject prior to, simultaneously or sequentially with other therapeutic regimens or agents (e. g. multiple drug regimens), in a therapeutically effective amount. In some embodiments, a calmodulin inhibitor administered concurrently with other therapeutic agents can be administered in the same or different compositions. Additional therapeutic agents or regimens include, but are not limited to, steroids, corticosteroids, blood transfusions and bone marrow transplants.

The active ingredients (e.g. a calmodulin inhibitor) of the pharmaceutical composition according to the invention can be administered to an individual by any route known to persons skilled in the art. The routes of administration include intradermal, transdermal (e.g. in slow release formulations), intramuscular, intraperitoneal, intravenous, subcutaneous, oral, buccal, nasal, rectal, epidural, topical, intrathecal, rectal, intracranial, intratracheal and intrathecal and intranasal routes. Any other therapeutically efficacious route of administration can be used, for example absorption through epithelial or endothelial tissues or systemic administration. In addition, a calmodulin inhibitor according to the invention can be administered together with other components of biologically active agents such as pharmaceutically acceptable surfactants, excipients, carriers, diluents and vehicles.

For parenteral (e.g. intravenous, subcutaneous, intramuscular) administration, a calmodulin inhibitor can be formulated as a solution, suspension, emulsion or lyophilized powder in association with a pharmaceutically acceptable parenteral vehicle (e.g. water, saline, dextrose solution) and additives that maintain isotonicity (e g. mannitol) or chemical stability (e.g. preservatives and buffers). The formulation is sterilized by commonly used techniques.

In some embodiments, the route of administration is administration by subcutaneous route. Intramuscular administration is another alternative route of administration. In some embodiments, a pharmaceutical composition comprising a calmodulin inhibitor can be administered as a formulation adapted for systemic delivery. In some embodiments, the compositions can be administered as a formulation adapted for delivery to specific organs, for example but not limited to the liver. In some embodiments, a pharmaceutical composition comprising a calmodulin inhibitor as disclosed herein can be administered as a formulation adapted not to pass through the blood-brain barrier.

Alternatively, in some embodiments, a pharmaceutical composition can be incorporated in a gel, sponge, or other permeable matrix (e.g., formed as pellets or a disk) and placed in proximity to the liver endothelium for sustained, local release. The composition comprising a calmodulin inhibitor can be administered in a single dose or in multiple doses, which are administered at different times.

The exact route of administration as well as the optimal dosages can be determined by standard clinical techniques for each specific case, mainly based on the nature of the disease or disorder and on the stage of this disease. Preferably, the medicament according to the present invention is applied locally or systemically, in particular, orally, intravenously, parenterally, epicutaneously, subcutaneously, intrapulmonarily by inhalation or bronchoalveolar lavage, intramuscularily, intracranially, locally into intervertebral discs or other connective tissues.

As disclosed herein, a pharmaceutical composition comprising an effective amount of at least one calmodulin inhibitor can be administered to a subject for the therapeutic treatment or prevention (e.g. prophylactic treatment) of ribosomal diseases and disorders or ribosomopathies.

In some embodiments, a composition of the invention comprising a calmodulin inhibitor as disclosed herein is formulated for ribosomal diseases and/or ribosomophaties, e.g. DBA, myelodysplasia, for example, but not limited to 5q-myelodysplasia, Shwachman-Diamond syndrome and Treacher Collins Syndrome. In one embodiment, a calmodulin inhibitor as disclosed herein is a derivative, analogue, prodrug, or pharmaceutically acceptable salts thereof.

In some embodiments, a pharmaceutical composition comprising at least one calmodulin inhibitor further comprises a second therapeutic agent. In one embodiment, the second therapeutic agent is a corticosteroid. In some embodiments, the second therapeutic agent is a calcium channel blocker, as disclosed herein.

In prophylactic applications, pharmaceutical compositions (or medicaments) comprising a calmodulin inhibitor can be administered to a subject susceptible to, or otherwise at risk of, a ribosomal disease or disorder and/or ribosomopathy in an amount sufficient to eliminate or reduce the risk or delay the onset of the disease. In one embodiment, a pharmaceutical composition of the invention disclosed herein comprises a calmodulin inhibitor, such as A-3 and/or W-7, or enantiomers, prodrugs, derivatives or pharmaceutically acceptable salts thereof.

In therapeutic applications, according to the invention provided herein, when an effective amount or effective dose of a pharmaceutical composition comprising a calmodulin inhibitor as disclosed herein can be administered to the subject with a ribosomal disease or disorder and/or ribosomopathy so that at least one of the symptoms of such a ribosomal disease can be delayed or inhibited. In some embodiments, administration of an effective amount or effective dose of a pharmaceutical composition comprising a calmodulin inhibitor to a subject with a ribosomal disease or disorder and/or ribosomopathy can inhibit or delay progression of facial abnormalities, and/or other symptoms associated with the ribosomal disease or ribosomopathy. In further embodiments, treating subjects with an effective dose of a pharmaceutical composition comprising a calmodulin inhibitor can prevent or delay a symptom of the ribosomal disease or ribosomopathy in the subject.

In some embodiments, the present invention also provides compositions comprising a calmodulin inhibitor as discussed herein for practicing the therapeutic and prophylactic methods described herein. In some embodiments, combinations of a calmodulin inhibitor and another therapeutic agent can be tailored to be combined in a pharmaceutical composition, where each therapeutics can target a different symptom, a different disease or a different disorder. In further embodiments, a calmodulin inhibitor and another therapeutic can be mixed together in a pharmaceutical composition as disclosed herein. In other embodiments, a calmodulin inhibitor and another therapeutic can be present in a different formulation when combined in a pharmaceutical composition. For example, in one embodiment, a calmodulin inhibitor can be present in a liquid formulation, while another therapeutic can be lypholized into powder. The formulations of different active ingredients in a pharmaceutical composition as disclosed herein (e.g. a calmodulin inhibitor and/or another therapeutics) can be optimized accordingly by various factors such as physical and chemical properties of a drug, bioavailability, route of administration, and whether it is a sustained or a burst release for the drug. Therapeutic and prophylactic compositions of the present invention can further comprise a physiologically tolerable carrier together with a calmodulin inhibitor as disclosed herein, or derivatives, enantiomers, prodrugs or pharmaceutically acceptable salts thereof. In additional embodiments, a calmodulin inhibitor and another therapeutics can employ different physiologically tolerable carriers when combined in a pharmaceutical composition of the invention as disclosed herein.

In some embodiments, a pharmaceutical composition as disclosed herein comprises a calmodulin inhibitor together with other therapeutics and a pharmaceutically acceptable excipient. Suitable carriers for a calmodulin inhibitor of the invention, and their formulations, are described in Remington's Pharmaceutical Sciences, 16th ed., 1980, Mack Publishing Co., edited by Oslo et al. Typically an appropriate amount of a pharmaceutically acceptable salt is used in the formulation to render the formulation isotonic. Examples of the carrier include buffers such as saline, Ringer's solution and dextrose solution. Further carriers include sustained release preparations such as semipermeable matrices of solid hydrophobic polymers, which matrices are in the form of shaped articles, e.g. liposomes, films or microparticles. It will be apparent to those of skill in the art that certain carriers can be more preferable depending upon for instance the route of administration and concentration of a calmodulin inhibitor being administered.

In some embodiments, bioavailability of a calmodulin inhibitor according to the invention can also be improved by using conjugation procedures which increase the half-life of a calmodulin inhibitor in a subject, for example linking a calmodulin inhibitor to polyethylene glycol, as described in WO 92/13095, which is incorporated herein in its entirety by reference.

In some embodiments, bioavailability of a calmodulin inhibitor according to the invention can be also enhanced by encapsulating a calmodulin inhibitor in biocompatible delivery vehicles which increase the half-life of a calmodulin inhibitor in a human body. Exemplary biocompatible delivery vehicles include polymeric vehicles such as PEG-based vehicles, or liposome-based vehicles.

In some embodiments, a calmodulin inhibitor can be dissolved or dispersed as an active ingredient in the physiologically tolerable carrier to increase the half-life of a calmodulin inhibitor in a subject.

The preparation of a pharmacological composition that contains active ingredients (e.g. a calmodulin inhibitor) dissolved or dispersed therein is well understood in the art and need not be limited based on formulation. Typically such compositions are prepared as injectable either as liquid solutions or suspensions, however, solid forms suitable for solution or suspension in liquid prior to use can also be prepared. The preparation can also be emulsified or presented as a liposome composition. In some embodiments, a calmodulin inhibitor can be mixed with excipients which are pharmaceutically acceptable and compatible with the active ingredient and in amounts suitable for use in the therapeutic methods described herein. In addition, if desired, the composition comprising a calmodulin inhibitor can contain minor amounts of auxiliary substances such as wetting or emulsifying agents, pH buffering agents and the like which enhance the effectiveness of the active ingredient.

Physiologically tolerable carriers (i.e. physiologically acceptable carriers) are well known in the art. Selection of pharmaceutically acceptable carriers can be accomplished by means of administration by a skilled artisan. For example, if the composition is orally administered, it can be formulated in coated tablets, liquids, caplets and so forth. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. For topical application, the carrier may be in the form of, for example, and not by way of limitation, an ointment, cream, gel, paste, foam, aerosol, suppository, pad or gelled stick. In some embodiments, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997). An inhibitor of calmodulin as disclosed herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

A skilled artisan will be able to determine the appropriate way of administering pharmaceutical compositions comprising at least one LSF inhibitor as disclosed herein in view of the general knowledge and skill in the art.

Treatment Regimes

Another aspect of the present invention relates to methods for therapeutic and prophylactic treatment of diseases or disorders, where inhibition of calmodulin is desirable for the treatment or prevention of a ribosomal disorder or a ribosomopathy. The methods comprise administering to a subject in need thereof a pharmaceutical composition comprising a therapeutically effective amount of at least one calmodulin inhibitor selected from for example, any, or a combination, of compounds such as TFP, A-3, W-7, A-7 and CGS-9343, and analogues and variants as disclosed herein.

In one embodiment, Diamond-Blackfan anemia (DBA) is treated or prevented by the methods and compositions of the present invention with a calmodulin inhibitor as disclosed herein.

Effective doses of the pharmaceutical composition comprising a calmodulin inhibitor as disclosed herein, for the treatment of ribosome protein diseases or disorders or associated with a ribosomopathy depend upon many different factors, including means of administration, physiological state of the subject, whether the subject is human or an animal, other medications administered, and whether treatment is prophylactic or therapeutic. Depending on the clinical condition of a subject, dosage and frequency of pharmaceutical compositions of the present invention can be adjusted accordingly over time by one of the skill in the art, e.g. physicians.

In therapeutic applications, a relatively high dosage in relatively short intervals is sometimes required until progression of the disease is reduced or terminated, or until the subject shows partial or complete amelioration of symptoms of disease. Thereafter, the subject can be administered a prophylactic regime. For example, subjects with DBA can be treated with a calmodulin inhibitor as disclosed herein at an effective dose in a therapeutic regimen accordingly to decrease the p21 levels and or p53 levels back to a normal level, and then be administered a maintenance dose, e.g., prophylactically. In some embodiments, a calmodulin inhibitor as disclosed herein can be administered to subjects prior to, concurrently with, or sequentially to treatment with a corticosteroid, and/or when the subject us undergoing an adjuvant therapy, such as a blood transfusion and/or bone marrow transplant. In some embodiments for example, a DBA subject which is selected for other therapeutic procedures or surgeries, such as blood transfusions and/or bone marrow transplant, can be subjected to a treatment with a calmodulin inhibitor as disclosed herein. For example, a pharmaceutical composition of the invention can be administered prior to, during or after therapeutic procedures. Route of administration can vary with therapeutic procedures or surgeries and can be determined by a skilled artisan. In yet another embodiment, compositions and methods of the invention can be used as an adjuvant therapy.

In some embodiments, the subject is a human, and in alternative embodiments the subject is a non-human mammal. Treatment dosages need to be titrated to optimize safety and efficacy. The amount of a calmodulin inhibitor depends on the stage of the disease, as well as the species.

In some embodiments, a calmodulin inhibitor can be administered to a subject in a pharmaceutical composition comprising an amount of a calmodulin inhibitor of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some embodiments, a calmodulin inhibitor can be used in an amount of about 0.1 to 1000 µg/kg of body weight or about 1 to 100 µg/kg of body weight or about 10 to 50 µg/kg of body weight. In some embodiments, a calmodulin inhibitor can be administered at a concentration of about 0.001 mg/ml or 0.1 mg/ml or a higher concentration of 0.1 mg/ml. In alternative embodiments, a pharmaceutical composition comprises at least one calmodulin inhibitor at a concentration of about 0.01 µM to 300 µM, or about 0.1 µM to 150 µM, or about 1 µM to 50 µM, or about 1 µM to 25 µM.

The inventors have demonstrated herein that a calmodulin inhibitor reverses the vascular deformations and morphology in vivo of rps29−/− zebrafish embryos at a concentration of between 5-50 µg/mL, and that TFP restored the percentage of CD71+ cells in a erythroid cell population at between 5-20 µM in vitro. Accordingly, in some embodiments, a calmodulin inhibitor as disclosed herein can be administered to a subject according to the methods as disclosed herein in an effective dose to increase the levels of CD71+ cells in an erythroid cell population obtained from the subject by at least about 1%, at least about 2%, at least about 3%, at least about 5%, at least about 10%, at least about 15%, least about 20%, at least about 30%, at least about 40%, at least about 50%, or more than 50%, as compared to in the absence of a calmodulin inhibitor.

The inventors have demonstrated herein that the calmodulin inhibitor A-3, at between 1-50 µM decreased the levels of p21 in CD34+ cells present in a erythroid cell population in vitro. Accordingly, in another embodiment, a calmodulin inhibitor as disclosed herein can be administered to a subject according to the methods as disclosed herein in an effective dose to decrease the levels of p21 expression in CD34+ cells present in an erythroid cell population obtained from the subject by at least about 1%, at least about 2%, at least about 3%, at least about 5%, at least about 10%, at least about 15%, least about 20%, at least about 30%, at least about 40%, at least about 50%, at least about 60%, at least about 70%, at least about 80%, at least about 90%, at least about 95%, at least about 98%, at least about 99%, or more than 99%, as compared to in the absence of a calmodulin inhibitor.

Generally, effective dosages and dosing schedules can be adjusted based on, for example, the outcome of the treatment such as whether the subject has reduced symptoms of anemia, and/or whether at least one of the symptoms associated with the ribosomal protein disorder, such as DBA is reduced. In accordance with the teachings provided herein, the effectiveness of the treatment can be monitored by obtaining a biological sample from a subject, e.g. a blood serum sample, and determining the level of biomarkers for DBA, such as percentage of CD71+ cells in a erythroid cell population and/or level of p21 in CD34+ cells, using methods well known in the art and the diagnostic methods as disclosed later herein.

In some embodiments, the daily dose administered to a subject in a form of a bolus composition comprising a calmodulin inhibitor can be given in a single dose, in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease. It is also within the skill of the art to start doses at levels lower than required to achieve the desired therapeutic effect and to gradually increase the dosage until the desired effect is achieved.

The pharmaceutical compositions comprising at least one calmodulin inhibitor as disclosed herein can be administered by parenteral, topical, intravenous, oral, subcutaneous, intraperitoneal, intranasal or intramuscular means for prophylactic and/or therapeutic treatment. For example, for treatment of cancer, e.g., HCC, a pharmaceutical composition comprising at least one LSF inhibitor can be injected systemically such as by intravenous injection, or by injection or application to the relevant site, such as by direct injection into a tumor, or direct application to the site when the site is exposed in surgery. Other routes of administration of a calmodulin inhibitor as disclosed herein are intramuscular (i.m.), intravenous (i.v.), subcutaneous (s.c.), or orally, although other routes can be equally effective. Intramuscular injection is most typically performed in the arm or leg muscles. In some methods, a calmodulin inhibitor as disclosed herein can be administered as a sustained release composition or device, such as a Medipad™ device.

In some embodiments, a calmodulin inhibitor as disclosed herein can optionally be administered in combination with other agents that are at least partly effective in treatment of ribosomal protein diseases and disorders, such as blood transfusions, bone marrow transplants and the like. In other embodiments, a calmodulin inhibitor of the invention can be administered prior to, concurrently, or after administration of another therapeutics that targets another disease or disorder, or a different symptom.

In various embodiments, a calmodulin inhibitor can be a pro-drug, where it is activated by a second agent. Accordingly, in such embodiments, administration of such the second agent which activates the pro-drug of the calmodulin inhibitor into its active form can be administered the same time, concurrent with, or prior to, or after the administration of the pharmaceutical composition comprising a calmodulin inhibitor as disclosed herein.

In some embodiments, a calmodulin inhibitor as disclosed herein is often administered as pharmaceutical compositions comprising an active therapeutic agent, i.e. a calmodulin inhibitor, and a variety of other pharmaceutically acceptable components. See Remington's Pharmaceutical Science (15th ed., Mack Publishing Company, Easton, Pa., 1980). The formulation of the compositions depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, non-therapeutic, non-immunogenic stabilizers and the like. However, some reagents suitable for administration to animals may not necessarily be used in compositions for human use.

For parenteral administration, a calmodulin inhibitor as disclosed herein can be administered as injectable dosages of a solution or suspension of the substance in a physiologically acceptable diluent with a pharmaceutical carrier which can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Other mode of administration includes systemic delivery. In some embodiments, at least one calmodulin inhibitor as disclosed herein can be injected systemically such as by intravenous injection, or by injection or application to the relevant site, such as direct application to the site when the site is exposed in surgery. In some embodiments, a pharmaceutical composition of the invention can be formulated in a tablet and used orally for systemic administration. In various embodiments, pharmaceutical compositions of the invention can further comprises non-active ingredients (i.e. ingredients that have no therapeutic values for treatment of diseases, disorders or symptoms), such as physiologically acceptable carriers.

In various embodiments, modification of a calmodulin inhibitor by addition of a polymer is specifically contemplated, for example, using a covalent attachment to a polymer. In other embodiments, a calmodulin inhibitor can be mixed with or encapsulated in a biocompatible polymer.

In another aspect, biodegradable or absorbable polymers can provide extended, often localized, release of a calmodulin inhibitor as disclosed herein. The potential benefits of an increased half-life or extended release for a therapeutic agent are clear. A potential benefit of localized release is the ability to achieve much higher localized dosages or concentrations, for greater lengths of time, relative to broader systemic administration, with the potential to avoid possible undesirable side effects that may occur with systemic administration.

Bioabsorbable polymeric matrix suitable for delivery of a calmodulin inhibitor as disclosed herein, or variants or fragments or derivatives thereof can be selected from a variety of synthetic bioabsorbable polymers, which are described extensively in the literature. Such synthetic bioabsorbable, biocompatible polymers, which may release proteins over several weeks or months can include, for example, poly-hydroxy acids (e.g. polylactides, polyglycolides and their copolymers), polyanhydrides, polyorthoesters, segmented block copolymers of polyethylene glycol and polybutylene terephtalate (POLYACTIVE™), tyrosine derivative polymers or poly(ester-amides). Suitable bioabsorbable polymers to be used in manufacturing of drug delivery materials and implants are discussed e.g. in U.S. Pat. Nos. 4,968,317, 5,618,563 (which are incorporated herein in their entirety by reference), among others, and in "Biomedical Polymers" edited by S. W. Shalaby, Carl Hanser Verlag, Munich, Vienna, New York, 1994 and in many references cited in the above publications. The particular bioabsorbable polymer that should be selected will depend upon the particular patient that is being treated.

The methods of the present invention also are useful for monitoring a course of treatment being administered to a subject. The methods can be used to monitor both therapeutic treatment on symptomatic subject and prophylactic treatment on asymptomatic subject.

A treatment administered to a subject is considered to be effective if the level of expression of p21 in CD34+ cells present in a biological sample obtained from the subject is decreased by at least about 20%, at least about 30%, at least about 40%, at least about 50%, at least about 60%, at least about 70%, at least about 80%, at least about 90%, at least about 95%, at least about 98%, about 99% or about 100% as compared to a reference level, or in the absence of the calmodulin inhibitor. In such embodiments, the reference level is the measurement of p21 in CD34+ cells present in a biological sample obtained from the subject at a previous time point, e.g., who has not been administered the calmodulin inhibitors. Based on the outcome of treatment, the dosage and frequency of administration using the methods and compositions as disclosed herein can be adjusted accordingly by one of skill in the art.

One can use any immunoassay to determine the level of p21 expression in CD34+ cells in a biological sample, such as ELISA or immunohistochemical methods which are commonly known in the art and are encompassed for use in the present invention.

Kits

Another aspect of the present invention relates to a kit comprising one or more calmodulin inhibitors as disclosed herein, and instructions for carrying out a method as disclosed herein.

In some embodiments, a kit can optionally additionally comprise reagents or agents for measuring the level of p21 expression in a biological sample from the subject, such as, for example, a blood sample, for example to identify the efficacy of treatment with the calmodulin inhibitor as disclosed herein. Such agents are well known in the art, and include without limitation, labeled antibodies that specifically bind to p21 protein and/or mRNA and the like. In some embodiments, the labeled antibodies are fluorescently labeled, or labeled with magnetic beads and the like. In some embodiments, a kit as disclosed herein can further comprise at least one or more reagents for profiling and annotating a biological sample from the subject in high throughput assay.

In some embodiments, the kit can further comprise instructions for administering a composition comprising a calmodulin inhibitor to a subject in need thereof, e.g., with a ribosomal protein disease or disorder, e.g., DBA and instructions for doses and the like.

In addition to the above mentioned component(s), the kit can also include informational material. The informational material can be descriptive, instructional, marketing or other material that relates to the methods described herein and/or the use of the components for the assays, methods and systems described herein.

In some embodiments, the methods and kits comprising a calmodulin inhibitor as disclosed herein can be performed by a service provider, for example, where an investigator or physician can send the biological sample to a diagnostic laboratory service provider to measure the level of p21 expression in CD34+ cells, and/or the level of CD71+ cells in a erythroid cell population present in the biological subject from the subject. In such an embodiment, after performing the such measurements, the service provider can provide the investigator or physician a report of the efficacy of the calmodulin inhibitor and/or report if the subject is a suitable or amenable to be treated with a calmodulin inhibitor according to the methods and composition as disclosed herein.

In alternative embodiments, a service provider can provide the investigator with the raw data of the levels of p21 p53 expression in CD34+ cells, and/or the levels of CD71+ cells in a erythroid cell population present in the biological subject from the subject and leave the analysis to be performed by the investigator or physician. In some embodiments, the report is communicated or sent to the investigator via electronic means, e.g., uploaded on a secure web-site, or sent via e-mail or other electronic communication means. In some embodiments, the investigator can send the samples to the service provider via any means, e.g., via mail, express mail, etc., or alternatively, the service provider can provide a service to collect the samples from the investigator and transport them to the diagnostic laboratories of the service provider. In some embodiments, the investigator can deposit the samples to be analyzed at the location of the service provider diagnostic laboratories. In alternative embodiments, the service provider provides a stop-by service, where the service provider send personnel to the laboratories of the investigator and also provides the kits, apparatus, and reagents for performing the assays to measure the levels of p21 expression in CD34+ cells, and/or the level of CD71+ cells in a erythroid cell population present in the biological subject from the subject as disclosed herein in the investigators laboratories, and analyses the result and provides a report to the investigator for each subject, and leaves the physician to make appropriate recommendations of treatment, and dose to administer the subject with a composition comprising a calmodulin inhibitor according to the methods as disclosed herein.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Although any known methods, devices, and materials may be used in the practice or testing of the invention, the methods, devices, and materials in this regard are described herein.

The examples presented herein relate to methods and compositions comprising at least one calmodulin inhibitor as disclosed herein for treatment of a ribosomal disorder or ribosomapathy, for example, but not limited to DBA. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Materials and Methods

Embryo Manipulation and Chemical Treatment

Fish were maintained under approved laboratory conditions. Studies were performed on AB wildtype strains and hi2903, an insertional mutant in the first intron of ribosomal protein S29 (rps29). Embryos were subjected to chemicals diluted in E3. For screening, chemicals from ICCB Biomol Known Bioactive, Sigma, and Lopac libraries were tested at 1:300 dilutions from library stock. Compounds were tested in two independent experiments of 20 embryos each, so approximately 10 mutant embryos were scored per chemical. The following chemicals were diluted in DMSO or water and tested in doses from 5-50 µg/mL: A-3 (Enzo), W-7 (Tocris), A-5 (Tocris), W-5 (Enzo), CGS-9343B (Tocris) and trifluorperazine (Enzo). Nimodipine (Enzo) was diluted in DMSO and tested in doses from 1.5 to 20 µg/mL. SNAP (Cayman) was diluted in DMSO and tested in doses from 0.5 to 5 µg/mL. YS-035 (Sigma) was diluted in water and treated in doses from 0.8 to 8 µg/mL. Vinpocetine (Enzo) was diluted in ethanol and treated in doses from 0.3 to 3 µg/mL.

In Situ Hybridization and Benzidine Staining

Whole-mount in situ hybridization (ISH) was performed as described (Thisse and Thisse, 2008). Antisense probes were synthesized from digested plasmid. O-Dianisidine was performed as described previously (Paffett-Lugassy and Zon, 2005).

Cell Culture and Infection

A549 and CD34$^+$ cells were infected with previously characterized lentiviral shRNA targeting RPS19 (Dutt et al., 2011). Unless otherwise noted, drugs were added one day post infection, and cells were collected for analysis 3-6 days post infection.

Flow Cytometry and Immunofluorescence

For flow cytometry based measurement of protein levels, cells were fixed in 2% paraformaldehyde for 15 minutes at 37° C., and methanol was added for overnight incubation at 4° C. Cells were incubated for one hour in 1:100 diluted p21 primary antibody (Cell Signaling 12D1) followed by one hour in conjugated secondary antibody and 1:50 diluted p53-conjugated antibody (Cell Signaling 1C12). Immunofluorescence staining was performed as previously described (Dutt et al., 2011).

Example 1

Ribosomal protein mutations are common in patients with Diamond Blackfan anemia (DBA), who have red cell aplasia and craniofacial abnormalities. The inventors have previously characterized a zebrafish mutant in rps29, a ribosomal protein in the small subunit. Rps29$^{-/-}$ embryos have morphological defects in the head, as well as decreased hematopoietic stem cells, hemoglobin, and staining of endothelial markers. Consistent with other models of DBA, knockdown of p53 near completely rescues the rps29 mutant phenotype. To identify chemicals that could rescue the rps29 mutant phenotype, the inventors performed an in vivo chemical screen. Calmodulin inhibitors were found to rescue morphological, endothelial, and hemoglobin phenotypes.

Zebrafish RPS29 Mutants have p53-Dependent Hematopoietic Phenotypes

The inventors zebrafish work has focused on the rps29 mutant (Amsterdam et al., 2004). The inventors have previously reported that Rps29 mutant embryos was initially have hematopoietic and endothelial defects (Burns et al., 2009). Rps29$^{-/-}$ embryos have a defect in arterial specification, leading to decreased hematopoietic stem cells and decreased flk1 expression in the intersegmental vessels at 24 hours post fertilization (hpf). Primitive erythropoiesis is specifically affected, as rps29$^{-/-}$ embryos have less hemoglobin whereas primitive myelopoiesis is unaffected. The rps29 mutant embryos have increased apoptosis, as seen by changes in head morphology and TUNEL staining. Microarray analysis demonstrated an activation of p53 and its targets in the mutant embryo. When a p53 mutation was crossed into the background of the rps29 mutant, all of the hematopoietic and apoptotic phenotypes were rescued. Herein, the inventors demonstrate a critical role of p53 activation in rps29 mutant phenotypes. This characterization of the rps29 mutant and identification of a p53-dependent mechanism was recently published in the Journal of Experimental Hematology (Taylor et al., 2012, which is incorporated herein in its entirety by reference).

Chemical Screen finds Calmodulin Inhibitors Rescue rps29$^{-/-}$ Defects

A screen was performed to identify chemicals that could rescue the endothelial and morphological defects of the rps29$^{-/-}$ mutant embryo (FIG. 1A). Rps29$^{+/-}$ fish were incrossed, and embryos were collected for treatment at bud stage (10 hpf). Embryos were treated from bud to 23 hpf with compounds of known bioactivity. After being scored for rescue of head morphology, embryos were fixed at 24 hpf for in situ hybridization of flk1 and rps29. Embryos without rps29 staining (rps29$^{-/-}$ mutants) were scored for rescue of flk1 intersegmental vessel staining.

In total, 600 compounds were screened for rescue of both phenotypes; endothelial or morphological defects of the rps29$^{-/-}$ mutant embryo. These compounds include the entirety of the ICCB Known Bioactives library, as well as some compounds in Sigma and Lopac chemical libraries. Fifteen compounds (2.5%) were validated to rescue flk1 expression, and one compound was validated to rescue the head morphological defect.

Figure 1B:
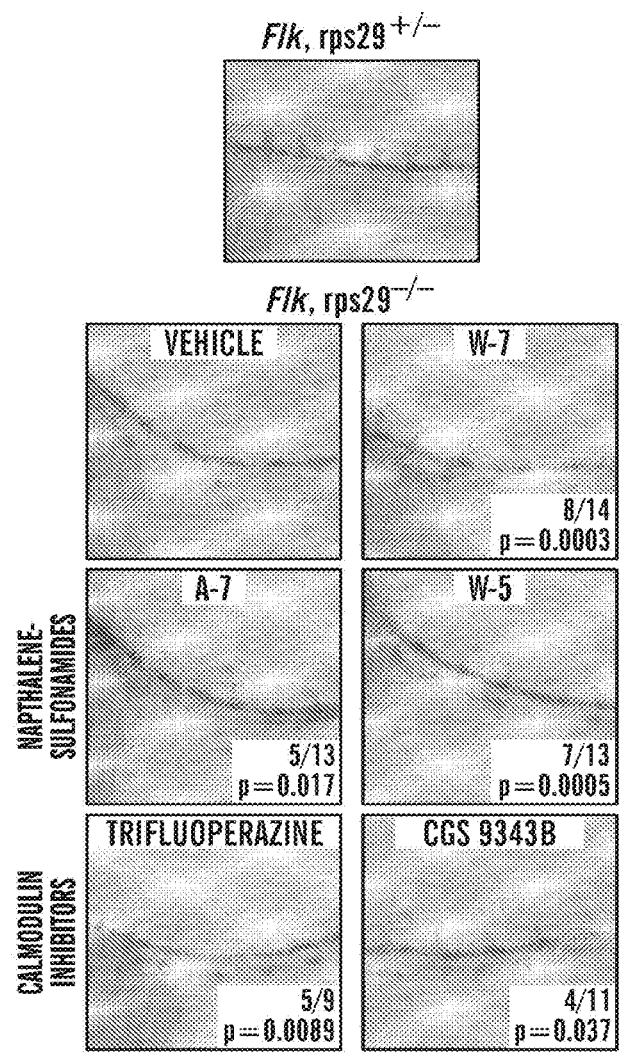

One of the compounds identified in the screen to rescue flk1 expression was W-7, a naphthalenesulfonamide that inhibits calmodulin (FIG. 1B). Other naphthalenesulfonamides known to inhibit calmodulin, including A-7 and W-5, and were demonstrated to also rescue the vasculature defect. To verify that calmodulin was the relevant target, the inventors tested known calmodulin inhibitors of different classes. Several additional calmodulin inhibitors rescued flk1 expression, including CGS-9343B and members of the phenothiazine family such as trifluoperazine (TFP). These compounds are structurally distinct from the W-7 class, demonstrating that calmodulin is the target for rescue of flk1 expression and that inhibition of calmodulin results in rescuing ribosomal protein deficiency. A-3, a structural derivative of W-7 and known calmodulin inhibitor, rescued the morphology of the rps29$^{-/-}$ head (FIG. 2C). Treatment with A-3 or W-7 also rescues hemoglobin levels in the rps29 mutant embryos (FIG. 2C).

Example 2

Inhibition of Calmodulin Dependent Phosphodiesterase Rescues Vasculature

Figure 1C:
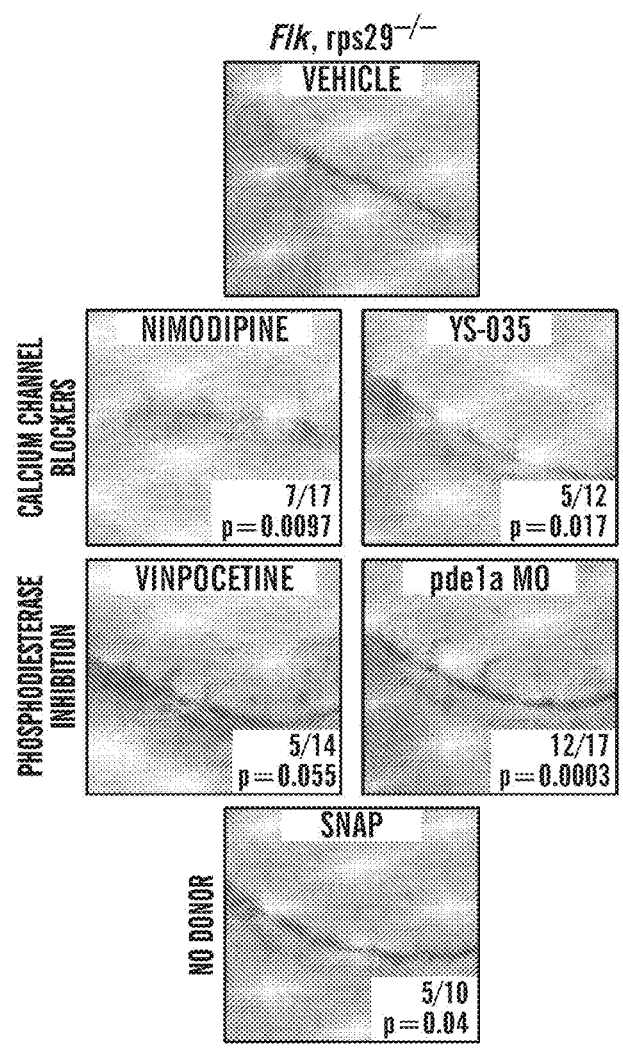

Other compounds identified in the screen targeted calmodulin-related pathways (FIG. 1C). $Ca^{2+}$ channel blockers Nimodipine and YS-035 both rescued the vasculature defect. Many enzymes in the cell require calmodulin, including calmodulin-dependent kinases (CaMKs, myosin light chain kinase) and phosphatases (calcineurin) and other enzymes (including phosphodiesterase 1) (Chin and Means, 2000; Inagaki et al., 1986). Vinpocetine, an inhibitor of calmodulin-dependent phosphodiesterase1 (pde1), was a hit in the screen. Next, the inventors to assess if pde1 was the relevant enzyme being targeted by the calmodulin inhibitors. To confirm pde1 as the relevant target, the inventors injected a morpholino targeting pde 1a into $rps29^{-/-}$ embryos. Pde 1a knockdown also rescued the vasculature (FIG. 1C). Phosphodiesterases can negatively regulate nitric oxide (NO) signaling, as they degrade cGMP, a mediator of the NO signaling pathway. NO signaling can increase artery specification in wildtype embryos (North et al., 2009). The NO donor, SNAP, rescued flk1 intersegmental vessel staining in the mutant embryo (FIG. 1C), and other NO activators were also identified in the screen (data not shown).

Example 3

Figure 2A:
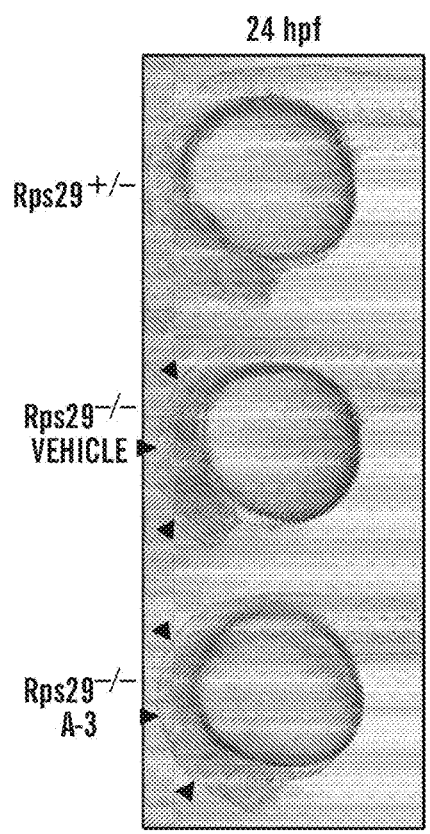
FIGS. 2A-2C shows the chemical compound A-3 rescues morphological and hemoglobin defects in rps29 mutant embryo.
Figure 2C:
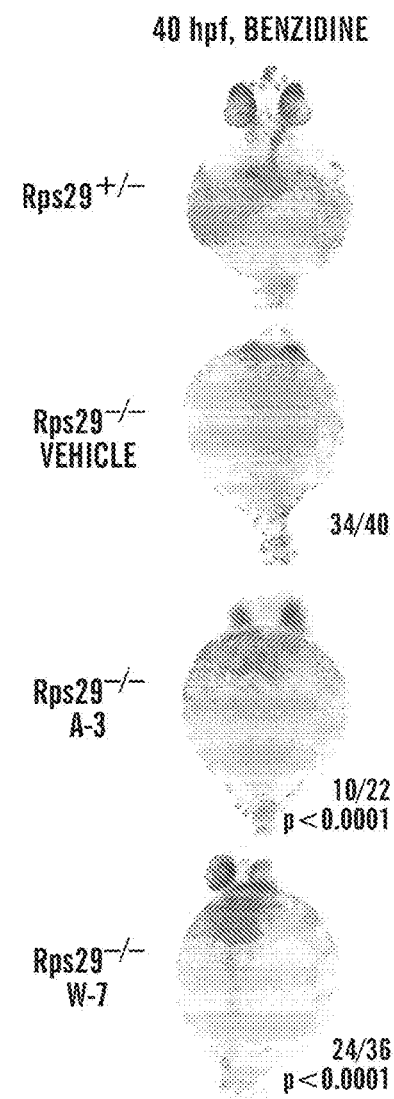
Figure 2B:
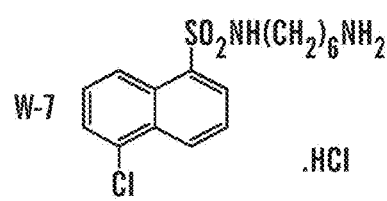
Figure 2B:
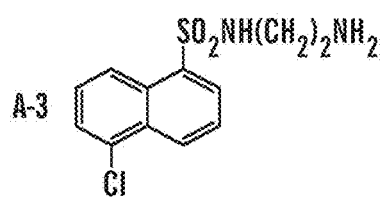

Calmodulin Inhibitor Rescues Head and Hemoglobin Defects in $rps29^{-/-}$ Embryos Of all the chemicals screened, only one rescued the morphology of the $rps29^{-/-}$ head, A-3 (FIG. 2A). A-3 is a structural derivative of W-7 (FIG. 2B) and known calmodulin inhibitor. Treatment with A-3 can also rescue hemoglobin levels in the rps29 mutant embryos (FIG. 2C). A-3 treatment did not rescue the vasculature (data not shown), but has previously been shown a less effective inhibitor of calmodulin dependent PDE1 than other calmodulin-dependent enzymes (Inagaki et al., 1986). This suggests that the mechanism by which A-3 rescues the head and red blood cell defects is independent of pde1.

Calmodulin Inhibition Attenuates p21 Protein upon RPS19 Knockdown

Figure 3F:
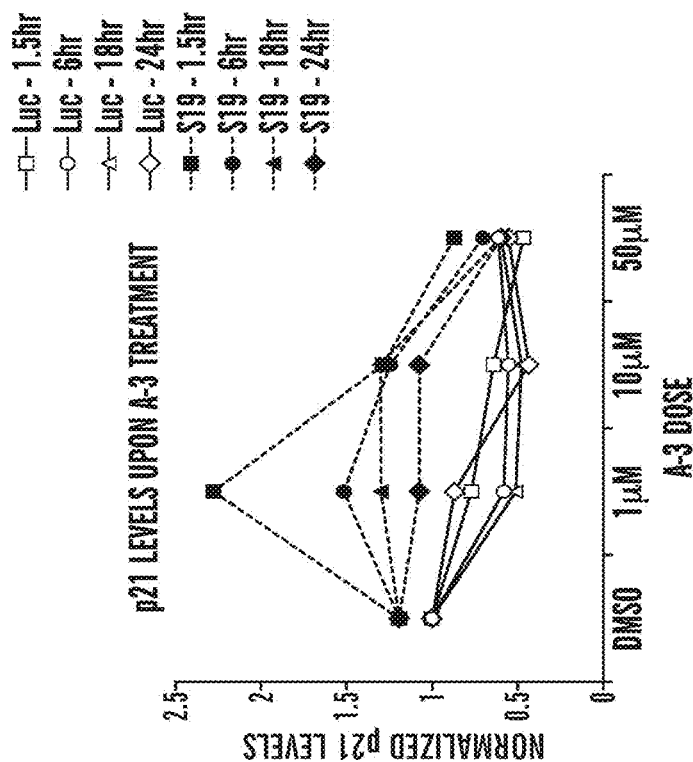
Figure 3E:
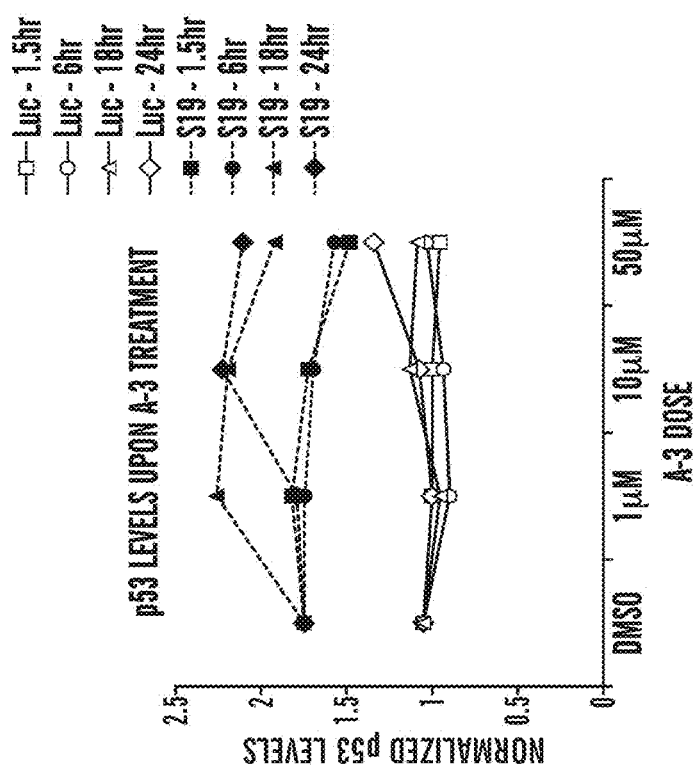

The inventors next tested the effect of calmodulin inhibitors in A549 cells, where p53 is not mutated and is induced upon ribosomal protein knockdown (Fumagalli et al., 2009). A549 cells were infected with control or RPS19 shRNA and treated with A-3 or TFP 24 hours post infection. Cells were analyzed 3-6 days post infection. Although p53 protein levels were still increased upon rps19 knockdown, both drugs caused a statistically significant decrease of p21 protein as measured by flow cytometry (FIG. 3A-3D). Studies with shorter treatment windows demonstrated that within 1.5 hours of treatment, p21 protein levels begin to decrease (FIG. 3E-3F). In addition, removal of drug leads to an increase in p21 levels within 24 hours (data not shown). These data demonstrate that chemical inhibition of calmodulin inhibits p21 activation.

Example 4

Treatment with A-3 Inhibits p53 and p21 Nuclear Localization

Previous research has shown a role for calmodulin in p21 nuclear localization (Rodriguez-Vilarrupla et al., 2005), so the inventors assessed if calmodulin inhibitors could affect protein localization of p53 and p21 upon ribosomal protein knockdown.

For their mechanistic studies, the inventors used A549 cells, a lung cancer cell line where p53 is not mutated and is induced upon ribosomal protein knockdown (Fumagalli et al., 2009). Induction of p53 leads to its accumulation in the nucleus and increased transcription of its targets, including p21.

Figure 4A:
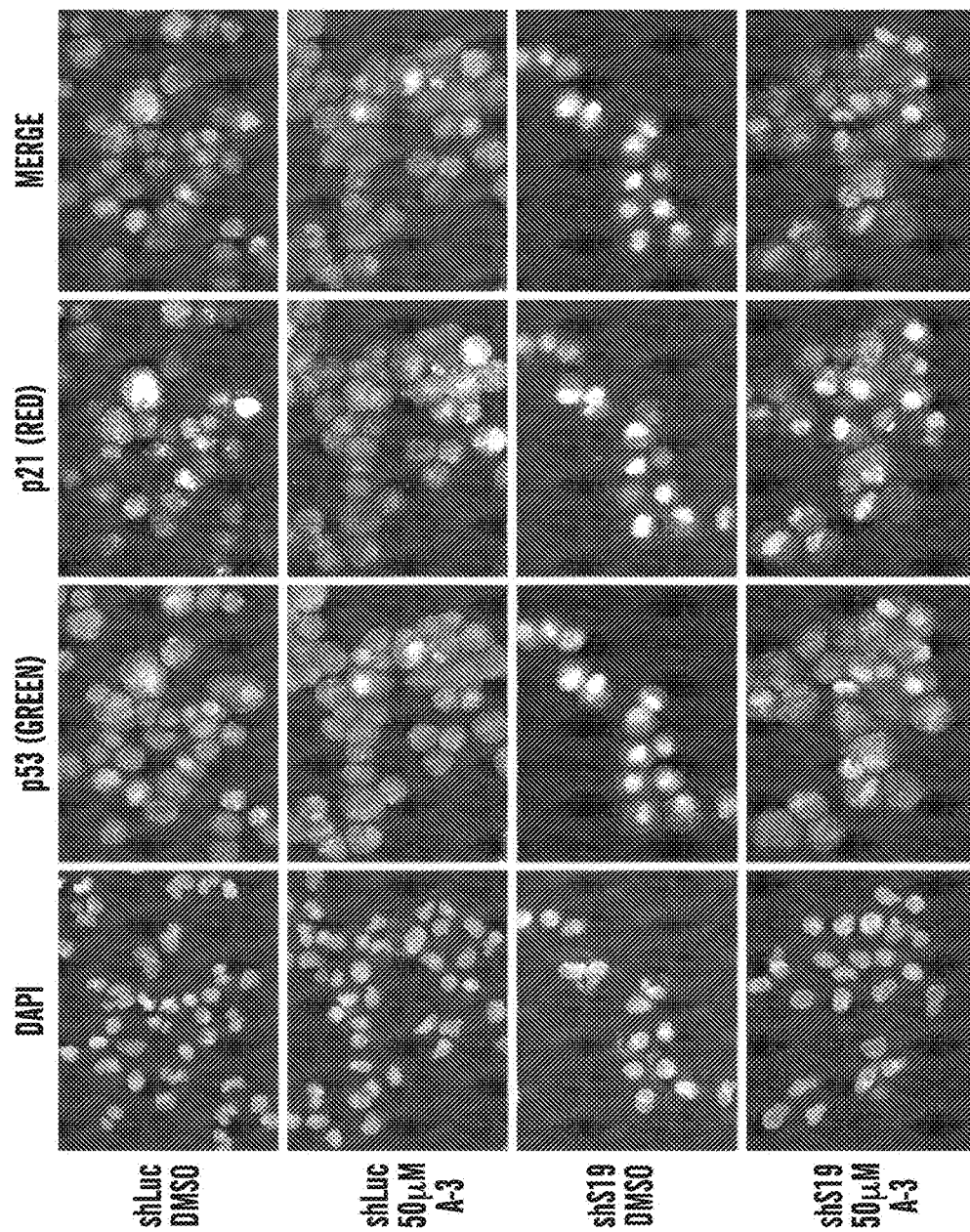
FIGS. 4A-4D show treatment with A-3 inhibits p53 and p21 nuclear localization upon rps19 knockdown.
Figure 4B:
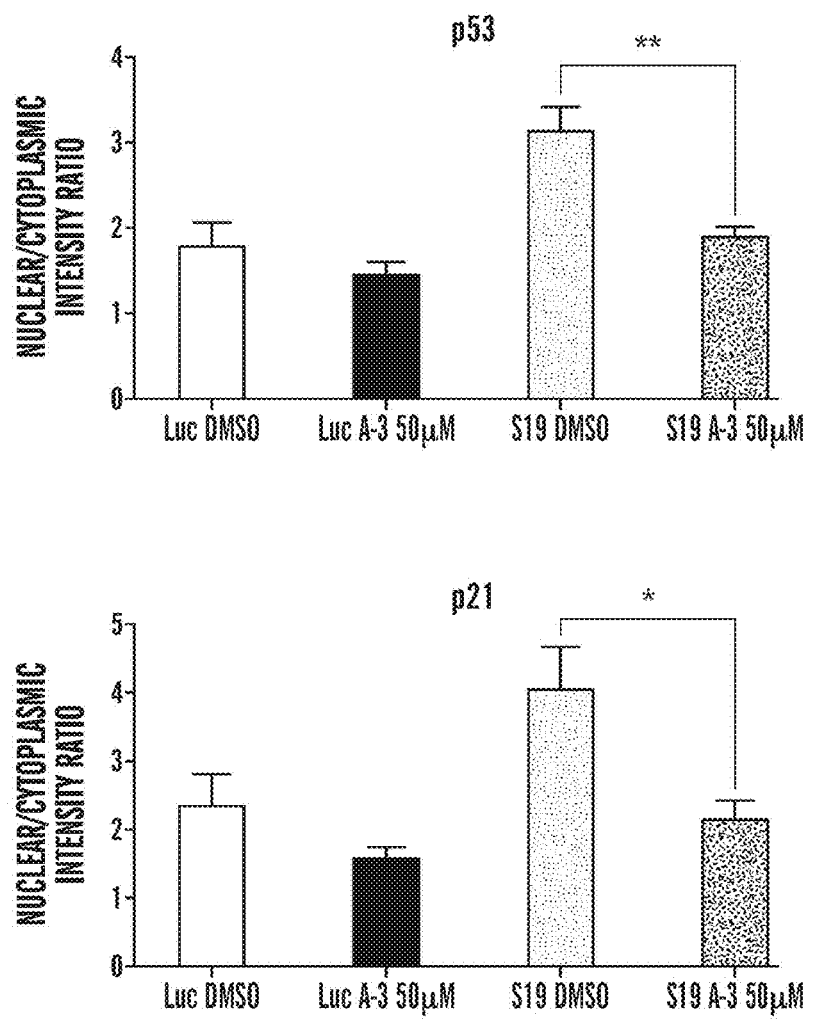
Figure 4C:
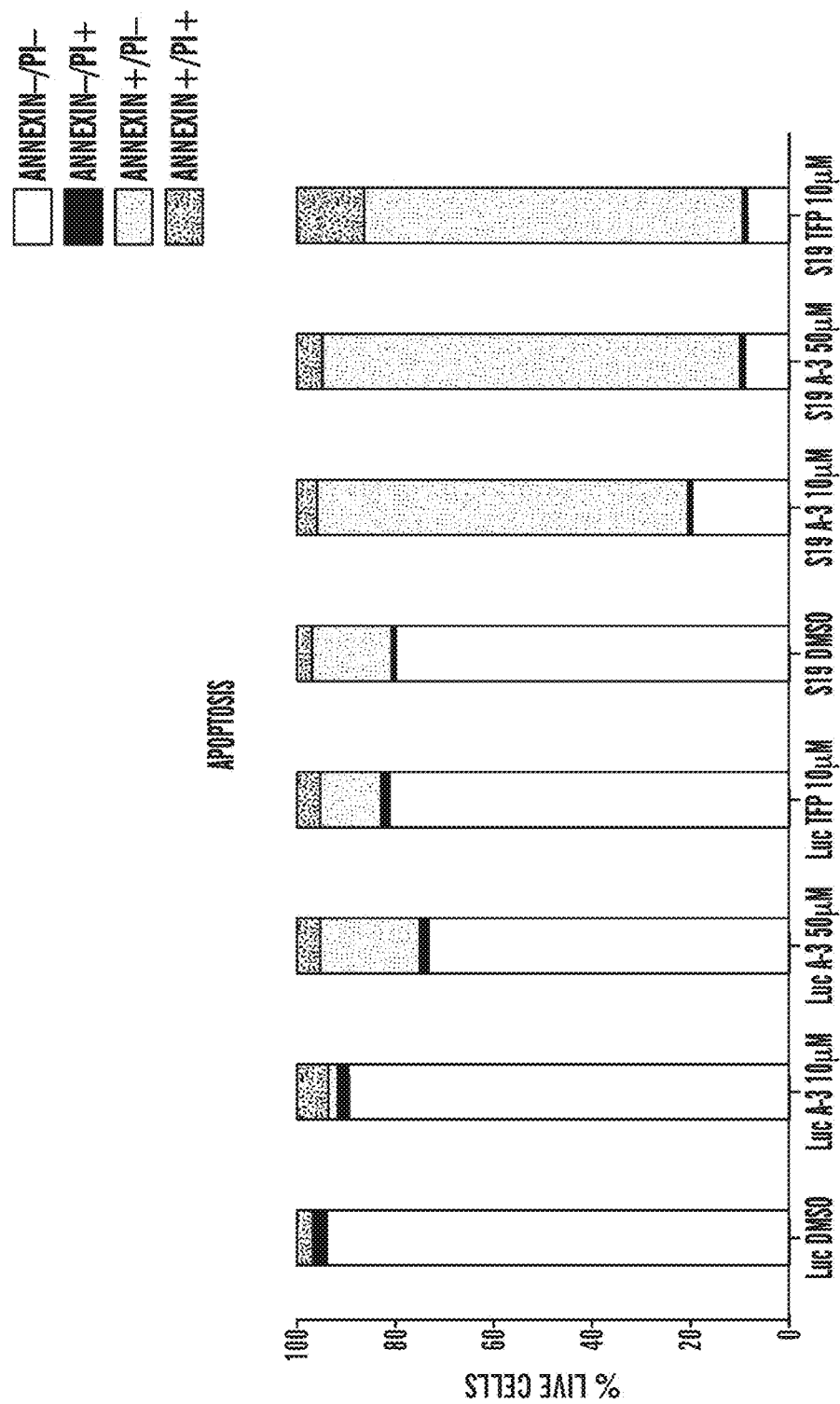
Figure 4D:
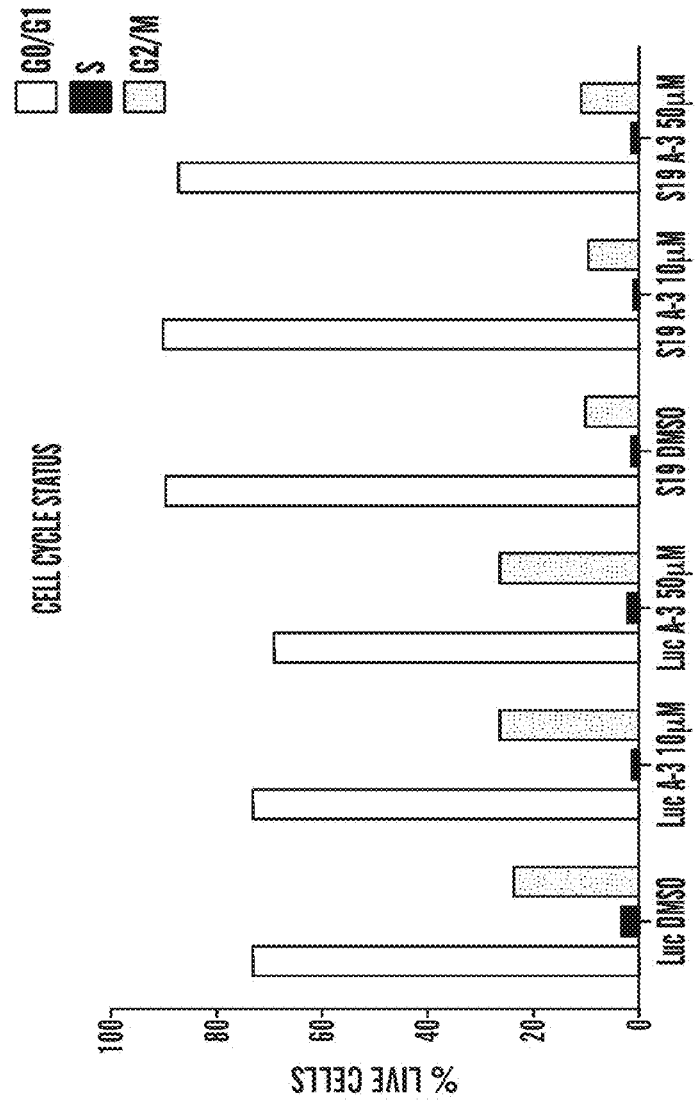

Immunofluorescence staining for p53 and p21 was performed on chemically treated cells (FIG. 4A). For 10-15 cells per condition, average nuclear and cytoplasmic intensity was determined using ImageJ. By these methods, the inventors demonstrate that treatment with A-3 upon RPS19 knockdown decreased p53 and p21 nuclear staining intensity (p53: p=0.00028; p21: p=0.007) (FIG. 4B). The same effect was seen with TFP (data not shown), demonstrating that calmodulin inhibition can affect p53 and p21 nuclear localization. Cells treated with A-3 and TFP actually have increased annexin V positivity (FIG. 4C), with no obvious effect on the RPS19 shRNA induced cell cycle arrest (FIG. 4D).

Figure 5A:
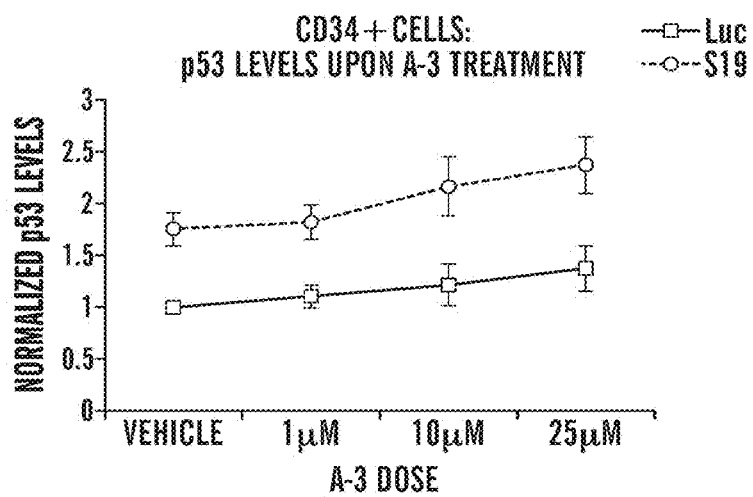
FIGS. 5A-5B show A-3 decreases p53 and p21 in $CD34^+$ cells.
Figure 5B:
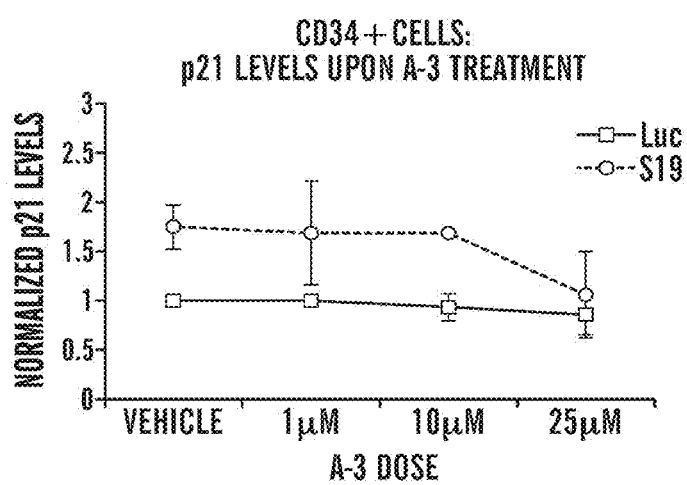

Calmodulin Inhibitors Prevent p53 Function and Nuclear Accumulation upon RPS19 Knockdown A549 cells were infected with control or RPS19 shRNA and subsequently treated with A-3 or TFP. When either calmodulin inhibitor was added, there was a decrease of p21 protein without a matching decrease of p53 (FIG. 5A). Immunofluorescence staining to assay p53 localization was also performed. The inventors demonstrate that treatment with A-3 or TFP upon RPS19 knockdown reversed p53 nuclear accumulation (FIG. 5B). These data demonstrate that calmodulin inhibition can affect p53 nuclear localization and its function as a transcriptional activator.

CD34+ Cells Respond to Calmodulin Inhibition

Figure 6A:
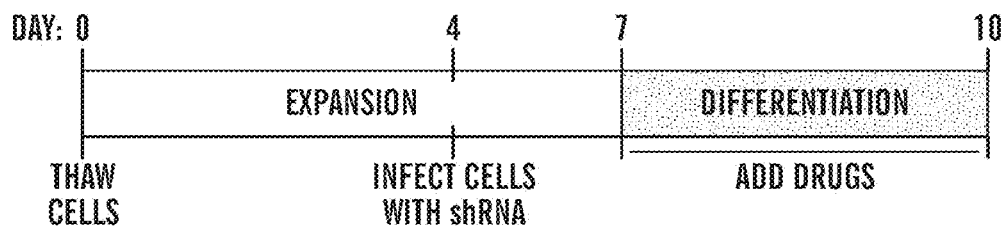
FIGS. 6A-6C show RPS19 erythroid differentiation block rescued with calmodulin inhibitors.

As DBA is a hematopoietic disorder, the inventors next tested the effects of A-3 in CD34+ cells with RPS19 knockdown by siRNA. In an in vitro system that mimics the differentiation of erythrocytes in vivo, the inventors knocked down RPS19 using shRNA. Human CD34+ cells are expanded in culture for 4 days and then infected with RPS19 shRNA or luciferase control shRNA lentiviral construct, selected with puromycin for 2 days and on day 7, the media is replaced with media containing high EPO to initiate erythroid differentiation (FIG. 6A). When RPS19 is reduced during erythroid differentiation, p21 mRNA levels increased about 6-fold compared to luciferase-infected controls and the transferrin receptor, CD71+ and a marker that is first detected at the proerythroblast stage, glycophorin A (GPA), are reduced 40% and 50%, respectively (Dutt et al., 2011). In CD34+ cells, kept in erythroid proliferation media, A-3 was demonstrated to decrease p21 protein. These studies demonstrate that calmodulin inhibition is effective in hematopoietic cells.

Figure 6B:
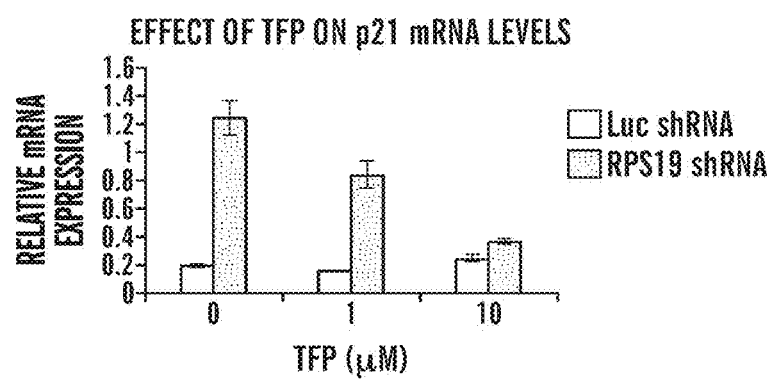
Figure 6C:
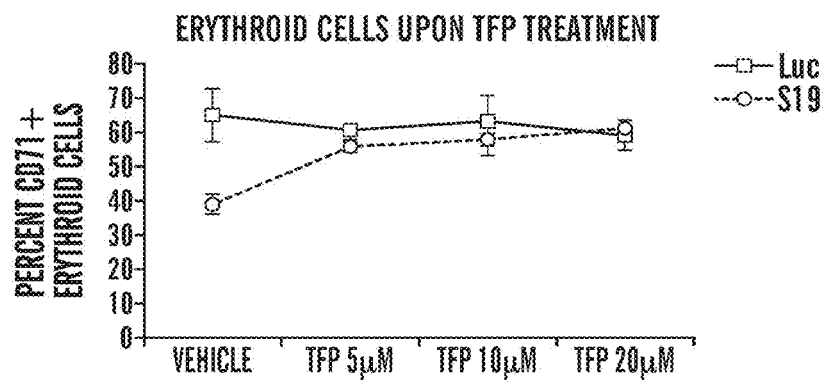

Treatment with the phenothiazine TFP (10 μM) decreased p21 mRNA to control levels (FIG. 6B). Both TFP and fluphenazine are able to rescue CD71+ expression on day 10 of erythroid differentiation (FIG. 6C).

Example 5

Inhibition of Calmodulin-Dependent Enzyme Chk2 is Sufficient for Erythroid Progenitor Rescue Calmodulin interacts with many different enzymes in the cell, including kinases, phosphatases, and phosphodiesterases. To determine which calmodulin-dependent enzyme was responsible for the differentiation rescue, the inventors screened an inhibitor panel against individual enzymes. One inhibitor, BML-277, rescued CD71+ levels and prevented nuclear accumulation of p53 in A549 cells. BML-277 inhibits chk2, a kinase known to be calmodulin-dependent (Arienti et al., 2005). Chk2 can phosphorylate p53, regulating its function.

Example 6

Optimization of Calmodulin Inhibitors for Differentiation Rescue

One class of calmodulin (CaM) inhibitors that can rescue blood cell differentiation discovered by the inventors is a class of FDA-approved phenothiazines, including trifluoperazine, fluphenazine and perphenazine Phenothiazines are FDA-approved as antipsychotics; however, their long-term use is associated with dyskinesia and extrapyramidal effects (Kennedy et al., 1971), making them risky for use in children. Accordingly, one of ordinary skill in the art can modify such phenothiazine compounds so they may not cross the blood brain barrier or may have low dopamine receptor activity, thus producing potentially fewer central nervous system side effects. Additionally, one can also test the novel compounds in DBA patient derived iPS cells to determine if they can also rescue erythroid differentiation or normalize the translational effects. In some embodiments, the calmodulin inhibitors as disclosed herein can be used for the treatment of patients with ribosomal protein disorders and bone marrow failure disorders that result from p53 activation.

Example 7

DBA Patient-Derived iPS Cells

Figure 7:
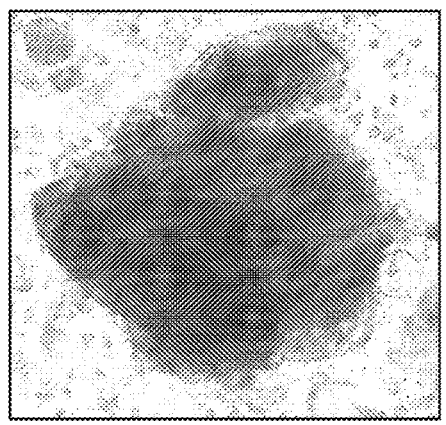
FIG. 7 shows iPS cells derived from a DBA patient can differentiate into erythroid cells. DBA patient-derived iPS cell with an RPS19 mutation, differentiated towards the erythroid lineage.

The inventors obtained 7 fibroblast samples from DBA patients with mutations in either RPS19, RPLS, or RPS24. Using retroviral, episomal, and lentiviral reprogramming methods the inventors derived 35 iPS lines from those samples and validated 9 of the lines through karyotyping and immunofluorescent staining. Six of the lines are from a patient with an RPS19 mutation, two lines are from a patient with an RPLS mutation, and one line is from a patient with an RPS24 mutation. All of the nine lines express the stem cell markers SSEA4, Tra-1-60, Oct4, and Nanog and have a normal karyotype. The RPS19 lines have been extensively characterized. RPS19 protein levels are approximately 50% reduced in primary fibroblasts from a patient with an RPS19 nonsense mutation. RPS19 protein is not down in the iPS cell state. However, when the inventors differentiated the iPS lines into fibroblasts, RPS19 protein was again reduced in some of the fibroblasts. In addition, some fibroblasts senesced earlier than controls. The inventors assessed if there is a cell cycle defect in these re-differentiated DBA fibroblasts. Hematopoietic differentiation of the RPS lines, as well as an RPS24 missense iPS line, demonstrated that all are capable of forming hematopoietic progenitor colonies, including granulocytes, macrophages, and G/M colonies. In an erythroid-specific differentiation assay (Lu et al., 2010), one RPS19 line formed red erythroid progenitor colonies (FIG. 7).

Example 8

Ribosomal protein mutations in patients with DBA cause hematopoietic specific defects, which has been modeled in cell culture, zebrafish, and mice by knockdown or mutation of ribosomal proteins. Herein, the inventors used a chemical screen to identify compounds which rescued the phenotype of rps29 zebrafish mutants. The inventors identified structurally related calmodulin inhibitors, A-3 and W-7 that were effective at rescuing distinct aspects of the phenotype: hematopoietic, endothelial, and apoptotic. Calmodulin inhibition also was demonstrated to block p21 protein activation upon RPS19 knockdown, which is likely the result of decreased p53 and p21 nuclear localization. The inventors also demonstrated that calmodulin inhibitors also function well in hematopoietic cells, as calmodulin inhibitors inhibited or reduced p21 levels in CD34+ cells with low RPS19 and rescues the hemoglobin defect in the zebrafish rps29 mutant. These data demonstrate that calmodulin inhibitors are a useful as a therapeutic for DBA patients.

Nuclear Localization and Calmodulin

The inventors data also indicate that calmodulin has a role in the nuclear localization of both p53 and p21. Calmodulin has been previously reported to play a role in nuclear transport (Sweitzer and Hanover, 1996). Treatment with calmodulin inhibitors has been reported to block p21 nuclear translocation (Taules et al., 1999), with the hypothesis that calmodulin allows p21 nuclear translocation by blocking Ser153 phosphorylation (Rodriguez-Vilarrupla et al., 2005). Although calmodulin inhibition has been shown to affect p21 localization, an effect on p53 localization has not previously been described.

Example 9

Inhibition of Calmodulin as a DBA Therapy

The inventors herein have identified calmodulin inhibitors as a therapeutic approach for targeting the p53 pathway. Inhibiting a component of the p53 pathway will attenuate the effect of ribosomal protein knockdown by preventing p53 and p21 nuclear localization. As such, calmodulin inhibitors provide a method for fine-tuning the p53 pathway. The inventors have demonstrated that the calmodulin inhibitors are effective when different ribosomal proteins are targeted, including rps29 in the zebrafish and rps19 in A549 and CD34+ cells, demonstrating that they would be effective in patients with different ribosomal protein mutations. The calmodulin inhibitor, trifluoperazine (TFP) and other calmodulin inhibitors in the phenothiazine family are currently used for patients with schizophrenia and other diseases.

Calmodulin Inhibitors Rescue Vasculature Defect by a Distinct Mechanism

In the zebrafish rps29$^{-/-}$ embryos, calmodulin inhibitors were demonstrated to rescue the mutation induced flk1 vasculature defect and the hemoglobin and morphological defects, albeit by different mechanisms. $Ca^{2+}$ channel blockers and an inhibitor of calmodulin dependent PDE1 also rescued the flk1 defect in the chemical screen, demonstrating that inhibition of PDE1 could be the relevant calmodulin-dependent enzyme in the endothelial cells. PDE1 acts on both cGMP and cAMP, and cGMP has an established role in NO induced endothelial cell growth (Isenberg et al., 2005). NO donors also rescued the mutant, validating the sufficiency of NO pathway activation to rescue flk1 staining upon rps29$^{-/-}$ mutation, and consistent with previous work by the inventors demonstrating the role of NO at this stage of hemogenic endothelial development in the zebrafish embryo (North et al., 2009). It is suprizing that that calmodulin inhibitors, by targeting two independent pathways of NO and p53, can rescue diverse ribosomal protein mutant phenotypes.

The critical mediator of the DBA red blood cell defect is most likely p53 induced by ribosomal protein knockdown.

Here, the inventors have demonstrated, using a chemical screen in the zebrafish, specific compounds, in particular calmodulin inhibitors that mediate this pathway under ribosomal stress.

REFERENCES

All references cited herein, in the specification and Examples are incorporated in their entirety by reference.

Burns C E, Galloway J L, Smith A C, et al. A genetic screen in zebrafish defines a hierarchical network of pathways required for hematopoietic stem cell emergence. Blood 2009;113:5776-82.

Chin D, Means A R. Calmodulin: a prototypical calcium sensor. Trends Cell Biol 2000;10:322-8.

Danilova N, Sakamoto K M, Lin S. Ribosomal protein S19 deficiency in zebrafish leads to developmental abnormalities and defective erythropoiesis through activation of p53 protein family. Blood 2008;112:5228-37.

Danilova N, Sakamoto K M, Lin S. Ribosomal protein L11 mutation in zebrafish leads to haematopoietic and metabolic defects. Br J Haematol 2011;152:217-28.

Draptchinskaia N, Gustaysson P, Andersson B, et al. The gene encoding ribosomal protein S19 is mutated in Diamond-Blackfan anaemia. Nat Genet 1999;21:169-75.

Dutt S, Narla A, Lin K, et al. Haploinsufficiency for ribosomal protein genes causes selective activation of p53 in human erythroid progenitor cells. Blood 2011;117:2567-76.

Ebert BL, Pretz J, Bosco J, et al. Identification of RPS14 as a 5q-syndrome gene by RNA interference screen. Nature 2008;451:335-9.

Ebert B L, Lee M M, Pretz J L, et al. An RNA interference model of RPS19 deficiency in Diamond-Blackfan anemia recapitulates defective hematopoiesis and rescue by dexamethasone: identification of dexamethasone-responsive genes by microarray. Blood 2005;105:4620-6.

Flygare J, Kiefer T, Miyake K, et al. Deficiency of ribosomal protein S19 in CD34+ cells generated by siRNA blocks erythroid development and mimics defects seen in Diamond-Blackfan anemia. Blood 2005;105:4627-34.

Fumagalli S, Di Cara A, Neb-Gulati A, et al. Absence of nucleolar disruption after impairment of 40S ribosome biogenesis reveals an rpL11-translation-dependent mechanism of p53 induction. Nat Cell Bio! 2009;11:501-8.

Inagaki M, Kawamoto S, Itoh H, et al. Naphthalenesulfonamides as calmodulin antagonists and protein kinase inhibitors. Mol Pharmacol 1986;29:577-81.

Isenberg J S, Ridnour L A, Perruccio E M, Espey M G, Wink D A, Roberts D D. Thrombospondin-1 inhibits endothelial cell responses to nitric oxide in a cGMP-dependent manner. Proc Natl Acad Sci U S A 2005;102:13141-6.

Jaako P, Flygare J, Olsson K, et al. Mice with ribosomal protein S19 deficiency develop bone marrow failure and symptoms like patients with Diamond-Blackfan anemia. Blood 2011;118:6087-96.

Lu S J, Feng Q, Park J S, et al. Biologic properties and enucleation of red blood cells from human embryonic stem cells. Blood 2008;112:4475-84.

McGowan K A, Li J Z, Park C Y, et al. Ribosomal mutations cause p53-mediated dark skin and pleiotropic effects. Nat Genet 2008;40:963-70.

Miyake K, Flygare J, Kiefer T, et al. Development of cellular models for ribosomal protein S19 (RPS19)-deficient diamond-blackfan anemia using inducible expression of siRNA against RPS19. Mol Ther 2005;11:627-37.

North T E, Goessling W, Walkley C R, et al. Prostaglandin E2 regulates vertebrate haematopoietic stem cell homeostasis. Nature 2007;447:1007-11.

North T E, Goessling W, Peeters M, et al. Hematopoietic stem cell development is dependent on blood flow. Cell 2009;137:736-48.

Paffett-Lugassy N N, Zon L I. Analysis of hematopoietic development in the zebrafish. Methods Mol Med 2005;105: 171-98.

Rodriguez-Vilarrupla A, Jaumot M, Abella N, et al. Binding of calmodulin to the carboxy-terminal region of p21 induces nuclear accumulation via inhibition of protein kinase C-mediated phosphorylation of Ser153. Mol Cell Biol 2005;25:7364-74.

Sweitzer T D, Hanover J A. Calmodulin activates nuclear protein import: a link between signal transduction and nuclear transport. Proc Natl Acad Sci U S A 1996;93:14574-9.

Takagi M, Absalon M J, McLure K G, Kastan M B. Regulation of p53 translation and induction after DNA damage by ribosomal protein L26 and nucleolin. Cell 2005; 123:49-63.

Taules M, Rodriguez-Vilarrupla A, Rius E, et al. Calmodulin binds to p21(Cipl) and is involved in the regulation of its nuclear localization. J Biol Chem 1999;274:24445-8.

Taylor A M, Humphries J M, White R M, Murphey R D, Burns C E, Zon L I. Hematopoietic defects in rps29 mutant zebrafish depend upon p53 activation. Exp Hematol 2012; 40:228-37 e5.

Thisse C, Thisse B. High-resolution in situ hybridization to whole-mount zebrafish embryos. Nat Protoc 2008;3:59-69.

Vlachos A, Ball S, Dahl N, et al. Diagnosing and treating Diamond Blackfan anaemia: results of an international clinical consensus conference. Br J Haematol 2008;142:859-76.

Vlachos A, Muir E. How I treat Diamond Blackfan anemia. Blood 2010;116:3715-23.

What is claimed:

1. A method of treating a subject with Diamond Blackfan Anemia (DBA), comprising administering a therapeutically effective amount of a phenothiazine compound or a pharmaceutically acceptable salt thereof to the subject to decrease p53 or p21 in at least one of CD34+ cells, erythroid cells or erythroid differentiated cells in the subject, wherein the phenothiazine compound is selected from the group consisting of:

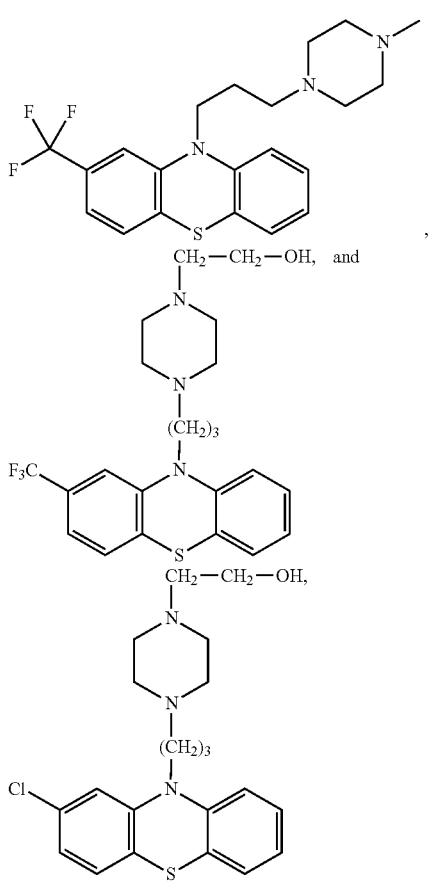

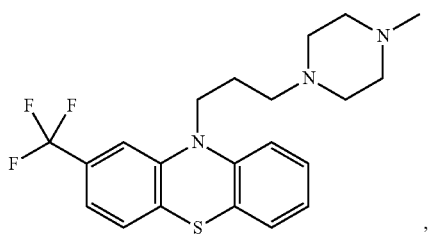 [SMILES: CN1CCN(CCCN2c3ccccc3Sc3ccc(C(F)(F)F)cc32)CC1]

or a pharmaceutically acceptable salt thereof.

2. The method of claim 1, wherein the phenothiazine compound is

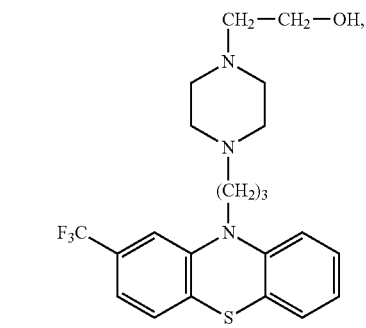

or a pharmaceutically acceptable salt thereof.

3. The method of claim 1, wherein the phenothiazine compound is

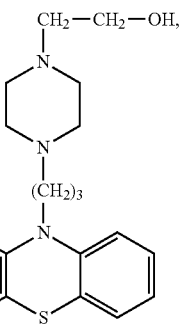

or a pharmaceutically acceptable salt thereof.

4. The method of claim 1, wherein the phenothiazine compound is

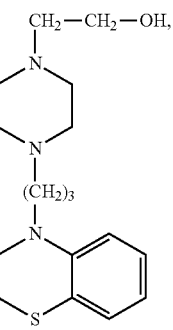

or a pharmaceutically acceptable salt thereof.

5. The method of claim 1, wherein the subject has DBA1, DBA2, DBA3, DBA4, DBA5, DBA6, DBA7, or DBA8.

6. The method of claim 1, wherein the subject has a mutation in ribosomal protein 19 (RPS19).

7. The method of claim 1, wherein the subject has a mutation in ribosomal protein selected from RPS7, RPS10, RPS19, RPS24, PRS26, RPS17, PRS27L RPS29, RPL35A, PRL5 and PPL11.

8. The method of claim 1, wherein the subject has a mutation in a ribosomal protein selected from the group consisting of: rPL2A, rPL2B, rPL3, rpL4A, rPL4B, rPL7A, rPL7B, rPL10, rPL11, rPL16A, rPL17A, rPL17B, rPL18A, rPL18B, Rp119A, rPL19, rPL25, rPL29, rpL31A, rpL31B, rPL36A, rPL40A, rPS1A, rPS6A, rPS6B, rPS14A, rPS15, rPS19, rPS23B, rPS25A, rPS26B, rPS29, rPS29B and rPS31.

9. The method of claim 1, wherein the subject is administered another therapeutic agent to treat the ribosomal protein defect, selected from the group consisting of: corticosteroids, blood transfusions.

10. The method of claim 1, wherein the phenothiazine compound increases the number of CD71+ erythroid cells in the subject, or increase the hemoglobin levels in the subject, or both.

11. A method of treating a subject with Diamond Blackfan Anemia (DBA), comprising administering a therapeutically effective amount of CGS-9343 (zaldaride maleate), having the structure:

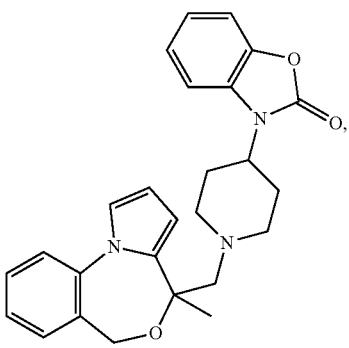 [SMILES: CC1(CN2CCC(n3c(=O)oc4ccccc43)CC2)OCc2ccccc2-n2cccc21]

or a pharmaceutically acceptable salt thereof to the subject to decrease p53 or p21 in at least one of CD34+ cells, erythroid cells or erythroid differentiated cells in the subject.

12. The method of claim 11, wherein the subject has DBA1, DBA2, DBA3, DBA4, DBA5, DBA6, DBA7, or DBA8.

13. The method of claim 11, wherein the subject has a mutation in ribosomal protein 19 (RPS19).

14. The method of claim 11, wherein the subject has a mutation in ribosomal protein selected from RPS7, RPS10, RPS19, RPS24, PRS26, RPS17, PRS27L RPS29, RPL35A, PRL5 and PPL11.

15. The method of claim 11, wherein the subject has a mutation in a ribosomal protein selected from the group consisting of: rPL2A, rPL2B, rPL3, rpL4A, rPL4B, rPL7A, rPL7B, rPL10, rPL11, rPL16A, rPL17A, rPL17B, rPL18A, rPL18B, Rp119A, rPL19, rPL25, rPL29, rpL31A, rpL31B, rPL36A, rPL40A, rPS1A, rPS6A, rPS6B, rPS14A, rPS15, rPS19, rPS23B, rPS25A, rPS26B, rPS29, rPS29B and rPS31.

16. The method of claim 11, wherein the subject is administered another therapeutic agent to treat the ribosomal protein defect, selected from the group consisting of: corticosteroids, blood transfusions.

17. The method of claim 11, wherein the phenothiazine compound increases the number of CD71+ erythroid cells in the subject, or increase the hemoglobin levels in the subject, or both.

* * * * *

UNITED STATES PATENT AND TRADEMARK OFFICE
CERTIFICATE OF CORRECTION

PATENT NO. : 11,065,258 B2  
APPLICATION NO. : 16/538293  
DATED : July 20, 2021  
INVENTOR(S) : Leonard I. Zon Page 1 of 1

It is certified that error appears in the above-identified patent and that said Letters Patent is hereby corrected as shown below:

In the Specification

At Column 1, Lines 31-34, please delete:
"This invention was made with government support under Grant Number HL01001 awarded by the National Institutes of Health. The Government has certain rights in the invention."

And insert therefor:
--This invention was made with government support under Grant Number HL010001, awarded by the National Institutes of Health. The Government has certain rights in the invention.--

Signed and Sealed this  
Thirteenth Day of December, 2022

Katherine Kelly Vidal  
*Director of the United States Patent and Trademark Office*